United States Patent
Wolf et al.

(10) Patent No.: US 7,759,120 B2
(45) Date of Patent: Jul. 20, 2010

(54) SEEDING IMPLANTABLE MEDICAL DEVICES WITH CELLS

(75) Inventors: Michael F. Wolf, Golden Valley, MN (US); Laurie A. Yunker, Richfield, MN (US); Paul V. Trescony, Champlin, MN (US)

(73) Assignee: Kps Bay Medical, Inc., Minneapolis, MN (US)

( * ) Notice: Subject to any disclaimer, the term of this patent is extended or adjusted under 35 U.S.C. 154(b) by 621 days.

(21) Appl. No.: 11/515,344

(22) Filed: Sep. 1, 2006

(65) Prior Publication Data
US 2007/0059335 A1 Mar. 15, 2007

Related U.S. Application Data

(63) Continuation-in-part of application No. 11/367,006, filed on Mar. 2, 2006, which is a continuation-in-part of application No. 11/071,597, filed on Mar. 2, 2005, now abandoned.

(51) Int. Cl.
*C12N 11/08* (2006.01)
(52) U.S. Cl. ............... 435/395; 435/177; 435/180; 435/182; 435/402; 623/915; 623/916; 600/36
(58) Field of Classification Search ............... None
See application file for complete search history.

(56) References Cited

U.S. PATENT DOCUMENTS

| | | | |
|---|---|---|---|
| 4,177,334 A | 12/1979 | Okita | |
| 4,418,691 A | 12/1983 | Yannas et al. | |
| 4,458,678 A | 7/1984 | Yannas et al. | |
| 4,465,200 A * | 8/1984 | Percarpio | 215/247 |
| 4,505,266 A | 3/1985 | Yannas et al. | |
| 4,553,272 A | 11/1985 | Mears | |

(Continued)

FOREIGN PATENT DOCUMENTS

EP 0 462 051 12/1991

(Continued)

OTHER PUBLICATIONS

Current Protocols in Cell Biology (2000), Appendix 2B "Media Formulations" A.2B.1-A.2B.3, John Wiley & Sons, Inc.*

(Continued)

*Primary Examiner*—Allison M Ford
(74) *Attorney, Agent, or Firm*—Haugen Law Firm PLLP

(57) ABSTRACT

Apparatus and methods for seeding an implantable medical device, such as a vascular prosthesis, with cells, such as endothelial cells, are described. The invention supports techniques for seeding a luminal surface of the device with axial centrifugation. Cells are introduced in suspension into the lumen of the device. The introduction of the cells may occur after a blood centrifugation product, such as platelet-poor plasma, is applied to the luminal surface. After the cells are introduced, the device is then subjected to centrifugation around a longitudinal axis defined by the lumen. Axial centrifugation causes the cells to concentrate toward and adhere to the luminal surface. Shortly after axial centrifugation, the seeded device can be presented for implantation in a patient. The implantable medical device may be inserted into a protective sleeve prior to seeding the device with cells, and the sleeve may or may not be removed prior to implantation.

8 Claims, 35 Drawing Sheets

U.S. PATENT DOCUMENTS

| | | | |
|---|---|---|---|
| 4,596,577 A | 6/1986 | Sato | |
| 4,804,382 A | 2/1989 | Turina et al. | |
| 4,820,626 A | 4/1989 | Williams et al. | |
| 4,960,423 A | 10/1990 | Smith | |
| 5,035,708 A | 7/1991 | Alchas et al. | |
| 5,171,261 A | 12/1992 | Noishiki et al. | |
| 5,230,693 A | 7/1993 | Williams et al. | |
| 5,376,118 A | 12/1994 | Kaplan et al. | |
| 5,385,229 A | 1/1995 | Bittmann et al. | |
| 5,387,236 A | 2/1995 | Noishiki et al. | |
| 5,396,898 A | 3/1995 | Bittmann et al. | |
| 5,433,909 A | 7/1995 | Mortakos et al. | |
| 5,437,900 A | 8/1995 | Kuzowski | |
| 5,462,781 A | 10/1995 | Zukowski | |
| 5,474,824 A | 12/1995 | Mortakos et al. | |
| 5,628,781 A | 5/1997 | Williams et al. | |
| 5,634,879 A | 6/1997 | Mueller-Glauser et al. | |
| 5,653,745 A | 8/1997 | Trescony et al. | |
| 5,744,515 A | 4/1998 | Clapper | |
| 5,817,153 A | 10/1998 | Pendl et al. | |
| 5,861,033 A | 1/1999 | Mortakos et al. | |
| 5,879,383 A | 3/1999 | Bruchman et al. | |
| 5,925,074 A | 7/1999 | Gingas et al. | |
| 6,171,344 B1 | 1/2001 | Atala | |
| 6,287,275 B1 | 9/2001 | Atala | |
| 6,352,555 B1 | 3/2002 | Dzau et al. | |
| 6,368,859 B1 | 4/2002 | Atala | |
| 6,376,244 B1 | 4/2002 | Atala | |
| 6,428,802 B1 | 8/2002 | Atala | |
| 6,432,081 B1 | 8/2002 | Atala | |
| 6,479,064 B1 | 11/2002 | Atala | |
| 6,482,645 B2 | 11/2002 | Atala | |
| 6,514,292 B1 | 2/2003 | Atala | |
| 6,517,571 B1 | 2/2003 | Brauker et al. | |
| 6,519,492 B1 | 2/2003 | Yoo et al. | |
| 6,547,719 B1 | 4/2003 | Atala et al. | |
| 6,576,019 B1 | 6/2003 | Atala | |
| 6,579,313 B2 | 6/2003 | Dzau et al. | |
| 6,620,203 B2 | 9/2003 | Atala | |
| 6,673,339 B1 | 1/2004 | Atala et al. | |
| 6,704,604 B2 | 3/2004 | Soukup et al. | |
| 2001/0048949 A1 | 12/2001 | Atala | |
| 2001/0053353 A1 | 12/2001 | Griffith et al. | |
| 2001/0055588 A1 | 12/2001 | Griffith-Cima et al. | |
| 2002/0055702 A1 | 5/2002 | Atala et al. | |
| 2002/0055731 A1 | 5/2002 | Atala et al. | |
| 2002/0055786 A1 | 5/2002 | Atala | |
| 2002/0091448 A1 | 7/2002 | Atala | |
| 2002/0094570 A1 | 7/2002 | Atala | |
| 2002/0102727 A1 | 8/2002 | Atala | |
| 2002/0192730 A1 | 12/2002 | Soker et al. | |
| 2003/0004559 A1 | 1/2003 | Lentz et al. | |
| 2003/0096406 A1 | 5/2003 | Atala et al. | |
| 2003/0096407 A1 | 5/2003 | Atala et al. | |
| 2003/0120352 A1 | 6/2003 | Atala | |
| 2003/0124099 A1 | 7/2003 | Atala | |
| 2003/0180268 A1 | 9/2003 | Atala | |
| 2003/0208279 A1 | 11/2003 | Atala | |
| 2003/0211601 A1 | 11/2003 | Atala | |
| 2003/0211602 A1 | 11/2003 | Atala | |
| 2003/0215459 A1 | 11/2003 | Atala et al. | |
| 2003/0215945 A1 | 11/2003 | Atala | |
| 2005/0055085 A1 | 3/2005 | Rivron et al. | |
| 2006/0173467 A1* | 8/2006 | Karwoski et al. | 606/108 |

FOREIGN PATENT DOCUMENTS

| | | |
|---|---|---|
| EP | 0 630 432 | 12/1994 |
| EP | 0 790 042 | 8/1997 |
| EP | 1 002 859 | 5/2000 |
| EP | 0 787 021 | 8/2002 |
| EP | 0 774 981 | 11/2002 |
| EP | 0 927 052 | 4/2003 |
| EP | 1 032 435 | 9/2003 |
| EP | 1 246 653 | 5/2004 |
| EP | 1 079 772 | 2/2005 |
| JP | 06339520 | 12/1994 |
| WO | WO 93/18214 | 9/1993 |
| WO | WO 00/02998 | 1/2000 |
| WO | WO 01/47574 | 7/2001 |
| WO | WO 01/48153 | 7/2001 |
| WO | WO 01/49210 | 7/2001 |
| WO | WO 01/49827 | 7/2001 |
| WO | WO 01/82828 | 11/2001 |
| WO | WO 01/83709 | 11/2001 |
| WO | WO 01/87192 | 11/2001 |
| WO | WO 02/061424 | 8/2002 |
| WO | WO 02/092108 | 11/2002 |
| WO | WO 03/042405 | 5/2003 |
| WO | WO 03/043674 | 5/2003 |
| WO | WO 03/043675 | 5/2003 |

OTHER PUBLICATIONS

English translation of EP 0 462 051 (Baitella-Eberle et al), original publication date: Dec. 18, 1991, 15 pgs total.*

Ballermann, B.J. and Ott, M.J., "Adhesion and differentiation of endothelial cells by exposure to chronic shear stress: a vascular graft model," Blood Purif. 13(3-4):125-34 (1995).

Deutsch, M., Fischlein, Meinhart J.G., and Zilla, P., "In Vitro Endothelialization of Sympathetic Vascular Grafts in Long Term Clinical Use," Tissue Engineering of Vascular Prosthetic Grafts. Zilla, P. and Greisler, H.P., eds. pp. 189-194, R.G. Landes Company, 1999.

Herring, M., Dilley, R., Jerslid, R., Boxer, L., Gardner, A., and Glover, J., "Seeding arterial prosthesis with vascular enothelium, The nature of the lining," Ann Surg. 190:84-90, 1979.

Dardik, A., Liu, A., and Ballermann, B., "Chronic in vitro shear stress stimulates endothelial cell retention on prosthetic vascular grafts and reduces subsequent in vivo neointimal thickness," J Vasc Surg. 29(1):157-167 (1999).

Giudiceandrea A., Seifalian, A.M., Krijgsman, B., and Hamilton, G., "Effect of porlonge pulsatile shear stress in vitro on endothelial cell seeded PTFE and compliant polyurethane vascular grafts," Eur J Vasc Endovasc Surg. 15(2):147-54 (1998).

Miyata, T., Conte, M.S., Trodel, L.A., Mason, D., Whittemore, A.D., and Birinyi, L,K., "Delayed exposure to pulsatile shear stress improves retention of human saphenous vein endothelial cells on seeded ePTFE grafts," J Sur Res. 50:485-493 (1991).

Meinhart, J.G., Deutsch, M., Fischlein, T., Howanietz, N., Froschl, A., Zilla, P., "Clinical autologous in vitro endothelialization of 153 infrainguinal ePTFE grafts," Annals of Thoracic Surgery, 71(5 Suppl.):S327-331, (2001).

Nerem, R.M., Alexander, R.W., Chappell, D.C., Medford, R.M., Varner S.E., and Taylor, W.R., "The study of the influence of flow on vascular endothelial biology," Am J Med Sci, 316(3):169-175 (1998).

Ott, M. J. and Ballermann, B.J., "Shear stress-conditioned, endothelial cell-seeded vascular grafts: improved cell adherence in response to in vitro shear stress," Surgery. 117(3):334-339 (1995).

Sank, A., Rostami, K., Weaver, F., Ertl, D., Yellin, AJ, Nimni, M., And Tuan, T., "New evidence and new hope concerning endothelial seedings of vascular grafts," Am J Surg. 164:199-204 (1992).

Voorhees, A.B., Jaretzki, A., Blakemore, A.H., "The use of tubes constructed from Vinyon N cloth in bridging arterial defects." Ann Surg 135:336, 1952.

Weinberg, C.B., and Bell, E., "A blood vessel model constructed from collagen and cultured vascular cells," Science. 231:397-400 (1986).

Godbey et al., "A Novel Use of Centrifugal Force for Cell Seeding Into Porous Scaffolds," Biomaterials 25 (2004) 2799-2805.

* cited by examiner

|   | MATERIAL | INCUBATION | % CELL RETENTION |
|---|---|---|---|
| A | ePTFE | 0 | 28.0 |
|   | bePTFE™ | 0 | 61.6 |
| B | ePTFE | 1 HOUR/STATIC | 45.0 |
|   | bePTFE™ | 1 HOUR/STATIC | 55.4 |
| C | ePTFE | 1 HOUR/1 g | 43.8 |
|   | bePTFE™ | 1 HOUR/1 g | 62.0 |
| D | ePTFE | 5 HOURS/STATIC | 26.5 |
|   | bePTFE™ | 5 HOURS/STATIC | 44.4 |

FIG. 34

|   | MATERIAL | INCUBATION | FLOW | % CELL RETENTION |
|---|---|---|---|---|
| A | ePTFE | 0 | 0 | 36.0 |
|   | bePTFE™ | 0 | 0 | 54.7 |
| B | ePTFE | 1 HOUR | 0 | 38.8 |
|   | bePTFE™ | 1 HOUR | 0 | 65.0 |
| C | ePTFE | 0 | 1 HOUR | 25.1 |
|   | bePTFE™ | 0 | 1 HOUR | 44.9 |
| D | ePTFE | 1 HOUR | 1 HOUR | 24.3 |
|   | bePTFE™ | 1 HOUR | 1 HOUR | 75.4 |

FIG. 35

| MATERIAL | # of GRAFTS | PATENT GRAFTS | OCCLUDED GRAFTS |
|---|---|---|---|
| ePTFE | 16 | 10 (63%) | 6 (37%) – 2 infected |
| bePTFE™ | 16 | 14 (88%) | 2 (12%) – 2 infected |
| TOTAL | 32 | 24 (75%) | 8 (25%) - 4 infected |

FIG. 48

| TEST | PATENCY | THROMBOSIS | NEOINTIMAL FORMATION (SEM) |
|---|---|---|---|
| Cell Seeing vs. No Cell Seeding | $P < 0.08$ | $P < 0.004$ | $P < 0.04$ |
| ePTFE vs. bePTFE™ | $P < 0.07$ | $P < 0.0001$ | NS |
| Forward vs. Reverse | NS | NS | NS |
| PPP vs. no PPP | NS | $P < 0.009$ | $P < 0.01$ |

FIG. 49

| TEST | NEOINTIMAL FORMATION | CELLULARITY | MACROPHAGE INFILTRATION | THROMBOSIS |
|---|---|---|---|---|
| Cell Seeing vs. No Cell Seeding | $P < 0.008$ | $P < 0.001$ | $P < 0.007$ | NS |
| ePTFE vs. bePTFE™ | NS | $P < 0.09$ | NS | $P < 0.08$ |
| Forward vs. Reverse | NS | NS | NS | NS |
| PPP vs. no PPP | NS | NS | NS | NS |

FIG. 50

| GRAFT PRE-TREATMENT | % OF INITIALLY SEEDED CELLS |
|---|---|
| SERUM | 9% - 58% |
| FIBRONECTIN | 5% - 46% |
| MAGELLAN™ PPP | 107% - 564% |
| MATRIGEL™ | 11% - 137% |

FIG. 52

SEEDING IMPLANTABLE MEDICAL DEVICES WITH CELLS

This application is a continuation-in-part of U.S. application Ser. No. 11/367,006, filed Mar. 2, 2006, which is a continuation-in-part of U.S. application Ser. No. 11/071,597, filed Mar. 2, 2005. The entire content of both of these applications is incorporated herein by reference.

TECHNICAL FIELD

The invention relates to materials and devices implantable in a living human or animal body, such as materials and devices used in vascular prostheses.

BACKGROUND

Some patients develop conditions that can be corrected with implantable medical devices such as mechanical and bioprosthetic heart valves, coronary stents, stent grafts, abdominal aortic aneurysm (AAA) grafts and other devices. Conditions that affect blood flow through the vessels of the body, for example, may be treated with vascular grafts, in which a surgeon applies the graft to supplant the damaged vascular tissue. Coronary artery disease, peripheral vascular disease and venipuncture for treatment of end stage renal disease are examples of conditions in which vascular flow is affected, and which can be addressed with surgical grafts.

Vascular grafts may be autologous, i.e., the graft may be taken from the patient for transplantation at another site. In some cases, however, an autologous graft may not be feasible, and a synthetic vascular graft may be employed instead. A synthetic vascular graft is a tube-shaped prosthesis made of a biocompatible material such as expanded polytetrafluoroethylene (ePTFE). The synthetic vascular graft includes a lumen through which blood flows.

In a vessel, the intima is the layer closest to the lumen where blood flows. It is made up mainly of a monolayer of endothelial cells attached to a basement membrane and matrix molecules. The endothelial cells are specialized cells that line the lumen of blood vessels, and play several roles. Endothelial cells secrete vasoactive substances, for example, and secrete substances that stimulate new vessel growth and promote or inhibit contraction and sometimes proliferation of smooth muscle cells in vessel walls in response to hemodynamic demands. Endothelial cells are also influential in formation and dissolution of thrombus, which is a precipitate of blood components that can restrict blood flow through the vessel lumen.

In humans, implanted vascular grafts typically heal by formation of an acellular psuedo-intima without large-scale outgrowth of the native endothelial cell lining at the point of anastomosis. It has been discovered that it is highly beneficial for a synthetic vascular graft to include a layer of endothelial cells in the lumen, to prevent thrombosis and to suppress abnormal smooth muscle cell proliferation that could lead to stenosis or narrowing of the vessel. To promote the formation of a homogeneous, dense and confluent layer of endothelial cells inside the synthetic vascular graft, techniques have been developed for "endothelial cell seeding" of vascular grafts. In general, this "seeding" or deposition of cells involves harvesting autologous endothelial cells and transplanting the harvested cells to the lumen of the synthetic vascular graft.

SUMMARY

In general, the invention is related to devices and methods that are useful for seeding implantable medical devices with cells, such as mechanical and bioprosthetic heart valves, coronary stents, stent grafts and AAA grafts. For purposes of describing the invention, however, the discussion will focus upon the seeding of a vascular prosthesis. The devices are configured to be implanted in a living body, i.e., a human or animal body.

Various methods for preparation of an implantable medical device to enhance endothelial cell seeding are described. Some of the methods involve creation of recesses in the luminal surface of implantable medical device, such as a vascular prosthesis, that can receive endothelial cells. Other methods include soaking the implantable medical device in one or both of a blood centrifugation product, such as platelet-poor plasma, or a calcium containing media to prepare the luminal surface for cell adhesion. When the implantable medical device is constructed of a material such as expanded polytetrafluoroethylene (ePTFE), the recesses may be created by physical processing of the microstructures of the material. The recesses support and shelter endothelial cells deposited on the lumen and reduce the risk of the cells being washed away. When the endothelial cells wash away, the vessel is less likely to endothelialize, and is at greater risk of developing complications, such as thrombosis and stenosis.

The invention describes methods for seeding the luminal surface of an implantable medical device with axial centrifugation. Cells are introduced in suspension into the lumen of the device, and the device is subjected to centrifugation around a longitudinal axis defined by the lumen. Axial centrifugation causes the cells to concentrate toward the luminal surface. Shortly after axial centrifugation, the seeded device can be presented for implantation in a patient. Because cells concentrate toward the luminal surface, the cells are more likely to coat the luminal surface, and are more likely to inhabit the sheltering recesses.

The methods described herein for cell seeding of an implantable medical device can be performed directly in the operating room, during one surgical procedure. While the patient is undergoing surgery, the cells may be introduced into the lumen of the prosthesis, and the prosthesis seeded by subjection to axial centrifugation. Also described are methods to prepare the implantable medical device to receive the cells, as well as to protect of the implantable medical device from hazards associated with handling.

Also described herein is an apparatus to facilitate cell seeding of an implantable medical device that can be coupled to a tabletop vertical or horizontal centrifuge that performs axial centrifugation.

In one embodiment, the invention relates to a method for seeding an implantable medical device with cells. The method comprises introducing cells into a lumen of the implantable medical device adapted to be implanted in a living body, i.e., a human or animal body. The lumen includes a luminal surface that includes ePTFE. The method also includes applying centrifugation to the device to rotate the device around a longitudinal axis defined by the lumen. The method also describes placing the device in a protective sleeve prior to introducing the cells. The method further describes placing the device, with or without the protective sleeve, in a tube with an open end prior to introducing the cells, and sealing the open end of the tube with a plug after introducing the cells.

In another embodiment, the invention relates to a method for seeding an implantable medical device with cells. The method comprises introducing cells into a lumen of the implantable medical device adapted to be implanted in a human or animal body. The lumen includes a luminal surface having recesses defined by nodes lifted from the surface. The method also includes applying axial centrifugation to the device.

In an additional embodiment, the invention relates to an apparatus comprising an adapter, a tube and a plug. The adapter is configured to mate with a rotor of a centrifuge proximate to an axis of rotation of the rotor. The adapter includes a chamber that extends in the direction of the axis. The tube is configured to receive an implantable medical device, and is further configured to be received in the chamber. The tube has an open end. The plug is configured to seal the open end of the tube.

In another embodiment, the invention is directed to a method for seeding cells on a luminal surface of an implantable medical device, the method comprising applying a blood centrifugation product to the luminal surface, introducing cells into a lumen of the implantable medical device, wherein the luminal surface defines the lumen, and the lumen defines a longitudinal axis, and centrifuging the implantable medical device by rotating the implantable medical device substantially around the longitudinal axis.

In another embodiment, the invention is directed to a method comprising inserting an implantable medical device into a protective sleeve, inserting the protective sleeve into a tube through an open end of the tube, wherein the tube defines a longitudinal axis, sealing the open end of the tube with a septum, delivering cells to a lumen of the implantable medical device via the septum, and centrifuging the implantable medical device with the cells in the lumen by rotating the tube substantially around the longitudinal axis.

In another embodiment, the invention is directed to a system for protecting a vascular prosthesis during a cell seeding procedure, the system comprising a protective sleeve that defines a lumen sized to receive the vascular prosthesis, a tube sized to receive the protective sleeve via an open end, wherein the tube is adapted to be received by a centrifuge, and a first septum that seals the open end of the tube, wherein the septum is adapted to allow delivery of materials to a lumen of the vascular prosthesis when the prosthesis is within the tube.

In the case of an implantable medical device, such as a vascular prosthesis, manufactured and seeded as described, fewer endothelial cells will be washed away when the prosthesis is implanted, thereby benefiting the patient. Also, various embodiments of the invention take advantage of physical properties of ePTFE, a material that has a proven track record in implantable medical devices. The invention may provide an improved surface without adversely affecting the favorable features of ePTFE, such as biocompatibility, physical properties and ease of handling and suturing.

In addition, the invention may also make a "one-stage procedure" feasible, in which endothelial cells can be harvested, a prosthesis can be prepared and seeded with the harvested cells, and the seeded device can be presented for implantation in a single surgical operation. Seeding with axial centrifugation can be an efficient way to deploy cells rapidly and evenly on the luminal surface. Further, the methods for preparing the implant described herein may increase implant longevity. For example, an implant treated with a blood centrifugation product, such as platelet-poor plasma, and then seeded may be less likely to incur thrombosis formation, and more likely to experience neointimal cell growth.

The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

FIG. 34 is a table showing data collected pertaining to devices seeded with axial centrifugation, including devices with an incubation period after centrifugation.

FIG. 35 is a table showing data collected pertaining to devices seeded with axial centrifugation, including devices with an incubation period and flow acclimatization after centrifugation.

FIG. 48 is a table showing experimental data derived from evaluation of the vascular grafts removed from the canines in the animal study.

FIG. 49 is an ANOVA table showing statistical data (P values) derived from evaluation of the vascular grafts removed from the canines in the animal study.

FIG. 50 is an ANOVA table showing statistical data (P values) derived from a histological evaluation of the vascular grafts removed from the canines in the animal study.

FIG. 52 is a table showing experimental cell growth data derived from grafts treated with different mediums before cell seeding in an in vitro experiment.

DETAILED DESCRIPTION

Figure 1:
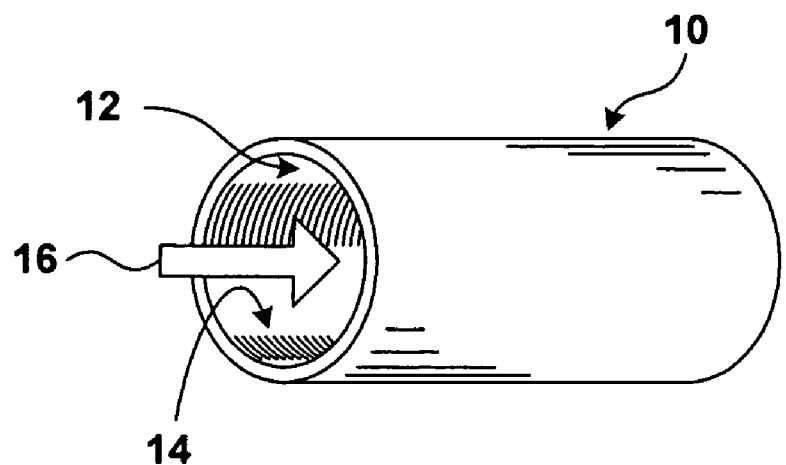
FIG. 1 is a perspective view of a vascular prosthesis.

FIG. 1 is a diagram of an implantable medical device, in particular, a vascular prosthesis 10. For purposes of describing the invention, the discussion below focuses upon the seeding of vascular prosthesis 10 with cells. The invention is not limited to this particular implantable medical device, however. Each of these implantable medical devices can be configured to be implanted in a living body, i.e., a human or animal body.

Prosthesis 10 is a generally tube-shaped structure that includes a lumen 12 through which a fluid can flow. In a typical application, vascular prosthesis 10 supplants a blood vessel, and the fluid that flows through lumen 12 is blood. A luminal surface 14 of vascular prosthesis 10 comes in contact with the blood.

The geometry of luminal surface 14 of vascular prosthesis 10 defines a "luminal direction," which is along the longitudinal axis of the tubular prosthesis. Although fluid may physically flow through lumen 12 forward or backward along the luminal direction, fluid generally flows predominantly in one direction in an implanted environment. It is therefore useful to define a "flow direction" which represents a particular direction of fluid flow. In FIGS. 1 and 3-6, arrow 16 identifies the flow direction. Flow direction 16 is coincident with the luminal direction, but is directed in a single direction. Fluid moving in flow direction 16 may be considered as moving "forward," and fluid moving opposite flow direction 16 may be considered as moving "backward."

Figure 2:
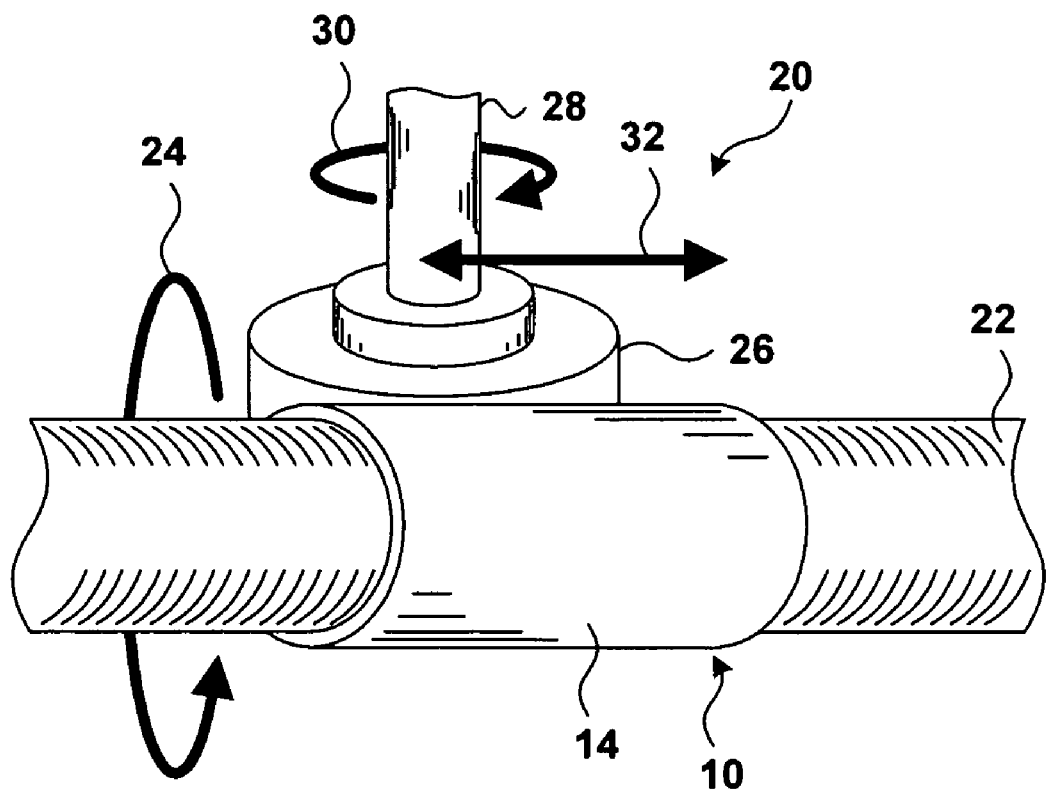
FIG. 2 is a perspective view of a tool assembly for processing a vascular prosthesis.

FIG. 2 is a diagram of an exemplary tool assembly 20 that processes vascular prosthesis 10 by rubbing vascular prosthesis 10. "Rubbing" comprises any process that includes moving a tool with pressure relative to vascular prosthesis 10, such as by scraping, scoring, abrading, brushing, chafing, scratching or scuffing.

As shown in FIG. 2, vascular prosthesis 10 has been everted, i.e., vascular prosthesis 10 has been turned "inside out" to facilitate processing with tool assembly 20. Vascular prosthesis 10 has been mounted on a rotatable supporting mandrel 22, which may be free to rotate as shown by directional arrow 24. Although mandrel 22 is shown in FIG. 2 as having a generally circular cross-section, the mandrel may alternatively have cross-section that is hexagonal, square, rectangular, or any other desired shape.

A tool 26 rubs luminal surface 14. In exemplary tool assembly 20, tool 26 is mounted on a rotating shaft 28 that rotates as shown by directional arrow 30. When tool 26 is brought in contact with luminal surface 14 and rotated, tool 26 rubs against luminal surface 14. Mandrel 22 or shaft 28 or both further have freedom to move in a transverse direction, as shown by directional arrow 32.

By rotating tool 26 and moving tool 26 and prosthesis 10 transversely to one another, and by rotating mandrel 22, tool 26 can be brought into contact with any point on luminal surface 14. In this way, tool 26 can rub the entire luminal surface 14. Although not essential for the invention, there are advantages to rubbing the entire luminal surface, as will be described below. In addition, mandrel 22 need not have a circular or rounded cross-section as shown in FIG. 2, but may include one or more flat surfaces, e.g., may have a hexagonal, square, or rectangular cross-section, as described above.

When vascular prosthesis 10 is constructed of a material such as expanded polytetrafluoroethylene (ePTFE), rubbing luminal surface 14 with tool 26 creates recesses in the microstructures of luminal surface 14. In particular, rubbing luminal surface 14 lifts microscopic "nodes" from luminal surface 14, forming recesses that can receive seeded autologous endothelial cells. As used herein, "endothelial cells" includes endothelial precursor or stem cells, as well as developed endothelial cells.

Tool 26 may be any of several tools. Tool 26 may be solid, such as a rotating drum of metal, plastic, rubber or ceramic. Tool 26 may also include a wheel brush with bristles. The bristles may be constructed of any material, including metal, plastic, rubber or ceramic. Through experimentation, it has been discovered that a wheel brush with metal bristles, such as brass or stainless steel bristles, can generate recesses in the luminal surface. A wheel brush with nylon bristles also is effective in generating recesses. A technique for rubbing a luminal surface of a vascular prosthesis with a tool will be described below.

Figure 3:
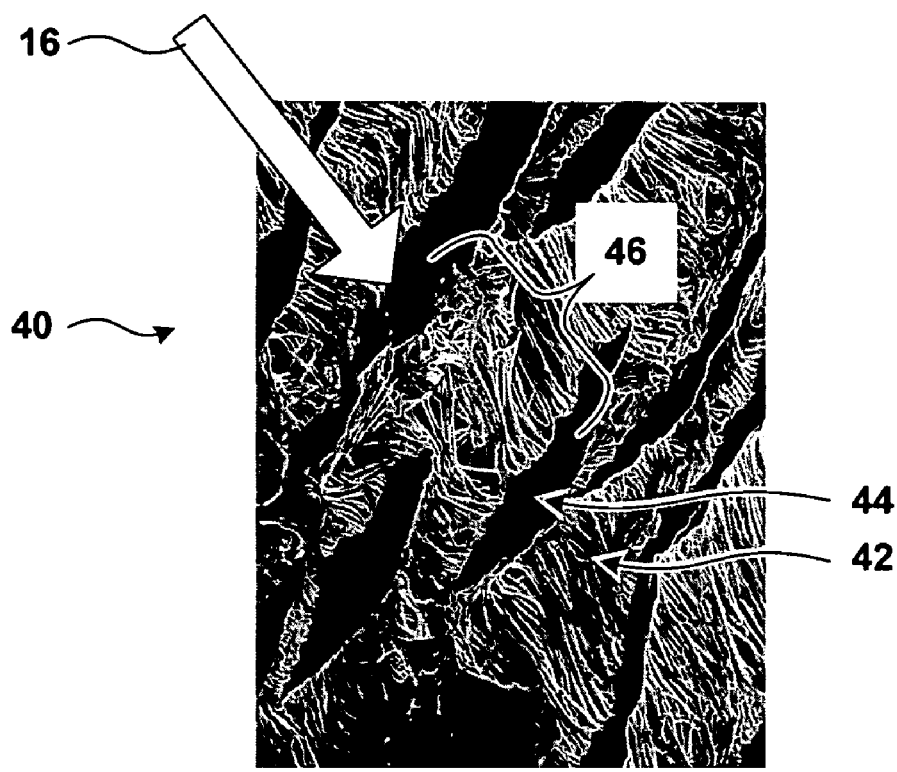
FIG. 3 is a scanning electron microscope (SEM) image of expanded polytetrafluoroethylene (ePTFE) material prior to processing.

FIG. 3 is an image of ePTFE material 40 taken by a scanning electron microscope (SEM). The image of FIG. 3 depicts ePTFE material 40 such as that found in a standard vascular graft such as that shown in FIG. 1. In particular, the image of FIG. 3 depicts a microscopic view of the luminal surface of a prosthesis, i.e., the surface that may be in contact with a flowing bodily fluid, such as blood.

Two types of microstructures provide ePTFE material 40 with its strength and other physical properties, and these microstructures are evident on the luminal surface shown in FIG. 3. In particular, ePTFE material 40 includes thin polytetrafluoroethylene (PTFE) fibrils 42 draped between the much thicker islands or "nodes" 44 of PTFE. The orientations of fibrils 42 and nodes 44 are substantially perpendicular to one another, and result from the manufacture of ePTFE.

In general, the manufacture of ePTFE includes preparation of a material that includes PTFE particles that have been fused together. At one stage in the manufacturing process, the material is stretched or "expanded." The expansion causes fibrils 42 to form in the direction of the expansion, giving ePTFE directionality. The degree of expansion also affects the internodal distance, i.e., the average distance between neighboring nodes in the direction of expansion. Internodal distances may be, for example on the order of about 30 to 90 micrometers. Reference numeral 46 shows a typical internodal distance.

In FIG. 3, ePTFE material 40 has not yet been rubbed with a tool. For reference, FIG. 3 shows flow direction 16. Flow direction 16 is substantially perpendicular to the orientation of nodes 44, and substantially parallel to the orientation of fibrils 42.

Figure 4:
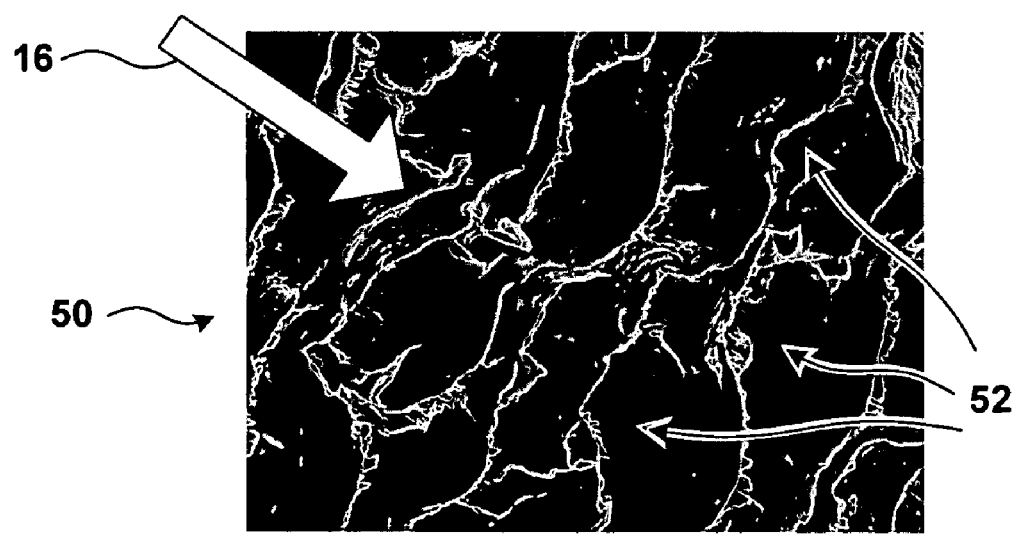
FIG. 4 is an SEM image of ePTFE material after processing.

FIG. 4 is an image of ePTFE material 50 taken by an SEM. Material 50 has been subjected to preparation, thereby creating a plurality of recesses 52 in the luminal surface. As will be described below, rubbing the luminal surface with a tool generates recesses 52. Recesses 52 can receive endothelial cells. Recesses 52 represent "grooves," "wells," "harbors," "pockets" or "hiding spaces" for the endothelial cells.

As shown in FIG. 4, recesses 52 are oriented at least partially along the luminal direction. In particular, the recesses extend into the luminal surface, but extend at least partially in the direction opposite flow direction 16. In other words, a fluid moving in flow direction 16 would generally flow over recesses 52, rather than into recesses 52.

As shown in FIG. 4, rubbing the luminal surface affects the fibrils network visible in FIG. 3. As a result of rubbing, many of the fibrils are disrupted, resulting in smooth, fibril-free surfaces. This effect is generally restricted to the luminal surface, however. Fibrils beneath the luminal surface are largely intact, imparting strength and other physical properties to material 50. In addition, fibrils may reside inside recesses 52. It has been discovered through experimentation that the extent of smooth, fibril-free surfaces is generally a function of the extent of rubbing.

Viewed with an SEM, the luminal surface of material 50 resembles a series of overlapping layers. The layers separate from one another in a scale-like texture that resembles a "fish-scale" pattern, creating recesses that can harbor endothelial cells.

Figure 5:
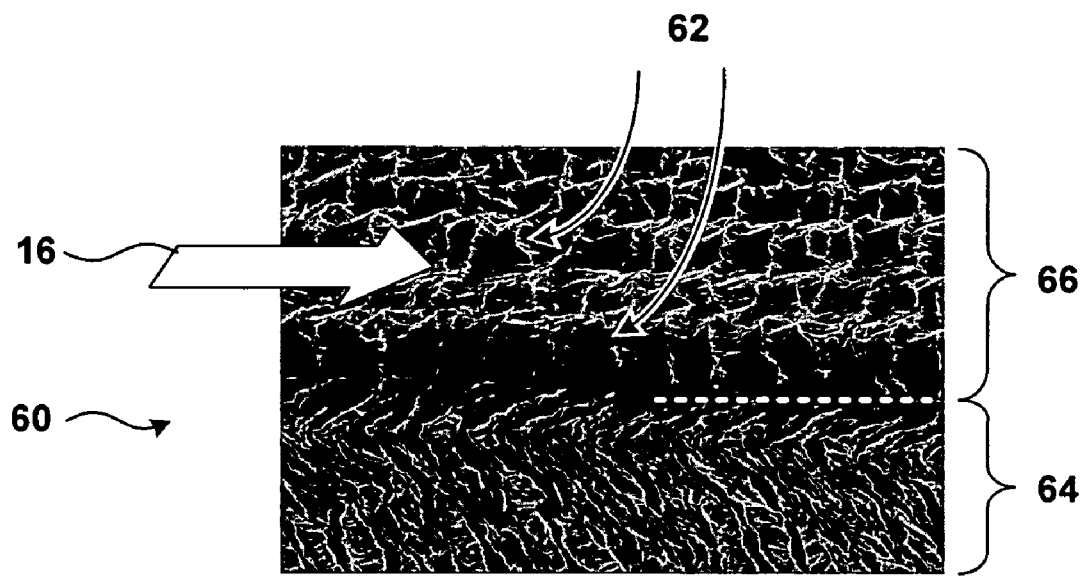
FIG. 5 is an SEM image of ePTFE material after processing, shown in cross-section and at an oblique angle.

FIG. 5 is an image of ePTFE material 60 taken by an SEM that shows the structure of material 60 following preparation and creation of recesses 62. FIG. 5 shows in part a cross section 64 of material 60, i.e., material beneath the luminal surface. Although rubbing has affected the luminal surface, the material below the luminal surface maintains its structure. In a typical vascular prosthesis having a wall thickness of three-tenths to seven-tenths of a millimeter, rubbing would generally affect no more than five to ten percent of the thickness of the material.

FIG. 5 also provides an oblique view 66 of the luminal surface. As can be seen from oblique view 66, recesses 62 are oriented at least partially along the luminal direction, and extend into the luminal surface at least partially in the direction opposite flow direction 16.

Figure 6:
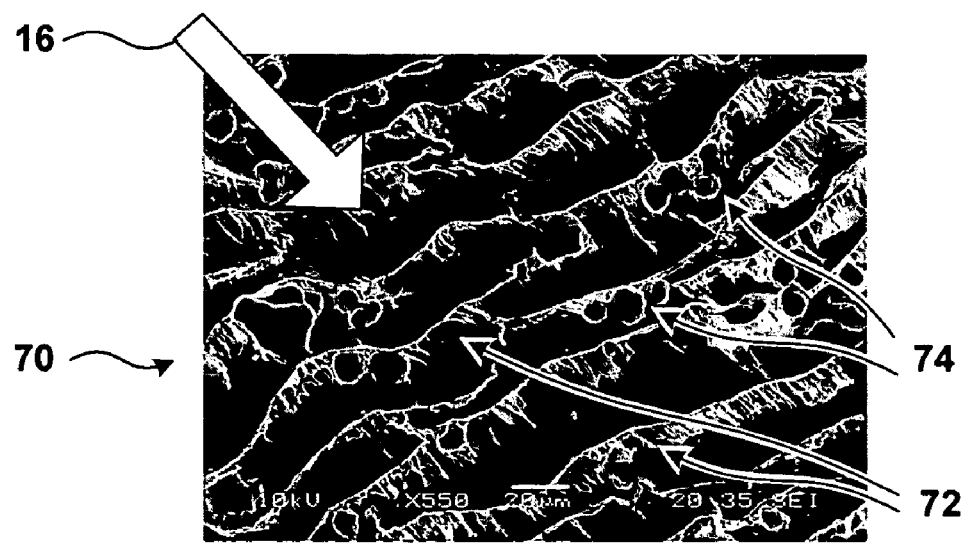
FIG. 6 is an SEM image of ePTFE material after processing, seeded with endothelial cells.

FIG. 6 is an image of ePTFE material 70 taken by an SEM. Material 70 is similar to material 50 in FIG. 4, and material 60 in FIG. 5, but material 70 includes recesses 72 in the luminal surface and endothelial cells 74 received in recesses 72. As shown in FIG. 6, a fluid moving in flow direction 16 would generally flow over recesses 72 and over cells 74. As a result, a cell residing in a recess is subjected to less shear force from the fluid than a cell outside a recess, and is less likely to be exposed and washed away by the fluid.

In a conventional vascular prosthesis seeded with endothelial cells, the endothelial cells deposited on the lumen of the prosthesis tend to be washed away by the flow of blood. Even when the cells adhere to the luminal surface, the shear forces associated with fluid flow often overcome the adhesion and wash the endothelial cells away. When the endothelial cells are washed away, the vessel is less likely to endothelialize and is at greater risk of developing complications, such as thrombosis and stenosis.

In a vascular prosthesis with a luminal surface such as shown in FIG. 6, however, shear forces may wash away fewer endothelial cells. Because endothelial cells 74 reside in recesses 72, fluid flow along fluid direction 16 is less likely to dislodge and wash away endothelial cells 74 in recesses 72. With time, endothelial cells 74 grow in situ, mature and colonize the luminal surface, with recesses 72 providing a foundation for growth and colonization. As result, the vascular prosthesis maintains a population of endothelial cells that help reduce the risk of complications.

In addition, rubbing results in smooth, fibril-free surfaces. Endothelial cells 74 may typically adhere more efficiently to smooth nodal surfaces than to fibrils. Rubbing the luminal surface with a tool, in addition to creating recesses, may also create a more suitable surface for cell adhesion.

Figure 7:
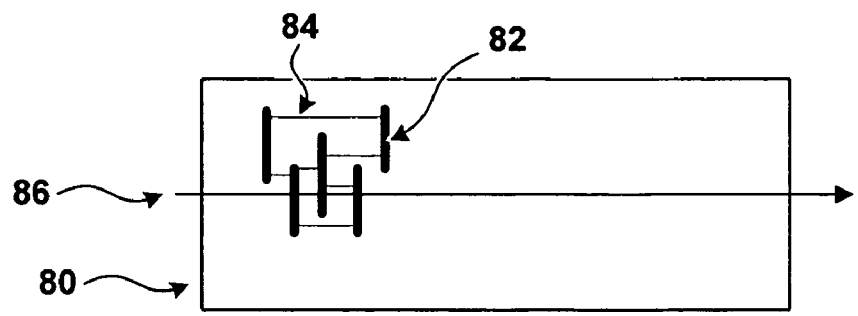
FIG. 7 is a diagram illustrating the structure of ePTFE material.
Figure 8:
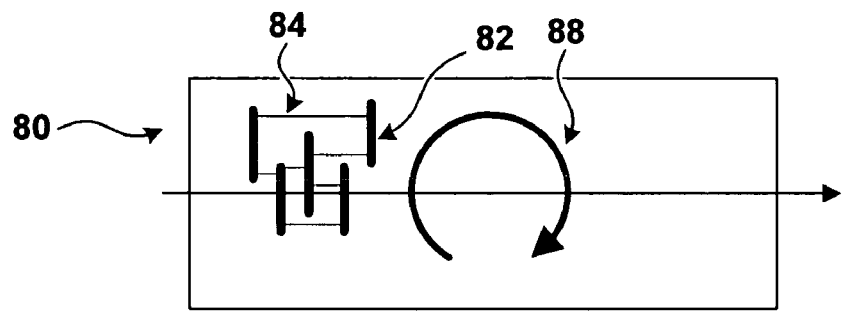
FIGS. 8-10 are diagrams illustrating exemplary techniques for rubbing ePTFE material with a tool.
Figure 9:
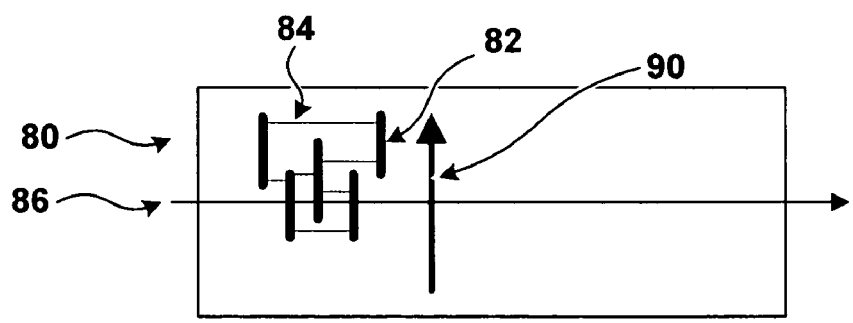
Figure 10:
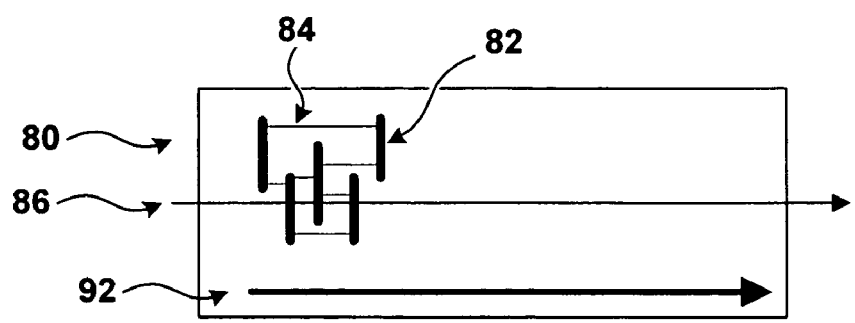

As noted above, the manufacture of ePTFE includes an expansion that imparts directionality to ePTFE. FIG. 7 is a diagram of an ePTFE sample 80 that illustrates the directionality of ePTFE material. In FIG. 7, sample 80 includes nodes 82 and fibrils 84. Arrow 86 identifies a direction that is substantially perpendicular to the orientation of nodes 82, and substantially parallel to the orientation of fibrils 84. FIGS. 8-10 are diagrams illustrating techniques for rubbing ePTFE sample 80 with a tool.

As shown in FIG. 8, one technique for rubbing sample 80 includes rotational rubbing with a tool such as a wheel brush. Rotational rubbing may be accomplished using tool assembly 20 shown in FIG. 2 by bringing the circular face of tool 26, rather than the side of tool 26, into contact with prosthesis 10. With rotational rubbing, the tool rubs the luminal surface in many directions 88 simultaneously. Some of the rubbing may be substantially parallel to the orientation of nodes 82, and some may be substantially perpendicular to the orientation of nodes 82.

FIG. 9, illustrates another technique for rubbing, i.e., radial rubbing with a tool. Radial rubbing comprises rubbing the luminal surface of sample 80 in a direction 90 that is substantially parallel to the orientation of nodes 82, and substantially perpendicular to the orientation of fibrils 84. Rotational rubbing may be accomplished using tool assembly 20 shown in FIG. 2 by bringing the side of tool 26 into contact with prosthesis 10, and orienting mandrel 22 and shaft 28 in the same direction.

A further technique, shown in FIG. 10, includes transverse rubbing of sample 80 with a tool. Transverse rubbing comprises rubbing the luminal surface in a direction 92 that is substantially perpendicular to the orientation of nodes 82, and substantially parallel to the orientation of fibrils 84. FIG. 2 depicts tool assembly 20 rubbing vascular prosthesis 10 in a transverse direction.

Through experimentation, it has been discovered that transverse rubbing as depicted in FIG. 10, is effective in lifting nodes from the luminal surface to define a plurality of recesses. Radial rubbing, as depicted in FIG. 9, tends to disrupt fibrils 84 without lifting large numbers of nodes 82 to create recesses. Rotational rubbing, as depicted in FIG. 8, tends to produce regions in which nodes are lifted, comparable to the effect of transverse rubbing, and regions in which nodes are not lifted, comparable to the effect of radial rubbing.

It is possible to rub sample 80 with a tool in multiple directions simultaneously. For example, it is possible to rub sample 80 in a direction that has a radial rubbing component and a transverse rubbing component. In general, the greater the transverse rubbing in relation to the radial rubbing, the more nodes are lifted and the more recesses are created. It is also possible to repeat rubbing of the same region of sample 80 in the same way or a different way. Repeat rubbing can further refine the structure of the formed recesses.

Translational rubbing disrupts fibrils 84 on the luminal surface, but also lifts or "plucks" nodes from the luminal surface, thereby creating recesses oriented at least partially along the luminal direction. There may be one or more mechanisms that cause the nodes to be lifted from the luminal surface. When the tool used to rub the luminal surface is a wheel brush with bristles, for example, the bristles may contact nodes and lift the nodes from the luminal surface by friction. The contact between the tool and the surface may also facilitate PTFE "smearing," in which PTFE structures spreads and merge with one another, generating recesses in the process.

While rubbed prosthesis 10 provides a surface that may be conducive for cell adhesion, an unrubbed prosthesis may still be adequate for cell adhesion. As will be described below, the luminal surface of prosthesis 10 may be soaked in additional media solutions that may help the cells adhere are grow on the luminal surface of the prosthesis.

Figure 11:
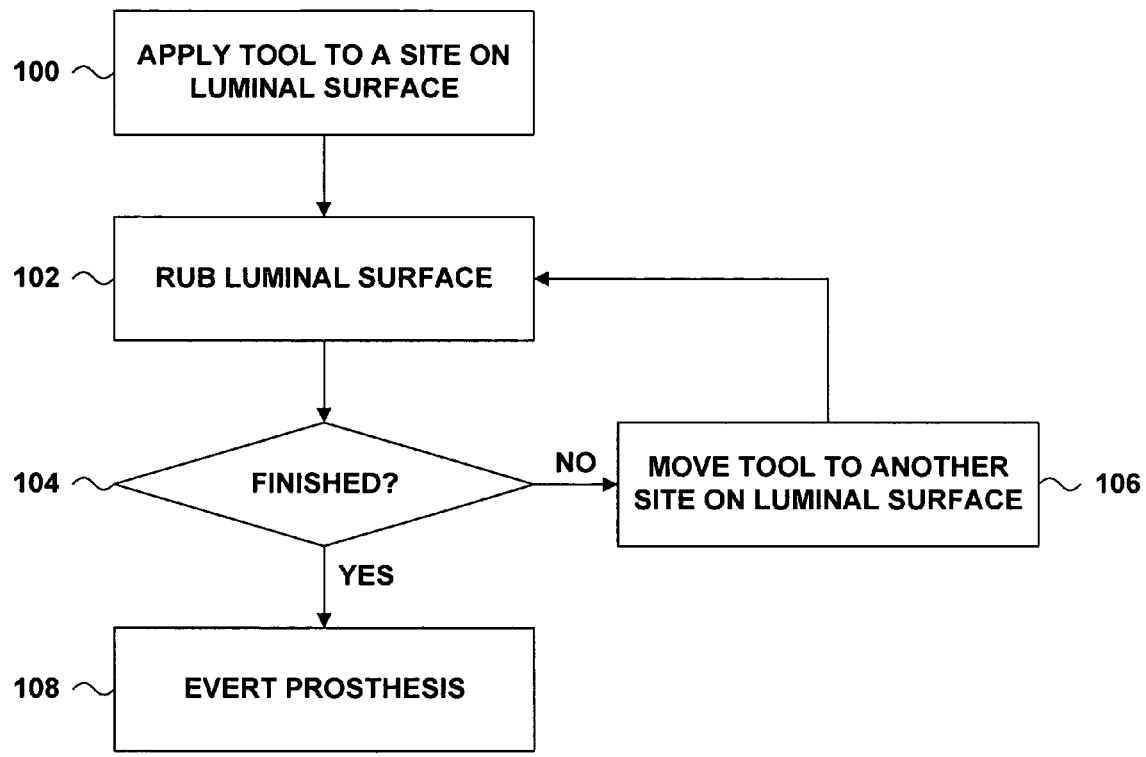
FIG. 11 is a flow diagram illustrating a technique for processing a vascular prosthesis.

FIG. 11 is a flow diagram illustrating a process for preparing a luminal surface of a vascular prosthesis. The process includes applying a tool to a site on the luminal surface (100) rubbing the luminal surface with the tool (102). The rubbing lifts nodes, thereby creating recesses oriented at least partially along the luminal direction.

Exemplary tool assembly 20 shown in FIG. 2 depicts vascular prosthesis 10 mounted on a rotatable supporting mandrel 22, with tool 26 brought in contact with luminal surface 14 of vascular prosthesis 10. Tool 26 rubs luminal surface 14 of vascular prosthesis 10 when rotating shaft 28 rotates. By rotating tool 26 and moving tool and prosthesis 10 transversely to one another, and by rotating supporting mandrel 22, tool 26 can be brought into contact with any point on luminal surface 14.

In some implementations, mandrel 22 includes one or more flat surfaces. When prosthesis 10 is mounted on such a mandrel, prosthesis 10 conforms to the shape of mandrel 22 and flattens. Mandrel 22 can rotate to bring a flat surface to bear, and then cease rotation. Tool 26 can rub luminal surface 14 of vascular prosthesis 10 where surface 14 is flattened.

Accordingly, once a site on the luminal surface has been rubbed, the process includes determining whether other sites need to be rubbed as well (104). In some circumstances, the entire luminal surface of the prosthesis may be rubbed. In other circumstances, it may be desirable to seed endothelial cells at specified sites, and only these specified sites will be rubbed. These specified sites may form patterns, such as longitudinal or radial patterns. By selection of specific sites for rubbing, it is possible to create "paths" for cell growth in situ.

If additional rubbing is indicated, the tool is applied to another site (106) and the process is continued (102). When tool 26 has completed rubbing, the prosthesis may be everted for implantation (108), if necessary. Eversion may also be performed before rubbing, to bring luminal surface 14 to bear. In some embodiments, an everted prosthesis may be rubbed again, thereby processing the abluminal surface as well as the luminal surface.

It is believed to be possible to rub a luminal surface without everting the prosthesis, e.g., by running a brush through the lumen one or more times. Accordingly, everting the prosthesis for processing is not essential to the invention. Even so, mounting the prosthesis on a supporting mandrel, as shown in FIG. 2, may allow for very precise control of the rubbing.

In one embodiment of the invention, a 4 millimeter diameter ePTFE vascular graft was everted, placed over a mandrel attached to a tooling jig parallel to the rotational axis of a model lathe via an adjustable loading spring, and the tooling jig fixed to the tool stock of an EMCO Unimat PC model lathe. A wheel brush with densely packed nylon bristles (The Mill-Rose Company, Mentor Ohio, Catalog No. 71810, 1 inch (2.5 cm) diameter, 0.006 inch (150 micrometer) in diameter bristles) was secured in the chuck of a vertical milling head attached to the model lathe. The tool stock was positioned to place the everted graft in contact with the brush attached to the vertical milling head. Uniform translation of the graft across the brush was achieved by attaching the tool stock lead screw to either a 2-rpm or a 10-rpm synchronous motor. While the brush was rotated at speeds ranging from 350 to 2500 rpm, the graft was first passed in one direction across the brush at 0.075 inches (1.9 mm) per minute (2 rpm synchronous motor) or 0.375 inches (9.5 mm) per minute (10 rpm synchronous motor) with a contact force of 15 gram weight (0.033 lb). The graft was then passed a second time across the rotating brush in the opposite direction with a contact force of 55 gram weight (0.12 lb) over the same range of brush rotation and tool stock translation speeds. The ePTFE may have a wide range of average internodal distances, e.g., from 10 to 200 micrometers between nodes, but good results were obtained with average internodal distances in the range of 30 to 90 micrometers. Vascular grafts of ePTFE are available from a variety of manufacturers.

In one embodiment of the invention, a wheel brush with densely packed nylon bristles (Mill-rose No. 71810, 1 inch (2.5 cm) in diameter, each bristle about 0.006 inches (150 micrometers) in diameter) was rotated at 350 to 2500 revolutions per minute against a vascular prosthesis made of ePTFE. The prosthesis had been everted so that that luminal surface was more accessible. The brush was moved along the prosthesis transversely at 1100 to 6500 inches per minute (28 to 165 meters per second). Forces in the range of 30 to 100 grams weight (0.066 to 0.22 pounds) were applied between the brush and the luminal surface. The ePTFE may have a wide range of average internodal distances, e.g., from 10 to 200 micrometers between nodes, but good results were obtained with average internodal distances in the range of 30 to 90 micrometers. Vascular grafts of ePTFE are available from a variety of manufacturers.

Brushing as described above does not necessarily lift every node in the surface, nor does it necessarily lift all nodes to the same degree. It is not uncommon, however, for a node to be lifted from the surface by many times its normal height.

The process depicted in FIG. 11 is not necessarily restricted to vascular grafts. Implantable devices other than vascular grafts may include ePTFE, and may benefit from having surface recesses for harboring endothelial or other cells, such as cells that improve healing following implantation. Even if not seeded with cells, the implantable devices may realize benefits from having surfaces undergo a process such as that depicted in FIG. 11. For example, the surfaces may improve healing, reduce thrombosis, or decrease fibrous capsule formation. Implantable devices that may include ePTFE, and that may benefit from having surface recesses may include, for example, implantable prostheses for plastic surgery, artificial ligaments, annuloplasty rings, vascular patches, tubes for neural cell growth, sheathed stents, cardiac assist devices, sensors, pacemaker leads, catheters, shunts, sutures and heart valve sewing rings. Such devices may be implantable on a permanent or a temporary basis.

In addition, when the vascular prosthesis or other implantable device is made from ePTFE, the invention is not limited to physical rubbing with a solid tool. It is believed that nodes may be lifted from the surface of ePTFE by application of a pressurized fluid, such as air or water, to a surface made of ePTFE. In other words, an air jet or water jet may supply sufficient friction to lift nodes so as to define a plurality of recesses. Rubbing or application of a pressurized fluid applies a force to the ePTFE, thereby lifting nodes to define recesses. These techniques are not exclusive of one another. For example, a tool may rub the surface of ePTFE when the surface is coated with a liquid.

Figure 12:
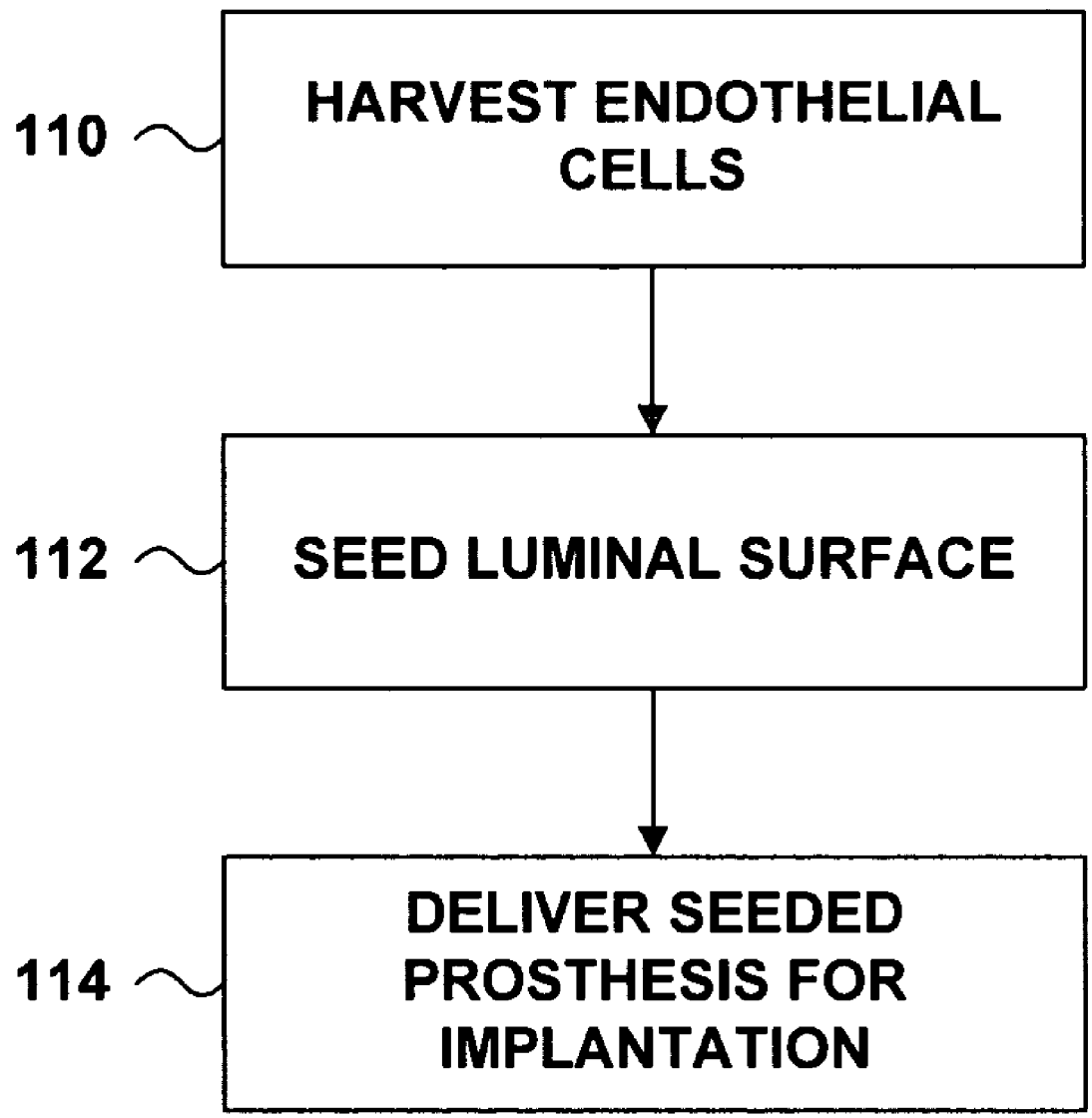
FIG. 12 is a flow diagram illustrating an implantation technique.

FIG. 12 is a flow diagram showing a technique for preparation of a vascular prosthesis for implantation. FIG. 12 depicts a "one-stage procedure," i.e., a procedure for preparation of a vascular prosthesis during a single surgical operation.

The technique of FIG. 12 includes harvesting endothelial cells (110). In a typical operation to repair a damaged vessel with a prosthesis, a surgeon retrieves a source of endothelial cells from the patient before or during the procedure to repair the damaged vessel. A surgeon may, for example, retrieve an expendable subdermal vein that includes endothelial cells, and supply the vein to the medical staff for harvesting of the cells. Another harvesting technique involves taking endothelial cells from adipose tissue. While the staff harvests the cells and prepares the prosthesis, the surgeon may begin repairing the damaged vessel, e.g., obtaining access to the implantation site and preparing the site to receive the prosthesis.

The staff may harvest the cells (110) using any harvesting method. The cells may be separated form the supplied vein and placed in suspension. The staff seeds the prosthesis with harvested endothelial cells (112). The prosthesis is a device having a plurality of recesses sized to receive endothelial cells, with at least some of the recesses oriented at least partially along the luminal direction. The prosthesis will ordinarily have been brought into the operating room with the recesses already formed, and with the prosthesis ready for seeding. The prosthesis may also be premarked to indicate to the surgeon the intended direction of fluid flow through the lumen.

Any seeding method (112) may be used. For example, the fluid with suspended endothelial cells may be introduced into the lumen of the prosthesis, and the prosthesis may be spun with a centrifuge to cause the cells to come in contact with the luminal surface and be received in the recesses. Techniques for seeding with a centrifuge will be discussed in detail below. Following seeding, the seeded prosthesis is supplied to the surgeon for implantation (114). Harvesting and seeding in this way can be accomplished quickly, typically in sixty minutes or less, and sometimes in fifteen minutes or less.

Figure 13:
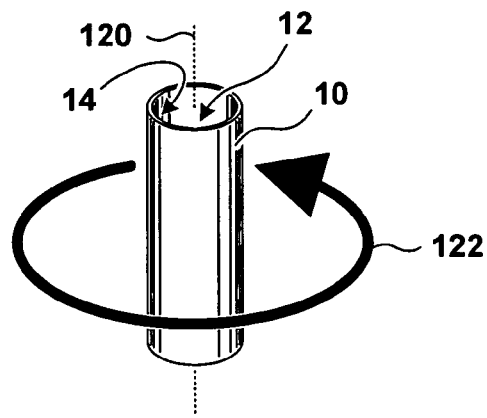
FIG. 13 is a perspective diagram illustrating axial centrifugation of a vascular prosthesis.

FIG. 13 is a schematic view of an implantable medical device being rotated with a centrifuge (not shown). Once again, the implantable medical device is vascular prosthesis 10, but the invention is not limited this device. Vascular prosthesis 10 is rotated to seed luminal surface 14 with cells. Lumen 12 defines a longitudinal luminal axis 120, which is substantially perpendicular to the orientation of nodes on luminal surface 14, and substantially parallel to the orientation of fibrils on luminal surface 14. As indicated by directional arrow 122, the centrifuge rotates prosthesis 10 axially, i.e., centrifuge rotates prosthesis 10 around axis 120.

Although FIG. 13 depicts a vascular prosthesis, other implantable medical devices also have lumens that define longitudinal luminal axes. Many such devices can be seeded using the apparatus and methods described herein. Such implantable medical devices include, but are not limited to, mechanical and bioprosthetic heart valves, coronary stents, stent grafts and AAA grafts. Each of these devices includes a lumen and a longitudinal axis defined by the lumen. For purposes of simplicity, however, the discussion will focus upon the seeding of a vascular prosthesis.

Figure 14:
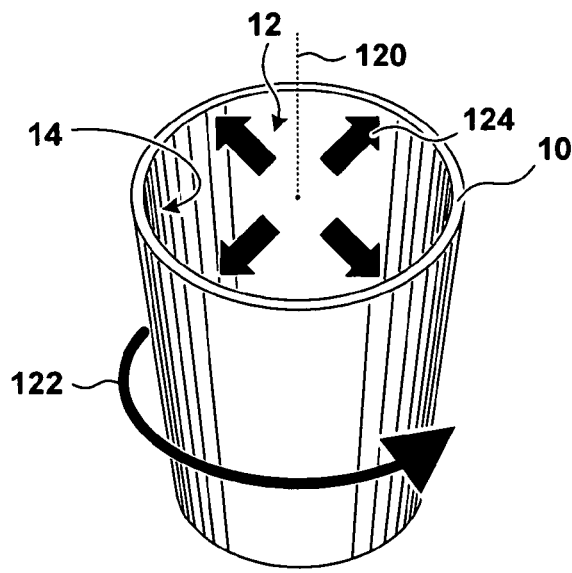
FIG. 14 is a perspective diagram illustrating the effect of axial centrifugation of a vascular prosthesis upon cells in suspension.

FIG. 14 illustrates the effect of axial centrifugation. Although not shown in FIG. 14, the open ends of prosthesis 10 could be plugged to prevent leakage of material from prosthesis 10 during axial centrifugation. Cells in suspension introduced into lumen 12 are prevented from moving out of lumen 12 by rotating luminal surface 14. The force exerted on the cells in suspension by rotating luminal surface 14 is a function of the speed of rotation, the radius measured from axis 120 to luminal surface 14, and the mass of the cells. The cells have greater mass per unit volume than the suspension, so the cells tend to separate from the suspension and concentrate toward luminal surface 14, as indicated by arrows 124. The overall effect of axial centrifugation is to increase the concentration of cells on luminal surface 14.

The centripetal acceleration of a centrifuge is typically expressed in terms of "g." 1 g is approximately equal to the acceleration due to gravity on the Earth's surface, 100 g is one hundred times 1 g, and so on. In a centrifuge that can apply axial or longitudinal or angular centrifugation, the centrifuge typically applies more g's with longitudinal and axial centrifugation than with angular centrifugation for a given angular velocity, because objects that receive longitudinal or angular centrifugation typically are further from the axis of rotation of the centrifuge rotor. Computation of g's is straightforward, because centripetal acceleration is a function of the distance of luminal surface 14 from the axis of centrifugation and the angular velocity of the centrifuge rotor.

Axial centrifugation of a 4 millimeter diameter prosthesis with a typical tabletop centrifuge can produce about 1,000 g, although this is not a maximum for all centrifuges. Increased concentration of cells on luminal surface 14 can be produced with accelerations from 1 g to 10,000g, although higher g's increase the risk of damage to the cells. Through experimentation, it has been discovered that centrifugation at 50 g to 500 g for one to ten minutes produces comparable concentrations of cells on luminal surface 14. In practice, centrifugation could involve applying between 1 g and 1,000 g, preferably 50 g to 500 g, and more preferably about 250 g. Centrifugation could be applied for any length of time, but usually less than one hour and preferably for one to ten minutes.

Any of several media can serve as suspensions for endothelial cells. The suspension can be a buffered salt solution, for example, or a physiological balanced electrolyte solution such as Plasma-Lyte® A, commercially available from Baxter International, Inc, or EBM-2™ (endothelial basal media), commercially available from Cambrex Corporation. As discussed below, the introduction of a suspension can be preceded by introduction of preparatory fluids.

Figure 15:
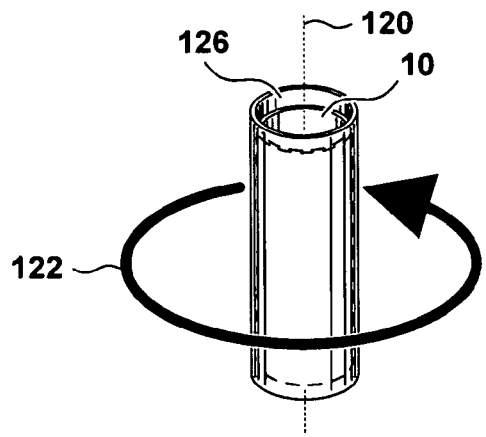
FIG. 15 is a perspective diagram illustrating axial centrifugation of a vascular prosthesis with a protective sleeve.

FIG. 15 is a schematic view of a vascular prosthesis 10 being spun with a centrifuge (not shown) to seed luminal surface 14. Unlike FIGS. 13 and 14, vascular prosthesis 10 is inside a protective sleeve 126. Sleeve 126 may be constructed from any of several metallic, glass or ceramic materials or polymers, and may further include reinforcing fillers or fibers. Sleeve 126 may also include one or more lubricants that make it easier for a person to put prosthesis 10 into or remove prosthesis 10 from sleeve 126. An exemplary material for construction of sleeve 126 is polytetrafluoroethylene (PTFE), which is more resistant to bending than ePTFE.

Sleeve 126 is configured to receive and protect prosthesis 10, and is shaped accordingly. When prosthesis 10 is cylindrical, sleeve 126 may likewise be substantially cylindrical. FIG. 15 depicts sleeve 126 as having a substantially circular cross-section of constant diameter, but other configurations may also work well. For example, sleeve 126 can have a tapered shape. Sleeve 126 can be open at one end or open at both ends. In addition, the thickness of sleeve 126 need not be constant. Sleeve 126 can have a circular cross-section, or one that is substantially oval or polygonal. One or more surfaces of sleeve 126 may be smooth, ridged, grooved, textured and the like.

Sleeve 126 can be useful in preparation of prosthesis 10 for seeding and in maintaining the seeded condition of prosthesis 10 following seeding, by reducing the likelihood of reintroduction of air onto luminal surface 14 or the bulk of the prosthesis material. When wet ePTFE, for example, is bent or kinked, then straightened, air enters the bulk of the material, and the material soaks up air.

In a dry prosthesis constructed from ePTFE as described above, air can be present in the bulk of the material and in the recesses and the spaces between nodes and fibrils of luminal surface 14. To promote effective seeding of luminal surface 14, it is desirable to remove these small pockets of air. A procedure called "wetting," in which a fluid is introduced into lumen 12, can displace the air. Because ePTFE is generally hydrophobic, water makes a poor wetting agent for displacing the pockets of air. One example of a more effective wetting agent is ethanol. Wetting can be accomplished by known methods, such as centrifuging the device with ethanol in the lumen or soaking the device in ethanol. Experimentation suggests that it makes little difference whether prosthesis 10 is subjected to centrifugation with ethanol or whether prosthesis 10 is soaked in ethanol. Both processes are about equally effective in displacing air. As discussed below, other example wetting agents that may be used instead of or in addition to ethanol include lecithan and Zonyl™ FSO.

Ethanol is a poor medium for cells, however, so prosthesis 10 can be wetted with a second agent that displaces the ethanol and provides a growth medium for the cells. A growth medium is any medium that maintains the cells in a viable state during seeding. Experimentation indicates that a growth medium may also enhance cell retention after implantation. Plasma-Lyte® A and EBM-2™ are examples of second agents that can provide a growth medium. Either of these growth media can be followed by wetting with a blood centrifugation product, such as platelet-poor plasma or platelet-rich plasma, as will be described in greater detail below. Introduction of these agents may be achieved by, for example, centrifugation, soaking or other wetting methods. After the a blood centrifugation product has been in contact with luminal surface 14 for a period of time, which may be one to sixty minutes, or several hours, the a blood centrifugation product is drained off or otherwise removed, the suspension with cells can be introduced, and centrifugation can be performed to cause the cells to accumulate on the luminal surface.

Blood centrifugation products, such as platelet poor plasma, may be produced from the blood of the patient, which eliminates sterility and compatibility issues related to donor fluids. In general, blood centrifugation products are produced by centrifuging the blood to separate the blood into fractions, e.g., platelet-rich and platelet-poor fractions.

Blood is composed of variety formed elements or cells including, for example, red blood cells, white blood cells, and platelets dispersed in a fluid phase called plasma. The cell types differ in density, size and abundance and thus when blood is centrifuged different cell types settle out from the plasma phase at different rates. It can be appreciated that a wide variety of blood centrifugation products or fractions can be prepared by centrifugation depending on the magnitude and duration of centrifugal force applied as well as the temperature, pre-clotting prior to centrifugation, post-centrifugation conditions such as freezing, and other variables.

Blood centrifugation products can include for example, a platelet-poor plasma (PPP) where substantially, but not necessarily, all cells, including platelets, have settled out from the plasma, a platelet-rich plasma (PRP) where substantially all red and white blood cells have settled out from the plasma phase, but large number of platelets remain in the plasma phase, and a serum fraction where pre-clotted blood is subjected to centrifugation to remove substantially all cells from the plasma fraction and also soluble fibrinogen and soluble factors that associate with the fibrin clot. Blood centrifugation products can also include cellular fractions enriched in red blood cells such as packed red blood cell fractions, fractions depleted of red blood cells but enriched in white blood cells such as the buffy coat, or fractions enriched in platelets derived from plasmaphoresis.

An example device that is capable of producing a blood centrifugation product, such as PPP, is the Magellan™ separator device produced by Medtronic, Inc. The operation of the Magellan™ device to produce PPP is described in greater detail below. The structure and operation of the Magellan™ device is also described in the following documents, which are incorporated herein by reference in their entirety in Table 1.

TABLE 1

Table 1 lists U.S. patents that describe Magellan related centrifuge methods and devices for separating blood components.

| Pat. No. | Filing Date | Inventors | Title |
| --- | --- | --- | --- |
| 6,579,219 | Apr. 9, 2001 | Dolecek, et al. | Centrifuge bag and methods of use |
| 6,589,153 | Sep. 24, 2001 | Dolecek, et al. | Blood centrifuge with exterior mounted, self-balancing collection chambers |
| 6,589,155 | Apr. 9, 2001 | Dolecek | Miniaturized blood centrifuge having side mounted motor with belt drive |
| 6,596,180 | Apr. 9, 2001 | Baugh, et al. | System and method for the production of autologous platelet gel |
| 6,596,181 | Apr. 9, 2001 | Dolecek, et al. | Hard shell disposable reservoir having complex internal design for use in a centrifuge |
| 6,605,028 | Apr. 9, 2001 | Dolecek | Blood centrifuge having integral heating to control cellular component temperature |
| 6,610,002 | Apr. 9, 2001 | Dolecek | Method for handling blood sample to ensure blood components are isolated |
| 6,612,975 | Apr. 9, 2001 | Malcom, et al. | Blood centrifuge with an enhanced internal drive assembly |
| 6,719,901 | Apr. 9, 2001 | Dolecek, et al. | System for the production of an autologous thrombin |
| 6,790,371 | Apr. 9, 2001 | Dolecek | System and method for automated separation of blood components |
| 6,827,863 | Jun. 16, 2003 | Dolecek, et al. | Flexible centrifuge bag and methods of use |
| 6,887,371 | Mar. 25, 2003 | Dolecek | System for automated separation of fluid components |
| 6,899,813 | Dec. 17, 2003 | Dolecek, et al. | Method for the production of a blood component composition |
| 6,951,612 | Apr. 7, 2003 | Dolecek | Blood centrifuge having overhanging disposable blood container |

The Magellan™ device utilizes centrifugation to separate whole blood into the separate components. In contrast to other centrifugation devices, the Magellan™ device is capable of drawing off certain blood centrifugation products during centrifugation without stopping the device to remove portions of the product. The device includes two opposing chambers that are about an axial axis. During centrifuging, whole blood from the patient is delivered equally to the chambers, and more dense components of the blood pack towards the outer regions of each chamber. In this manner, the whole blood is separated into four main fluid sections of varying densities. The outermost section contains red blood cells, the next inner section contains white blood cells, PRP is found further towards the inner portion, and PPP is found as the innermost section of fluid. Each container includes ports located within each of these sections to draw off the desired fluid during centrifuging. Additionally, whole blood may be delivered through these ports during a continued operation, where the components of the blood are constantly being separated. The Magellan™ device, therefore, may produce a desired blood centrifuge product, e.g., PPP, faster, and with greater precision, than with alternative centrifuge devices and methods. Further, the Magellan™ device may produce a version of a desired blood centrifuge product, e.g., PPP, that is different from and potentially superior to versions of the blood centrifuge product produced by other means.

In other embodiments, other exemplary devices may produce a blood centrifugation product, such as PPP or platelet rich plasma (PRP). Table 2 lists documents that describe these devices and methods, of which all are incorporated herein by reference in their entirety in Table 2. In one example of a method differing from the Magellan™ device, PPP and PRP are produced in separate steps. First, anticoagulated whole blood centrifuged to form two liquid phases. The top phase is PRP, and the bottom phase is anticoagulated whole blood minus the PRP. The PRP may be gently drawn off and saved in a container. The remaining anticoagulated whole blood minus the PRP is further centrifuged at a much higher rate. This higher rate of centrifugation results in the red blood cells, white blood cells and platelets being spun out of the anticoagulated whole blood minus the PRP, thereby forming a pellet comprising cellular components. The resulting PPP is then decanted from the pellet and saved in a container.

TABLE 2

Table 2 lists U.S. patents that describe centrifuge methods and devices for separating blood components.

| Pat. No. | Filing Date | Grant Date | Title |
| --- | --- | --- | --- |
| 6,444,228 | Apr. 20, 1998 | Baugh, et al. | Autologous fibrin sealant and method for making the same |
| 6,582,350 | Apr. 9, 2001 | Dolecek | Centrifuge container having curved linear shape |
| 6,793,828 | May 8, 2003 | Dolecek, et al. | Method of separating and collecting components from a fluid |
| 6,830,762 | Jun. 18, 2002 | Baugh, et al. | Autologous fibrin sealant and method for making the same |
| 6,890,728 | Apr. 4, 2002 | Dolecek, et al. | Methods of isolating blood components using a microcentrifuge and uses thereof |
| 6,942,639 | Apr. 9, 2001 | Baugh, et al | Autologous platelet gel delivery system |
| 6,942,880 | Apr. 9, 2001 | Dolecek | Autologous platelet gel having beneficial geometric shapes and methods of making the same |
| 6,982,038 | Jan. 10, 2003 | Dolecek, et al. | Centrifuge system utilizing disposable components and automated processing of blood to collect platelet rich plasma |

The wetting agents described above are for purposes of illustration, and the invention is not limited to those wetting agents. A fluorosurfactant, Zonyl® FSO, commercially available from DuPont, is an example of another wetting agent. Another exemplary wetting agent is phosphatidylcholine, which has a common name of lecithin and which is widely available from a number of suppliers. Lecithin is a natural surfactant emulsifier. It may be possible to immerse a prosthesis in an organic solution containing lecithin and let the solvent evaporate, leaving behind a lecithin surfactant-like coating.

By applying one or more wetting agents, air in prosthesis 10 can be displaced. Once the air is displaced, luminal surface 14 can be conditioned for seeding without reintroducing air. It is possible, however, that air may be reintroduced into luminal surface 14 by handling of prosthesis 10, making seeding less effective. In particular, compressing and stretching of prosthesis 10, or bending of prosthesis 10, can result in reintroduction of air.

Sleeve 126 provides protection against compressing, stretching and bending of prosthesis 10, and thereby reduces the risk that handling will reintroduce air onto luminal surface 14 or the bulk of prosthesis 10. Sleeve 126 fits snugly over prosthesis 10 and is substantially more rigid than prosthesis 10. As prosthesis 10 is placed into or removed from a centrifuge, or is otherwise handled, such as removing the prosthesis from the centrifuge tube, bringing the prosthesis into the operating field for implantation, and/or handling the prosthesis during implantation, sleeve 126 helps prosthesis 10 retain its shape. At the time of implantation, prosthesis 10 may be extracted from sleeve 126, and sleeve 126 may be discarded. In some cases, prosthesis 10 can be maintained inside protective sleeve 126 during implantation, with sleeve 126 removed near the conclusion of implantation, e.g., just prior to or just after cross-clamp release. Protective sleeve 126 can reduce the risk or seeded cell loss during implantation, due to factors such as bending, drying or cell dislodgement.

Figure 16:
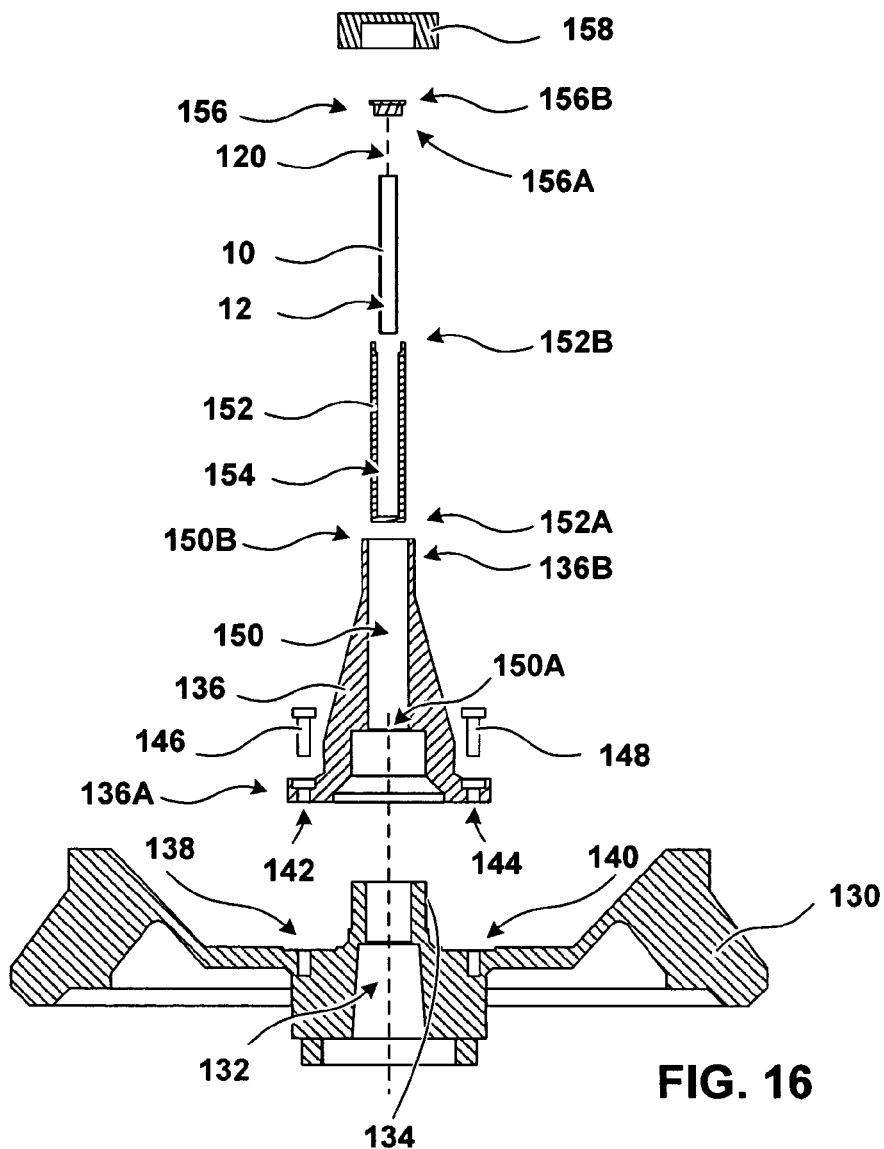
FIG. 16 is a cross-sectional exploded view of an exemplary vertical centrifugation apparatus.
Figure 17:
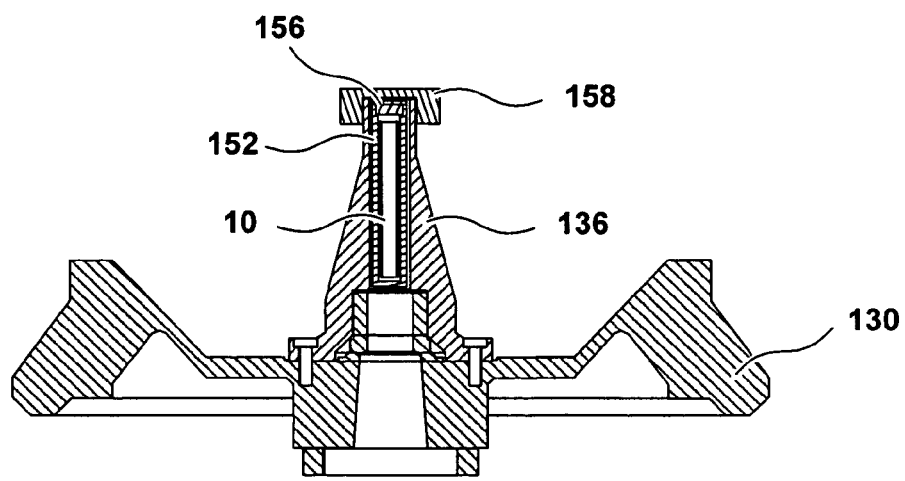
FIG. 17 is a cross-sectional assembled view of the exemplary vertical centrifugation apparatus depicted in FIG. 16.
Figure 18:
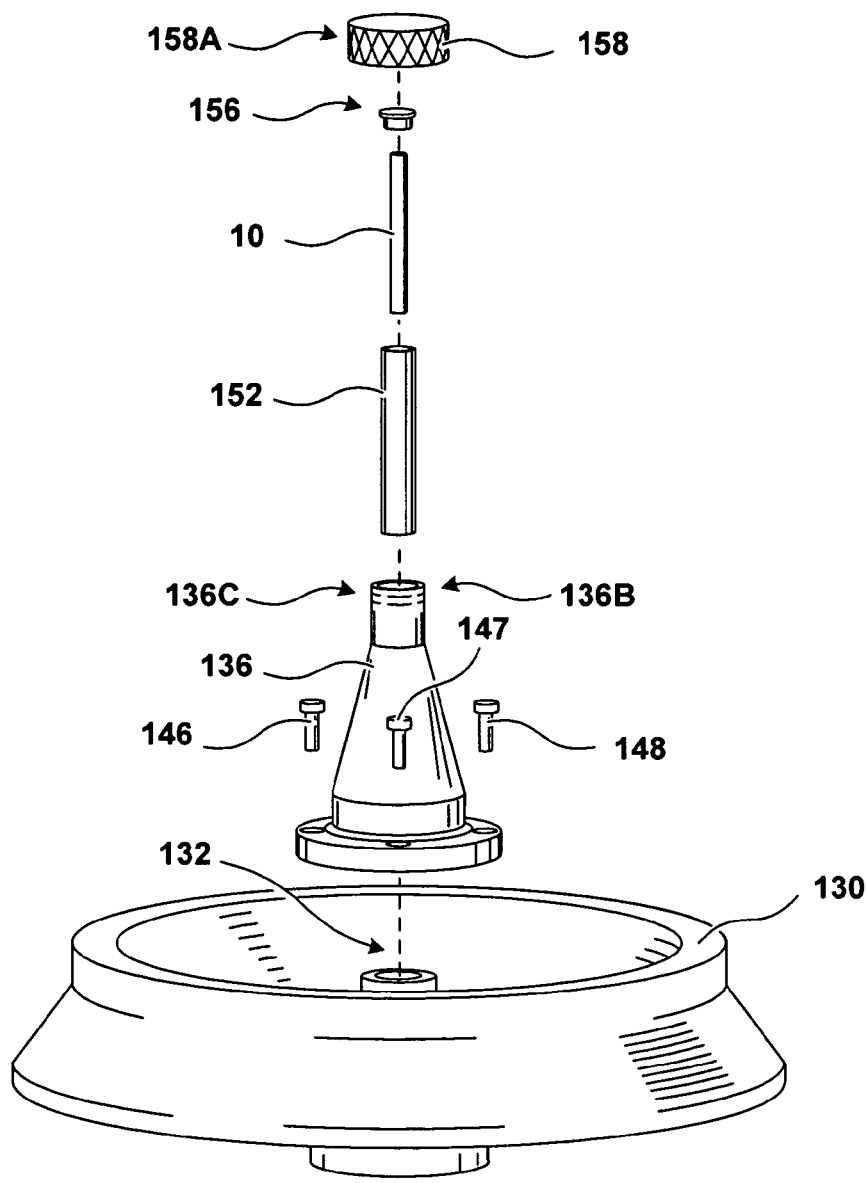
FIG. 18 is a perspective exploded view of the exemplary vertical centrifugation apparatus depicted in FIGS. 16 and 17.
Figure 19:
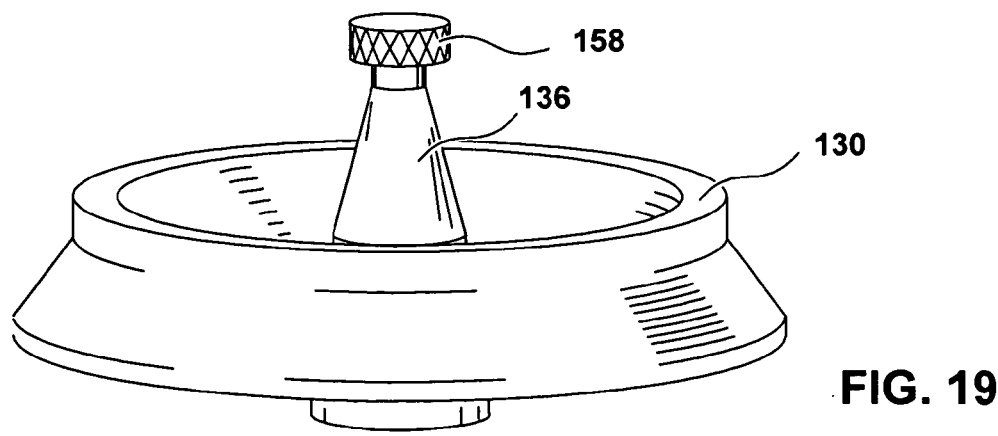
FIG. 19 is a perspective assembled view of the exemplary vertical centrifugation apparatus depicted in FIGS. 16, 17 and 18.

FIGS. 16-19 are views of an illustrative apparatus for axial centrifugation of prosthesis 10. FIG. 16 is an exploded cross-sectional view showing the components, FIG. 17 is a cross-sectional view showing the components assembled and ready for centrifugation, FIG. 18 is a perspective exploded view, and FIG. 19 is a perspective assembled view. The apparatus depicted in FIGS. 16-19 can be used with a tabletop or laboratory centrifuge (not shown), which can be set up in an operating room. An example of a centrifuge that can accommodate the apparatus shown in FIGS. 16-19 is an Eppendorf Model 5416B commercially available from Gerätebau Eppendorf GmbH of Engledorf, Germany.

Rotor 130 is the element that is mechanically coupled to, and that is directly rotated by, the centrifuge. An exemplary rotor for the Eppendorf Model 5416B centrifuge is a fixed-angle rotor for microcentrifuge tubes, Type 16 F 24-11, Part No. 22 63 220-5, commercially available from Gerätebau Eppendorf GmbH of Engledorf, Germany. The invention is not limited to this particular centrifuge or rotor. Such a rotor may include angular receptacles to receive Eppendorf tubes or other items. During axial centrifugation, it may be desirable to fill the receptacles to reduce noise.

Rotor 130 may be configured to support longitudinal and axial centrifugation. Rotor 130 may be constructed from a durable material such as aluminum or other metal, and can be constructed to support rotation at a range of angular velocities. The rotor model mentioned above is rated to 15,000 rpm, but typical lab centrifuge may drive rotor 130 to at higher angular velocities, e.g., around 18,000 rpm. The axis of rotation 132 of rotor 130 passes through rotor spindle 134.

As shown in FIG. 16, rotor spindle 134 lacks elements to hold and support centrifugation of a prosthesis 10. In addition, spindle 134 is too small to accommodate a prosthesis having a length of four to fifteen centimeters, which are typical lengths for small diameter vascular prostheses. Accordingly, an adapter 136 can hold and support prosthesis 10 during axial centrifugation of prosthesis 10.

Adapter 136 is configured to mate with rotor 130, fitting over spindle 134. Consequently, adapter 136 is configured to mate with rotor 130 proximate to axis of rotation 132, and as shown in FIGS. 16 and 18, axis of rotation 132 passes through adapter 136. In some embodiments of the invention, spindle 134 can be machined to better accommodate the mating. In the event rotor 130 had a configuration different from that shown in FIGS. 16-19, adapter 136 may likewise have a different configuration, to mate with rotor 130.

As shown in FIG. 16, rotor 130 can be machined to include receptacles 138 and 140, which correspond respectively to holes 142 and 144 on a base 136A of adapter 136. Fixation mechanisms 146 and 148, such as screws, can be used to secure adapter 136 to rotor 130 via holes 142 and 144 and fixation mechanisms 146 and 148. Although FIG. 16 depicts two sets of holes and fixation mechanisms, the invention supports any number of sets of holes and fixation mechanisms. FIG. 18, for example, depicts an arrangement that could support four equidistant sets of holes and fixation mechanisms, with fixation mechanisms 146, 147 and 148 being visible. In addition, adapter 136 may be secured to rotor 130 with materials or apparatus other than what is shown in FIGS. 16 and 18, such as bolts, adhesive, clasps, locks, clamps, welds, and the like.

Adapter 136 may be constructed from a durable material such as aluminum or other metal, and can be constructed to support rotation up to the same angular velocity as rotor 130. Adapter 136 can have any dimension. As depicted in FIG. 16, adapter 136 can extend vertically about 6.73 centimeters. Base 136A of adapter 136 can be substantially circular, with an outer diameter of about 5.19 centimeters. Upper portion 136B of adapter 136 can be substantially circular, with an outer diameter of about 1.8 centimeters. For a longer prosthesis, a taller adapter with a wider base can be used. It is believed that a tall adapter could be used to accommodate a prosthesis up to 20 cm. Similarly, adapter 136 and various features thereof can be shortened, widened, narrowed or otherwise configured to receive a particular implantable medical device.

Adapter 136 includes a chamber 150 that can receive prosthesis 10, as well as other apparatus, as discussed below. Chamber 150 depicted in FIG. 16 can be substantially cylindrical, with a length of about 4.85 centimeters, and a diameter of about 0.96 centimeter. The height of chamber 150 extends substantially lengthwise in the direction of axis 132, and the radius of chamber 150 extends substantially perpendicularly from axis 132. Chamber 150 need not be an exact cylinder, but may include tapered or ridged walls, for example, or may be prism-shaped. Adapter 136 is configured such that chamber 150 defines a closed end 150A and an open or openable end 150B.

It may not be convenient to attach adapter 136 to rotor 130, and remove adapter 136 from rotor 130, with each centrifugation. As depicted in FIGS. 16 and 17, adapter 136 is configured to be firmly affixed to rotor 130.

A sealable container such as tube 152 can be used to aid insertion of prosthesis 10 into chamber 150 of adapter 136, and to aid removal as well. When suspension and cells are introduced into lumen 12 of prosthesis 10, tube 152 contains and reduces the risk of spillage of the suspension and cells. Tube 152, which may also be referred to as a "centrifuge tube 152," can offer the additional advantage of protecting prosthesis 10 from risks associated with handling, as described above.

Centrifuge tube 152 can be substantially cylindrical and can be constructed from a durable material such as polycarbonate or metal. As shown in FIG. 16, tube 152 has a closed end 152A and an open end 152B. The outer diameter of tube 152 can be about 0.95 centimeter, slightly smaller than the bore of chamber 150. Centrifuge tube 152 includes an inner chamber 154, which is substantially cylindrical. Exemplary dimensions of centrifuge tube inner chamber 154 are 4.6 centimeters in length, and 0.60 centimeters in diameter. Tube inner chamber 154 receives prosthesis 10. Although not depicted in FIGS. 16 and 17, centrifuge tube inner chamber 154 can also receive prosthesis 10 inside protective sleeve 126, as shown in FIG. 15.

A sealing device, in the form of a plug 156, is configured to seal prosthesis 10 inside centrifuge tube 152. Plug 156 can be formed from a durable material such as aluminum or other metal or polycarbonate or polymer or plastic. Plug 156 is configured to seal open end 152B of tube 152, and the plug may consist of a cap and sealing septum. As depicted in FIGS. 16 and 17, most of the body 156A of plug 156 is configured to seat inside tube inner chamber 154, with a top lip portion 156B remaining outside inner chamber 154, thereby an access structure for ready removal of plug 156 from open end 152B of centrifuge tube 152. The open end of tube 152 can be configured to receive plug 156. When prosthesis 10 is placed inside centrifuge tube 152 and plug 156 is seated in tube 152, prosthesis 10 and any material placed inside prosthesis 10 are prevented from being ejected from tube 152 during centrifugation.

A cap 158 is configured to mate securely but removably to adapter 136. Cap 158, which can be formed from a durable material such as aluminum, can mate with adapter 136 in any several ways. For example, upper portion 136B of adapter 136 can be machined to include screw threads 136C, as shown in FIG. 18, which mate with matching grooves (not shown) in cap 158, allowing cap 158 to be "screwed on" to adapter 136. The exterior surface of cap 158 can be provided with knurling 158A or other structures that assist a firm grip, enabling a person to secure cap 158 to, and remove cap 158 from, adapter 136 without a tool. Cap 158 can be substantially cylindrical, with length of 0.64 centimeters and a diameter of 1.91 centimeters.

FIG. 17 provides an assembled cross-sectional view of the apparatus shown in an exploded view in FIG. 16. As depicted in FIG. 17, cap 158 is configured to bear against plug 156 when cap 158 is secured to adapter 136. Cap 158 may include, for example, a gum rubber disk or O-ring that bears against plug 156, holding plug 156 in place and preventing leakage. In this way, securing cap 158 to adapter 136 fully seats plug 156 in tube 152.

When centrifuge tube 152 is placed inside chamber 150 of adapter 136, and cap 158 is secured to adapter 136, tube 152 is prevented from being ejected from adapter 136 during centrifugation. As described above, plug 156 prevents prosthesis 10 and any material placed inside prosthesis 10 from being ejected from tube 152 during centrifugation. In this way, cap 158 and plug 156 cooperate to prevent prosthesis 10 and any material placed inside prosthesis 10 from being ejected during centrifugation. When the apparatus is assembled as shown in FIGS. 17 and 19, axis of rotation 132 is substantially collinear with longitudinal axis 120 of prosthesis 10.

The apparatus shown in FIGS. 16-19 is exemplary, and the invention is not limited to the apparatus shown. For example, the apparatus shown in FIGS. 16-19 may be unable to accommodate prostheses longer than a certain length or wider than a certain diameter. Adapter 136 and tube 152 can be elongated, shortened, widened or narrowed to accommodate implantable medical devices of other dimensions. It is believed that adapter 136 can be as short as desired, but should not be overly tall, so as not to introduce a rotational inertia that could affect smooth centrifugation. It is believed that adapter 136 could be extended to about 22 centimeters, enabling adapter 136 to accommodate a prosthesis about 20 centimeters long.

In addition, the apparatus shown in FIGS. 16-19 holds prosthesis 10 vertically during axial centrifugation, but an apparatus that holds prosthesis 10 horizontally or on a slant during axial centrifugation is also contemplated. Further, it is contemplated that "axial centrifugation" encompasses centrifugation that is substantially axial. In other words, it is contemplated that some degree of longitudinal centrifugation may occur. It is believed, however, that as the component of longitudinal centrifugation increases, the effectiveness of seeding decreases. The best results would be obtained with centrifugation that is mostly or entirely axial.

Figure 20:
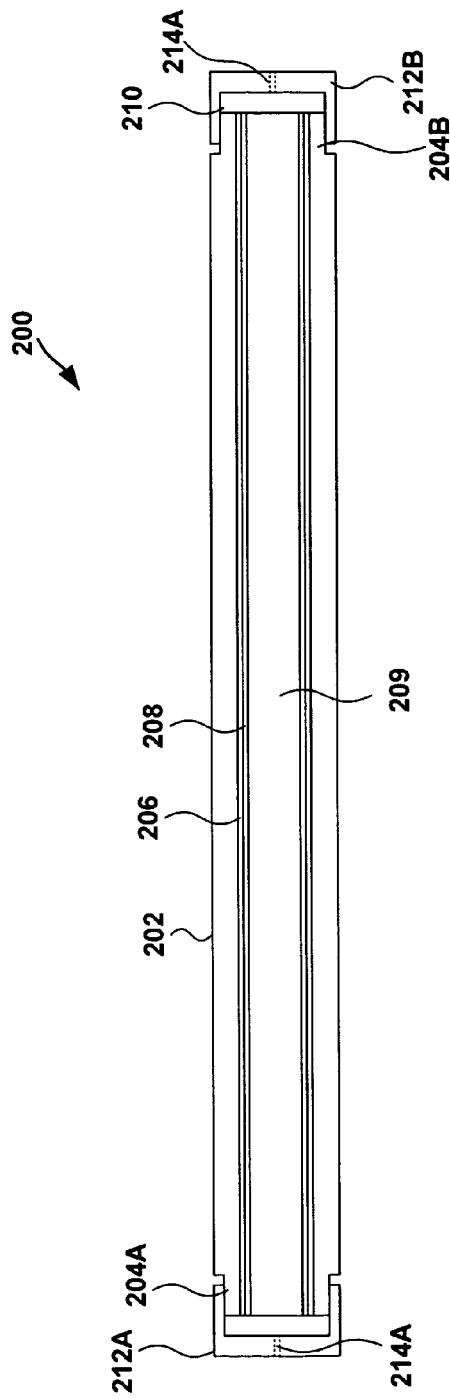
FIG. 20 is a cross-sectional view of an example tube containing a protective sleeve and vascular prosthesis for centrifugation.

FIG. 20 is a cross-sectional view of an example centrifuge tube containing a protective sleeve and vascular prosthesis. The tube, protective sleeve and vascular prosthesis may be substantially similar to centrifuge tube 152, sleeve 126 and prosthesis 10 described above with reference to FIGS. 1-19. Further, the tube and protective sleeve of FIG. 20 may be used for substantially the same purpose as tube 152 and sleeve 126, e.g., to facilitate handling and axial centrifugation of a vascular prosthesis during cell seeding.

As shown in FIG. 20, a prosthesis handling system 200 includes a tube 202, which may be referred to as the "centrifuge tube 202," a protective sleeve 206, and a vascular prosthesis 208. System 200 may protect prosthesis 208 during cell seeding. Prosthesis 208 may be substantially similar to prosthesis 10 described above, e.g., may be made of ePTFE. As described above with reference to prosthesis 10, prosthesis 208 preferably, but not necessarily, has been rubbed to create recesses on its luminal surface to facilitate cell seeding.

In the illustrated embodiment, system 200 also includes tube caps 212A and 212B (collectively "tube caps 212"), and centrifuge tube 202 includes flanges 204A and 204B (collectively "flanges 204") at respective ends of the tube. Tube caps 212 may interact with flanges 204 to, for example, facilitate holding or sealing sleeve 206 and prosthesis 208 within a lumen of centrifuge tube 202.

In the illustrated embodiment, each of tube caps 212 includes a respective one of delivery holes 214A and 214B (collectively "delivery holes 214"). Septa 210A and 210B (collectively "septa 210") seal respective ends of tube 202, and are secured on the tube by respective tube caps 212. Septa 210 may be penetrable such that delivery holes 214 provide access to the interior or lumen of tube, and particularly to a lumen 209 of prosthesis 208, as will be described in greater detail below.

System 200 is shown with all components; however, protective sleeve 206 and vascular prosthesis 208 may only be placed within centrifuge tube 202 during a cell seeding procedure. Further, although tube 202 is illustrated as having two open ends, with respective caps 212, flanges 204, septa 210 and delivery holes 214, the invention is not so limited. For example, in some embodiments, only one of caps 212 includes a delivery hole 214. In other embodiments, only one end of tube is capable of being opened, and system 200 includes only a single cap, flange and delivery hole.

Centrifuge tube 202 retains protective sleeve 206 and prosthesis 208 during a cell seeding process, which may include centrifuging. Centrifuge tube 202 may be a cylindrical, rigid tube constructed of a metal alloy, polymer, composite, or other similar type of material. An exemplary material for construction of centrifuge tube 202 is polycarbonate. Protective sleeve 206 is also rigid or semi-rigid, and the sleeve may be constructed of a polymer capable of supporting or protecting vascular prosthesis 208 during handling attendant to the cell seeding process and implantation. For example, protective sleeve 206 may be constructed of PTFE. In some embodiments, a wire or wire mesh may be formed in or placed around the outer diameter of protective sleeve 206 to provide structural support to the sleeve.

Septa 210 seal the ends of tube 202 to prevent material, such as cells, from escaping seeding device 200 during the cell seeding process. Septa 210 contact the edges of flanges 204, which may be of slightly smaller outer diameter than the outer diameter of tube 202. Tube caps 212 secure septa 210 by interaction with flanges 204. The caps and flanges may provide a friction fit, or may include helical grooves, ridges, or other features that mate to secure caps 212 to tube 202. For example, tube caps 212 may be screwed on to tube 202.

Delivery holes 214 allow a needle attached to a syringe, or the like, to pierce septum 210, which may allow material to be added to or removed from lumen 209 of prosthesis 208, as will be described in greater detail below. Septa 210 may be constructed of a self-sealable material, such as silicone, medical-grade gum rubber, BUNA-N rubber, or Viton® fluoroelastomer, the latter of which is commercially available from DuPont Performance Elastomers. Similar to commonly used liquid drug vials, septa 210 may allow a needle to penetrate the septum, and self-seal once the needle is removed. Septa 210 may be penetrated multiple times and still act as a barrier to liquid. The diameter of delivery holes 214 is generally between approximately 0.5 millimeters and approximately 20 millimeters. More specifically, the diameter of delivery holes 214 may be between approximately 1 millimeter and approximately 2 millimeters.

Protective sleeve 206 may generally perform substantially the same functions as sleeve 126 described above with respect to supporting and protecting a prosthesis during handling associated with a cell-seeding process and implantation. An inner diameter of sleeve 206 may be sized to substantially conform to an outer diameter of prosthesis 208, e.g., to snugly but removably hold the prosthesis within a lumen of the sleeve. The length of sleeve 206 may be slightly shorter or longer than, or may be substantially the same as, the length of prosthesis 208, as desired for handling the sleeve and prosthesis, and insertion and removal of the prosthesis from the sleeve.

As examples, protective sleeve 206 may have an inner diameter between approximately 1 millimeter, e.g., in very small diameter vascular prosthesis applications, and approximately 40 millimeters, e.g., in large AAA grafts and heart valves. In some embodiments, the inner diameter of sleeve 206 is between approximately 4 millimeters and approximately 8 millimeters. The outer diameter of protective sleeve 206 may be between approximately 1.5 millimeters and approximately 40.5 millimeters and, in some embodiments, may be between approximately 4.5 millimeters and approximately 8.5 millimeters. The length of protective sleeve 206 may be between approximately 1 centimeter and approximately 80 centimeters. Again, the dimensions of sleeve 206 may largely depend of the dimensions of prosthesis 208.

As examples, centrifuge tube 202 may generally have an inner diameter between approximately 1.5 millimeters and approximately 40.5 millimeters. In some embodiments, the inner diameter of tube 202 is between approximately 5 millimeters and approximately 10 millimeters. Generally, the outer diameter of tube 202 is between approximately 2 millimeters and approximately 45 millimeters and, in some embodiments, may be between approximately 5.5 millimeters and approximately 10.5 millimeters. The length of tube 202 may be between approximately 1 centimeter and approximately 80 centimeters. The dimensions of tube may also largely depend of the dimensions of prosthesis 208, which in some applications, such as AAA grafts and heart valves, can be quite large. As can be seen from the example dimensions system 200 may, for example, accommodate prostheses with lengths ranging from approximately 1 centimeter to approximately 80 centimeters.

Figure 21:
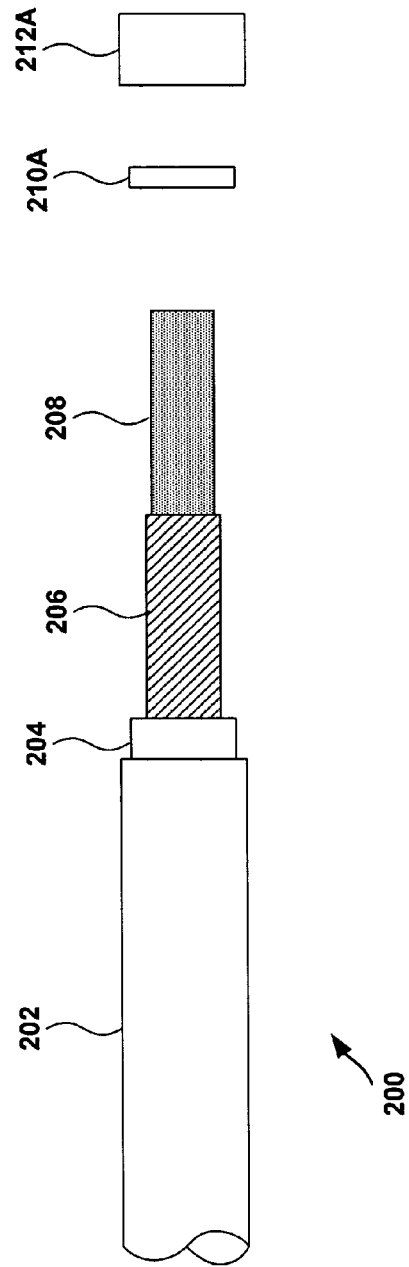
FIG. 21 is a side exploded view the example tube of FIG. 20.

FIG. 21 is a side exploded view of prosthesis handling system 200. In the view shown in FIG. 21, protective sleeve 206 is slid partially out of centrifuge tube 202, and vascular prosthesis 208 is slid partially out of protective sleeve 206. Septum 210A may be separate from tube cap 212A or mounted within the tube cap.

In some embodiments, vascular prosthesis 208 may be inserted within protective sleeve 206 before the protective sleeve is inserted into tube 202. Similarly, protective sleeve 206 may be removed from centrifuge tube 202 while vascular prosthesis 208 remains within the protective sleeve. However, the order of insertion and removal may be different in other embodiments.

Figure 22:
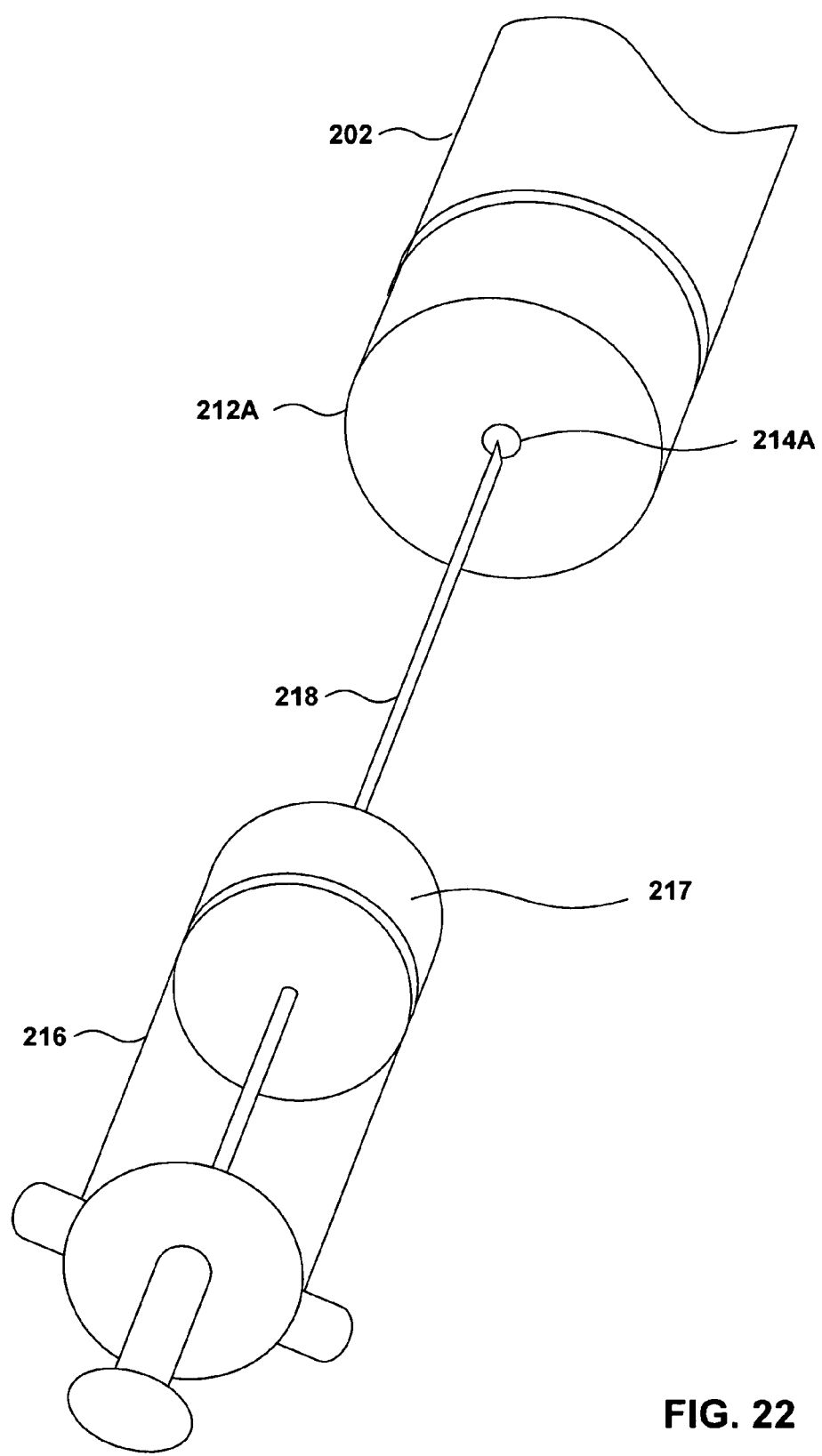
FIG. 22 is a perspective view of a syringe injecting material into a lumen of a vascular prosthesis within the example tube of FIGS. 20 and 21.

FIG. 22 is a perspective view of a syringe 216 injecting a material 217 into lumen 209 (FIG. 20) of vascular prosthesis 208 (FIG. 20) while the prosthesis is located within tube 202. As shown in FIG. 22, syringe 216 is loaded with material 217, e.g., patient endothelial cells, for injection into lumen 209. A needle 218 attached to syringe 216 pierces septum 210A (not shown) through delivery hole 214A of tube cap 212A. Once material 217 has been introduced into lumen 209, needle 218 is removed from delivery hole 214A and septum 210A self-seals. In some cases, material 217 may be later removed from lumen 219 in the same manner, e.g., via delivery hole 214 using syringe 216 and needle 218. In some cases, a needle may be inserted through the opposite end septum to alleviate vacuum and/or pressure buildup in the graft/tube assembly during removal and addition of fluids through the opposing septum.

In other embodiments, different piercing objects or delivery mechanisms may be used to introduce and remove materials during the seeding process. Materials that may be injected and removed from lumen 209 via delivery hole 214A and septum 210 at different times throughout a cell-seeding process include: wetting agents, such as ethanol; growth media, such as Plasma-Lyte® A, EBM-2™, and one or more blood centrifugation products, such as PPP; and patient endothelial cells in suspension. The use of these materials in a cell seeding process will be described in greater detail below.

Figure 23:
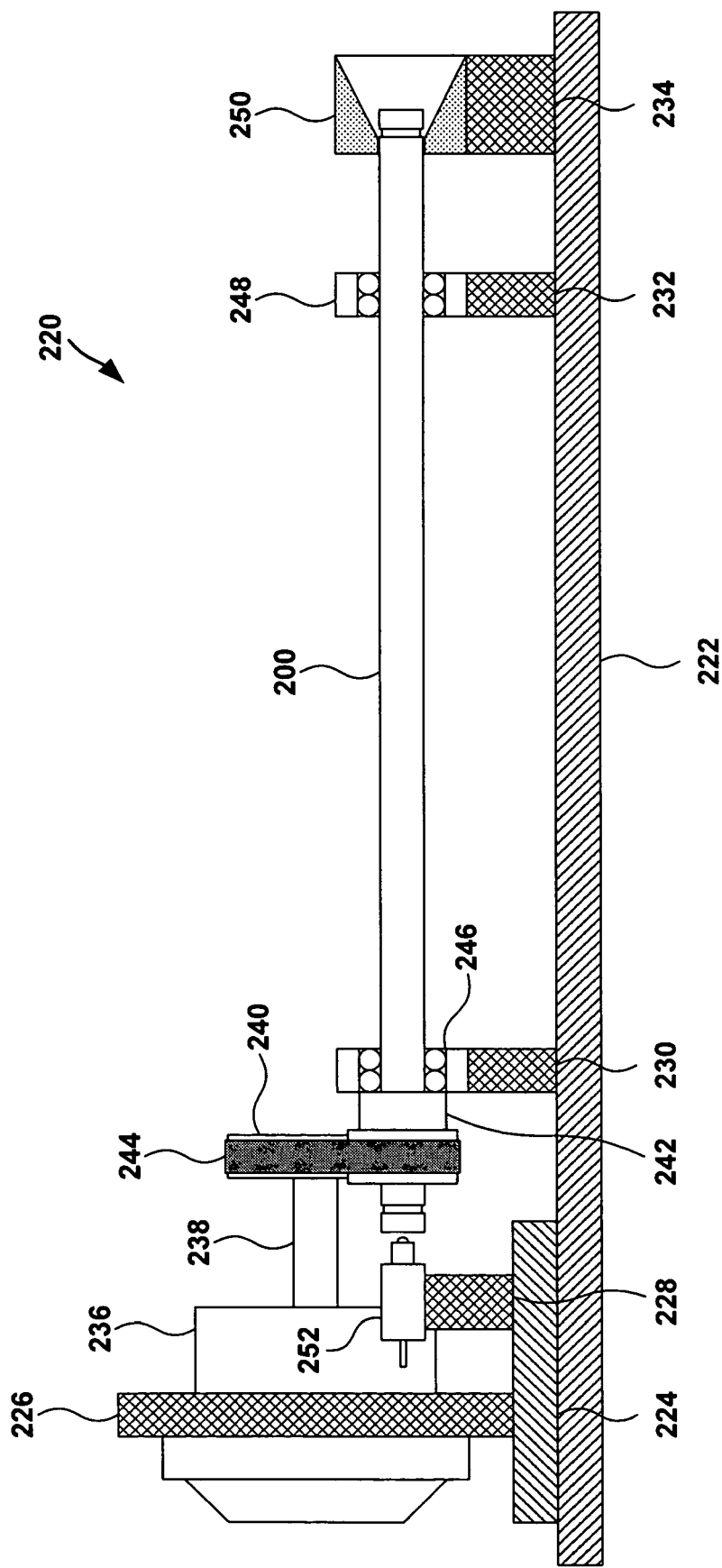
FIG. 23 is a side, partial cross-sectional, schematic view of an example horizontal centrifuge used to seed cells in a vascular prosthesis.

FIG. 23 is a side, partial cross-sectional, schematic view of an example horizontal centrifuge 220 used to seed cells in a vascular prosthesis. As shown in FIG. 23, prosthesis handling system 200 may placed within horizontal centrifuge 220. Centrifuge 220 includes mounting plate 222, motor block 224, motor mount 226, and motor 236. Motor 236 is coupled to and rotates a shaft 238, which in turn rotates a coupled rotor 240, and a belt 244 that mounted on the rotor. Belt 244 is also mounted on and rotates a balanced stainless steel tube 242 that acts as the centrifuge 'rotor' for the system 200, which is inserted inside of the rotor. Accordingly, system 200 and centrifuge tube 202 are sized and configured to be frictionally by the rotor tube 242 of the centrifuge, such that the rotor tube may rotate the centrifuge tube. System 200 is placed substantially horizontally within and received by ball bearings 246 and 248, and drum 242. The ball bearings are mounted atop bearing mounts 230 and 232, respectively. An insertion block 250 is mounted on top of a block 234 and directs centrifuge tube 202 during the substantially horizontal insertion into centrifuge 220. When system 200 is inserted into centrifuge 220, relatively rigid tube 202 allows the relatively elastic prosthesis 208 therein to be rotated, and protects the prosthesis 208 from the forces imparted by centrifuge 220 during centrifugation. Caps 212 and septa 210 prevent the prosthesis and fluids from being ejected from centrifuge tube 202 during centrifugation.

Like the substantially vertical centrifuge discussed above with reference to FIGS. 16-19, centrifuge 220 applies substantially axial centrifugation to prosthesis 208 within tube 202. In other words, the axis of rotation of system 200 within centrifuge 220 is substantially collinear with the longitudinal axis of prosthesis 208. However, unlike the above-described centrifuge, which orients a prosthesis in a substantially vertical position, centrifuge 220 positions system 200, and prosthesis 208 therein, in a substantially horizontal orientation during centrifugation.

A substantially horizontal orientation during centrifugation may allow relatively long prostheses 208 and systems 200 to be centrifuged without experiencing the rotational inertia that could affect smooth centrifugation if such systems were centrifuged vertically in the manner described above with reference to FIGS. 16-19. Further, a horizontal orientation may reduce the effect of gravity on suspended endothelial cells within lumen 209 during centrifugation. In particular, in a vertical position used in FIG. 16, some cells may concentrate at the lower portions of vascular prosthesis 208 and the cells may not disperse evenly throughout the length of the prosthesis. Although depicted in FIG. 23 as a horizontal orientation, centrifuge 220 may alternatively spin system 200 in a "tilted" orientation, e.g., slightly less than completely horizontal. A tilted orientation may allow air or any other gases within system 200 to collect at the end of tube 202 during centrifugation, where they are less likely to "de-wet" prosthesis, or otherwise negatively affect the cell-seeding process.

Motor 236 may rotate at speeds that can generate between approximately 1 g and approximately 10,000 g at the luminal surface of vascular prosthesis 208. In some embodiments, motor 236 may rotate at speeds which generate between approximately 250 g to about approximately 500 g of acceleration at the luminal surface of prosthesis 208. These forces may be applied between approximately 1 and 10 minutes to seed the cells within prosthesis 208. Five minutes of centrifuging at 250 g may be appropriate to successfully adhere the cells to the luminal surface of prosthesis 208. Electronic circuitry or a computing device may control the operation of centrifuge 220, and may do so according to user input received via a user interface. Programming can allow for acceleration to happen gradually, which protects endothelial cells from dangerous shear forces. Additional safety programming and electronics are also capable of detecting rotor imbalance, and allow for emergency shut down in such instances.

Once the centrifugation is complete, centrifuge 220 may eject system 200 from the centrifuge. Ejector 252 is a device that pushes centrifuge tube 202 out of centrifuge 220 so that a user can retrieve prosthesis 208 for implantation. Ejector 252 may be a spring loaded mechanism or linear actuator that moves system 200 out of centrifuge 220.

In some embodiments, centrifuge 220 may include an environment control system to adjust the temperature of system 200 during the seeding process or monitor the humidity of the system. In other embodiments, centrifuge 220 may employ different mechanisms to spin centrifuge tube 202 about the longitudinal axis and force the cells against the interior luminal wall of prosthesis 208.

Figure 24:
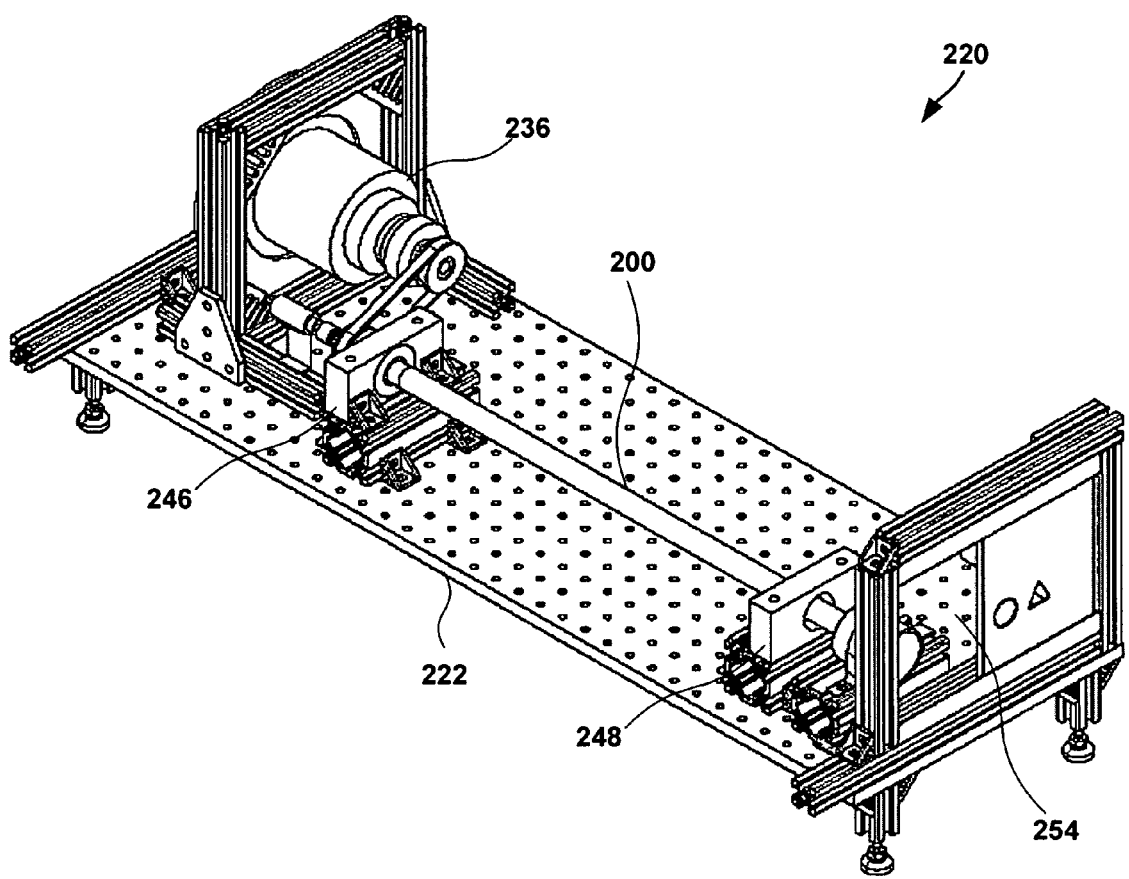
FIG. 24 is a prospective view of the example horizontal centrifuge of FIG. 23.

FIG. 24 is a perspective view of centrifuge 220. As shown in FIG. 24, system 200 is placed within centrifuge 220, through an opening 254. The axial positions of bearing mounts 230 and 232, and block 234, within centrifuge 220 may be adjusted to adjust the positions of corresponding bearings 246 and 248, as well as insertion block 250. Additionally or alternatively, centrifuge 220 may be configured to receive systems of varying diameters. In this manner, centrifuge 220 may be configured to handle vascular prosthesis of varying sizes. In some embodiments, centrifuge 220 may be capable of housing two or more systems 200 such that multiple prostheses may be seeded with cells.

Figure 25:
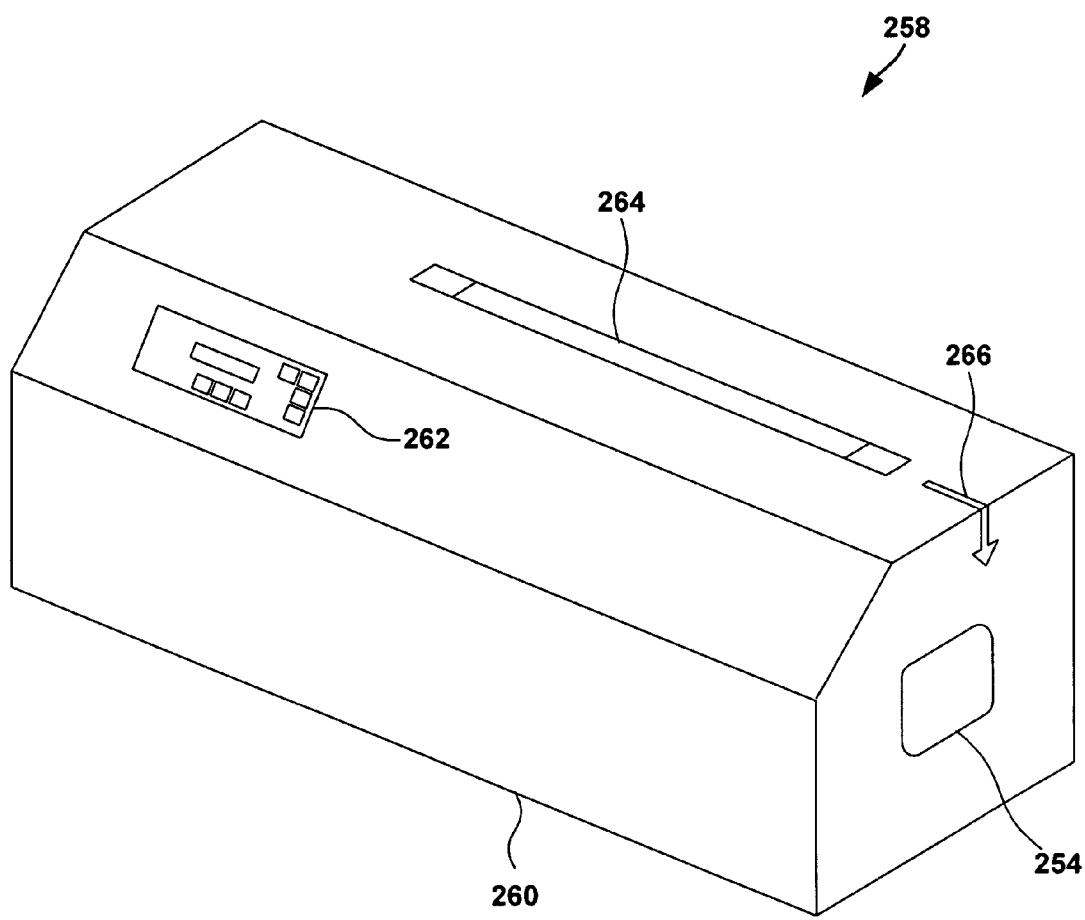
FIG. 25 is a prospective view of an example housing for the horizontal centrifuge of FIGS. 24 and 25.

FIG. 25 is a perspective view of an example housing 258 for a horizontal centrifuge, such as centrifuge 220 of FIGS. 23 and 24. Housing 258 includes opening 254 and a casing 260. A user interface 262 includes multiple buttons and a display so that a user can correctly configure centrifuge settings before centrifuging prosthesis 208. These settings may include spin duration, rotational speed, or desired radial force. In some embodiments, temperature or humidity may be controlled as well.

Graphic 264 indicates that system 200 is to be placed in the direction of arrow 266, through opening 254. Housing 258 may be designed for placement in small areas and easy operation by users with limited training or experience. Centrifuge 220 may even be capable of entering into a holding mode, in which the centrifuge periodically rotates seeding device 200 after the seeding spin until the user removes system 200 from housing 258. The entire system may also be situated on a cart for easy transport into and out of operating rooms. An exemplary centrifugation system usable for the purposes described with reference to FIGS. 20-25 is the Axial Centrifugation Cell Seeding System (ACCSS™) developed by Medtronic, Inc., of Minneapolis, Minn.

Figure 26:
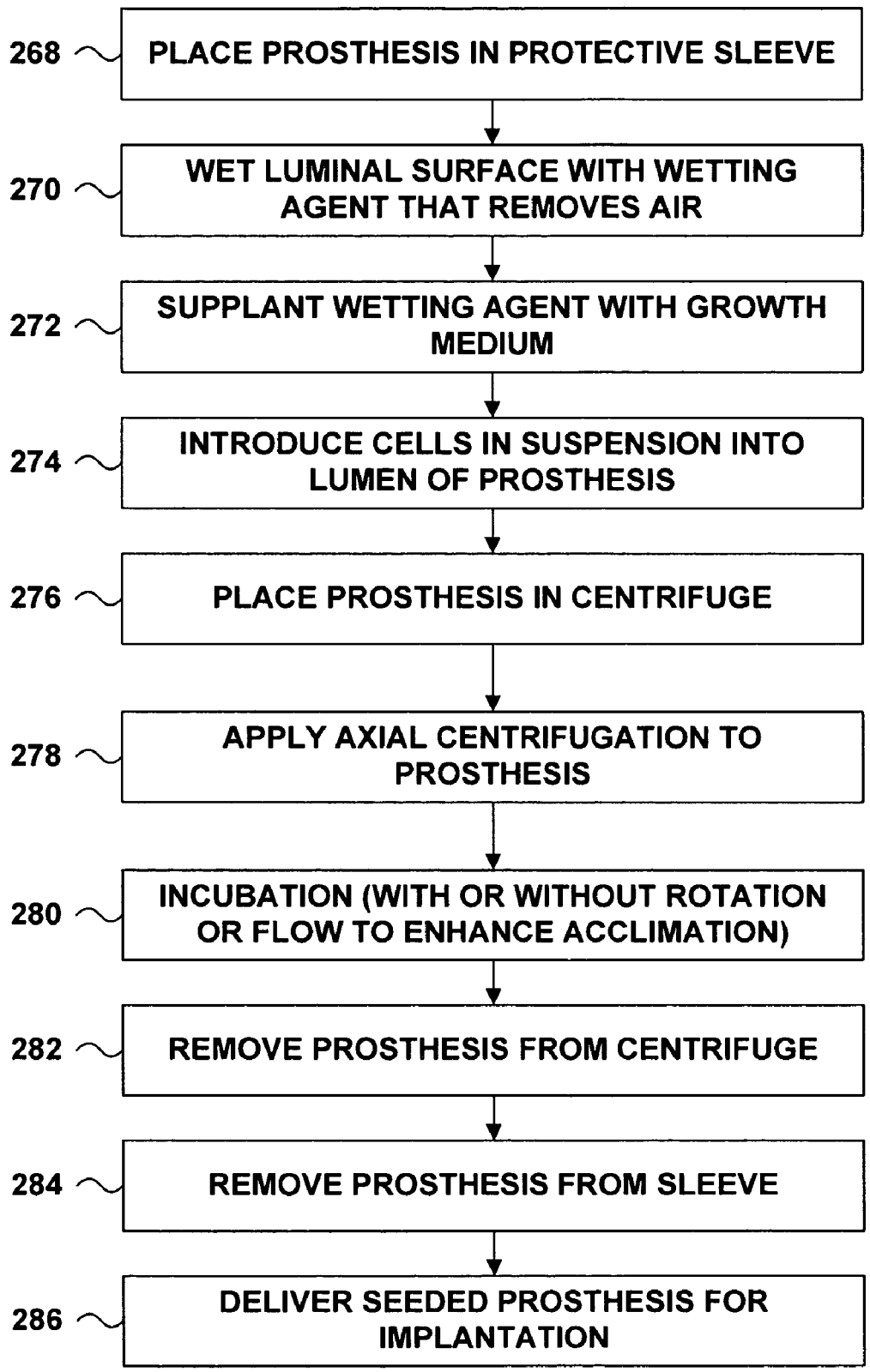
FIG. 26 is a flow diagram illustrating an example cell seeding technique.

FIG. 26 is a flow diagram illustrating an example seeding process. Optionally, prosthesis 10, 200 can be prepared for implantation by insertion into a protective sleeve 126, 206, as shown in FIGS. 15 and 21 (268). The sleeve provides protection against difficulties associated with handling the prosthesis. In addition, the prosthesis and sleeve can be loaded into an element such as tube 152, 202, which may provide further protection.

Optionally, one or more wetting agents (270), such as ethanol, can be introduced into lumen 12, 209 of the prosthesis to displace air inside the lumen. Wetting may take place in several stages, with later wetting agents supplanting earlier wetting agents. In various embodiments, wetting may occur prior to, during, and/or after insertion of the prosthesis into the sleeve and tube. In some embodiments, the prosthesis, sleeve, and centrifuge tube are pre-assembled together as one unit and provided in sterile package to an operating room for a seeding and implantation procedure. In such embodiments, wetting fluid, growth media, preparation media, a blood centrifugation product, and endothelial cells may be added and removed from the unit in a step-wise process using syringes via septa of the unit.

One or more of the wetting agents can provide a growth medium (272) for the cells that will seed luminal surface of the prosthesis. Growth media may include, as an example, a blood centrifugation product such as PPP, which may be derived from the Magellan™ device, as described above. A preparation media may also be provided to the luminal surface after wetting, but prior to addition of the blood centrifugation product, as will be described below. Cells in suspension can be introduced into the prosthesis lumen (274). Any technique can be used to introduce the cells, but an exemplary technique calls for dispensing the cells in suspension with a sterile syringe and needle through the septa of the centrifuge tube. The cells may be added in suspension carefully from one end of the centrifuge tube. To reduce the risk of creating air pockets, it may be advantageous to begin filling the prosthesis in a vertical position from the bottom up to the top.

The prosthesis, with cells in suspension, is loaded into the centrifuge (276). As described above in connection with FIGS. 16-25, loading may include a series of procedures, such as sealing a tube with a plug or septa, inserting a tube into an adapter, and securing a cap to the tube. Axial centrifugation, which may be substantially vertical or substantially horizontal, is performed (278). Examples of duration and degree of centrifugation are discussed above. It is usually desirable to perform axial centrifugation (278) promptly after cells in suspension are introduced into lumen (274), so that the cell suspension is more uniform during centrifugation. Some centrifuges support a short period of agitation prior to centrifugation. Agitation can help make the cell suspension more uniform.

Following centrifugation, the prosthesis can undergo an optional period of incubation (280). Incubation allows the seeded cells time to develop focal adhesions with the luminal surface, which will reduce the risk of later cell dislodgment. Incubation periods may vary in duration, for example, from five minutes to two hours. A typical incubation period may be twenty minutes. During incubation (280), it is possible that the prosthesis may be static, i.e., allowed to sit idle in the centrifuge at room temperature without any intervention. It is also possible that the prosthesis may be subjected to additional processing. For example, the prosthesis may be rotated at a much lower angular velocities, for example, applying lower g's. Another example of further processing is subjecting the prosthesis to pulsatile fluid flow that mimics the flow of fluid in the patient's body, which may enhance the acclimatization of the cells.

Following centrifugation and any incubation period, the prosthesis is unloaded from the centrifuge (282). The prosthesis can be removed from the centrifuge tube 152, 202 and protective sleeve 126, 206 (284) and delivered for implantation in the patient (286). In some circumstances, removal of sleeve (284) need not precede implantation (286). It may be possible to maintain the prosthesis inside protective sleeve 126 during implantation. Near the conclusion of implantation, e.g., just prior to or just after cross-clamp release, the sleeve can be removed.

By keeping the protective sleeve in place during implantation, the risk of seeded cell loss or de-wetting due to forces applied to the prosthesis during implantation can be reduced. Further, the risk of the prosthesis becoming wetted out with blood from surrounding tissues during implantation, which may lead to seroma formation, may also be reduced. In some embodiments, the sleeve may be attachable to a tunneler for ready creation of a tunnel through patient tissue, and placement of the sleeve and prosthesis that "follow" the tunneler within the tunnel. The sleeve may be removed after such placement. The Atrium Slider™ GDS system, sold by Atrium Medical Corp., is an example of a system in which a sleeve is connected to a tunneler for implantation of the sleeve and a prosthesis.

One or more of introduction of a wetting agent, growth medium such as a blood centrifugation product, and cells as described above may, but need not, occur with the prosthesis located in a centrifuge tube, such as tube 202. Such materials may be introduced into the lumen of the prosthesis while the prosthesis is in the tube via a delivery port 214 and septum 210 using a syringe 216 and needle 218, as described above with reference to FIG. 22. Such materials may, but need not, be removed from the tube prior to introduction of another of the materials. Removal of materials from the prosthesis lumen within the tube may also be via a delivery port and septum, using a syringe and needle, as described above.

Preparation and seeding of the prosthesis can be performed in a matter of minutes, and can be performed in the operating room. Operating room personnel can, for example, introduce cells in suspension into the lumen of the prosthesis (274), load the prosthesis into the centrifuge (168), operate the centrifuge to apply axial centrifugation (278), remove the prosthesis from the centrifuge (282) and the protective sleeve (284), and the deliver prosthesis for implantation in the patient (286). It may also be possible to place the prosthesis in a protective sleeve (268) in the operating room, wet the luminal surface (270), and apply a growth medium (272). It may further be possible to perform additional functions in the operating room that are not shown in FIG. 26, such as harvesting endothelial cells or cutting a prosthesis to a customized length for a patient.

The invention facilitates a "one-stage procedure," in which a vascular prosthesis is prepared for implantation and is implanted during a single surgical operation. This "one-stage procedure" provides significant advantages over a conventional "two-stage procedure" for preparation of a vascular prosthesis for implantation. The "two-stage procedure" involves two surgical operations, typically separated by a month or more. In the first operation, the surgeon retrieves a source of endothelial cells from the patient. The surgeon does not implant a prosthesis during this first surgical operation. The medical staff harvests the endothelial cells, and cultures the cells (i.e., grows the cells in vitro) to increase their numbers. Culturing typically takes several weeks. Thereafter, the patient undergoes a second surgical operation to implant a seeded prosthesis. The medical staff seeds the prosthesis, and waits for a period after seeding to allow the cells to adhere to the prosthesis. Seeding may also entail employing adhesion-promoting substances, such as fibrin glue, that promote adhesion. After the waiting period, the medical staff supplies the seeded prosthesis to the surgeon for implantation.

The "one-stage procedures" shown in FIGS. 12 and 26 have the patient make a single visit to the operating room. Harvesting, prosthesis preparation and implantation can be accomplished during this single visit. Axial centrifugation can efficiently cause the seeded cells to accumulate evenly on the luminal surface within a matter of minutes. A single surgical procedure significantly benefits the patient in terms of convenience, comfort and cost.

The "one-stage procedure" omits culturing. In general, the purpose of culturing is to grow enough endothelial cells to compensate for cell losses that occur due to in vivo or post-implant washing away, and to form a confluent monolayer in the lumen. In the one-stage procedure, axial centrifugation of a prosthesis formed from ePTFE as described above can result in less risk of cells washing away because the seeded cells are received in the luminal surface of the prosthesis.

The one-stage procedure also omits the waiting period that allows the cells to adhere to the prosthesis after seeding. Because the recesses receive the cells, the cells are protected from washing away and can improve adhesion in vivo. Adhesion-promoting substances may be unnecessary. Administration of anticoagulant drugs can control the thrombotic potential of the prosthesis until the seeded prosthesis can form a confluent endothelial cell lining in the lumen. In addition, the one-stage procedure permits cells to grow under physiological conditions of pressure and shear stress, which promotes the formation of a more dense and orientated endothelial tissue lining.

Besides making a one-stage procedure feasible, the invention may result in one or more other advantages. In the case of a vascular prosthesis, fewer endothelial cells will be washed away from a luminal surface that includes recesses. As a result, the prosthesis maintains a high population of endothelial cells and can grow a confluent layer of cells in a short time. The prosthesis may also support in situ growth. If cell recesses are formed on substantially less than the full luminal surface of the prosthesis and if the seeding procedure deposits seeded cells onto the regions with recesses, fewer harvested cells are needed to seed the prosthesis. The harvested cells can be concentrated into cell-rich regions on the luminal surface supportive of rapid cell growth. The surface regions with cell recesses can be contiguous or interconnected by cell recess-containing paths to support formation of an endothelialized luminal surface. The patient benefits from the presence and health of the endothelial cells.

Figure 27:
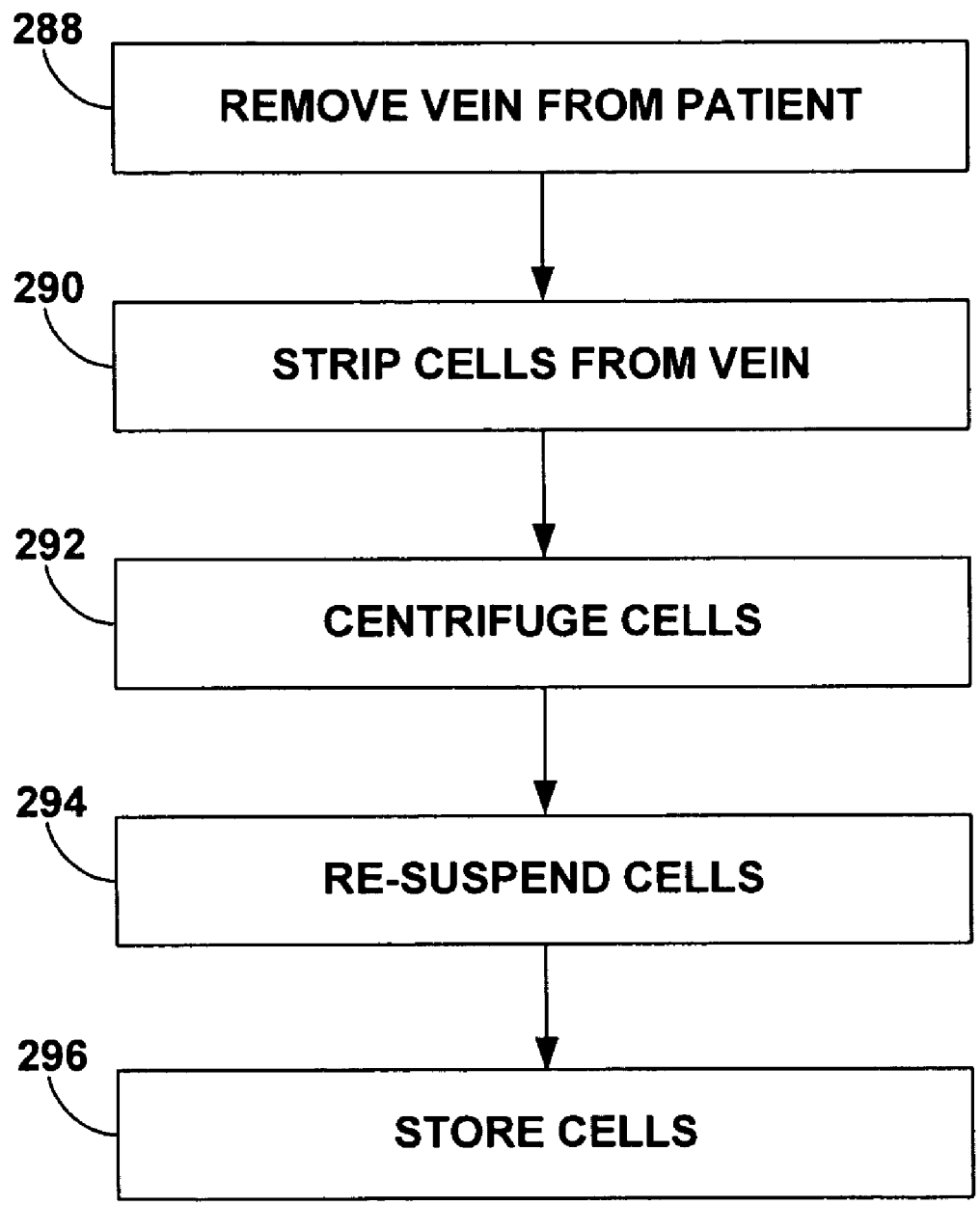
FIG. 27 is a flow diagram illustrating an example cell harvesting technique.

FIGS. 27-30 are flow diagrams depicting other embodiments of and/or further details for the seeding technique described in FIG. 26. For example, FIG. 27 is a flow diagram illustrating an example cell harvesting technique. A clinician begins the process by surgically removing a vein from the patient (288). This vein harvest may be performed immediately prior to the implantation. The vein is typically an expendable vessel not vital to the health of the patient. Once the vein is removed, or excised, the vein is stripped of its endothelial cells (290).

Cell stripping may be done through the use of a collagenase or other enzymatic digestion method. Cell stripping may be done with or without everting the vein. In either case, the vein may be soaked in or otherwise exposed to the enzyme for a period of time adequate to facilitate removal of endothelial cells from the inner lumen of the vein, e.g., approximately 15 minutes.

Further, the invention is not limited to seeding endothelial cells harvested from a vein. For example, the seeded endothelial cells may be harvested from other sources, such as adipose tissue, using any of a variety of known techniques. However, harvesting cells from an everted or cannulated vein via enzymatic digestion is presently the most common technique.

A centrifuge is used to spin the stripped endothelial cells and create a pellet of cells (292). A user then re-suspends the pellet of cells in growth media (294). The cells are then stored until the seeding process (296). In some cases, the suspended cells may immediately be used to seed prosthesis 208. In this manner, the patient may only endure one surgical procedure.

Figure 28:
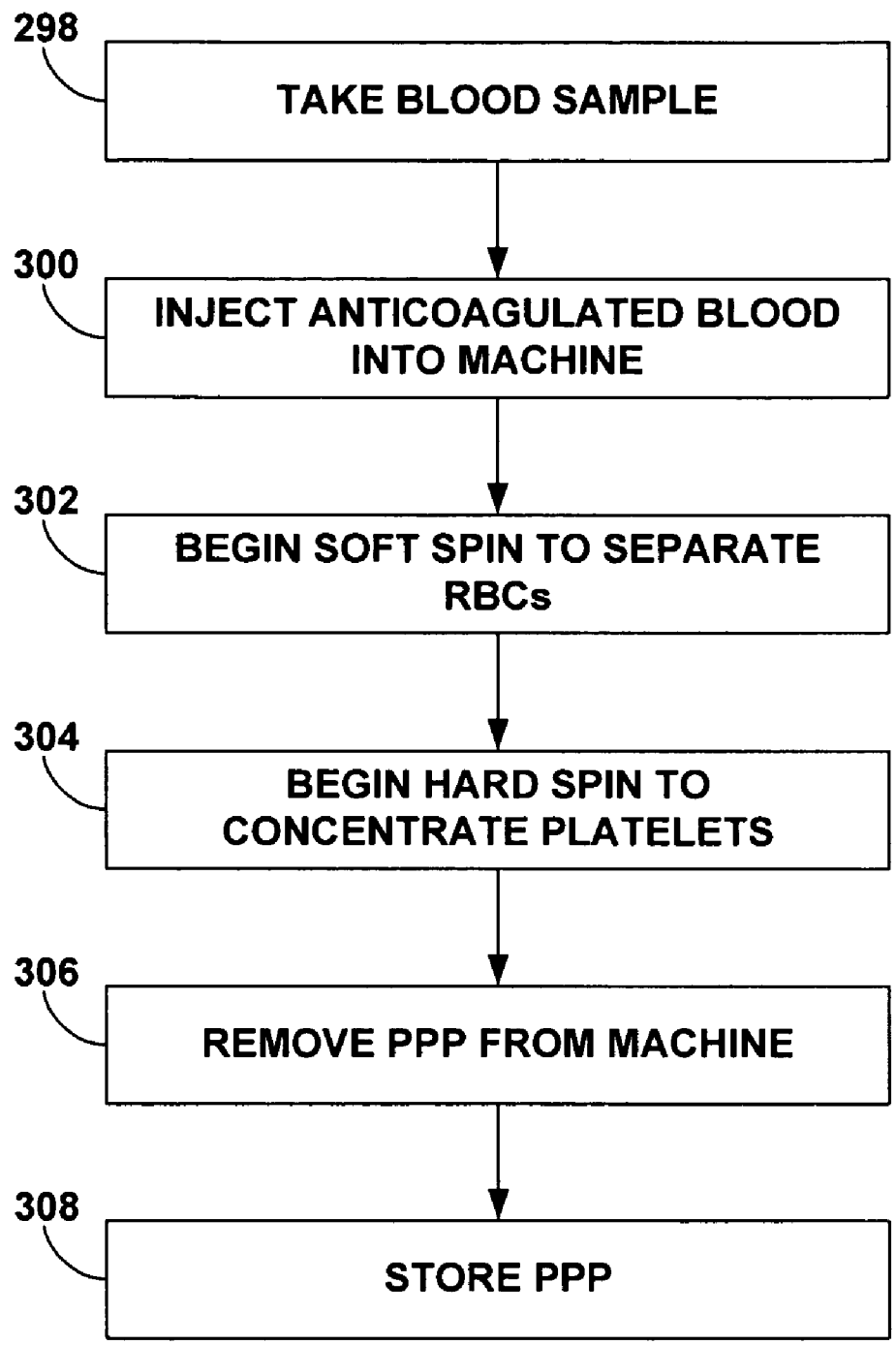
FIG. 28 is a flow diagram illustrating an example technique for producing platelet-poor plasma (PPP).

FIG. 28 is a flow diagram illustrating an example technique for producing platelet-poor plasma (PPP), which is an example of a blood centrifugation product that may be applied to a luminal surface of a prosthesis prior to cell seeding. A clinician first takes a blood sample for the patient (298). The blood sample may only need to be between approximately 30 and approximately 60 milliliters, and may be drawn into a syringe that includes heparin, a sodium citrate solution, or another suitable anti-coagulant. The clinician then injects the anticoagulated blood into a separating device, such as a centrifuge or the Magellan™ separator (300).

The separating device begins a soft spin at approximately 2800 revolutions per minute (RPM) to separate red blood cells (RBC) from the blood (302). Next, the device begins a hard spin at approximately 3800 RPM to concentrate the platelets out of the plasma (304). Once the platelets have been concentrated, a clinician removes the PPP from the machine (306). Finally, the clinician may store the PPP until needed for the cell seeding process (308). The PPP may be, for example, stored in a refrigerator at approximately 4 degrees Celsius. Storing the PPP for a period of time, e.g., a number of hours or overnight, may allow the red blood cells to settle out of the PPP. The PPP may be stored an amount of time adequate to allow 80%, and more preferably 95%, of the RBC to sediment out from the PPP.

In other embodiments, the machine may spin the blood sample at different RPMs. The RPMs listed may be appropriate for the Magellan™ separator, but machines with other radii or components may require different spinning cycles. Exemplary durations of the soft and hard spins are 2 minutes for the soft spin and 3 minutes for the hard spin for a blood sample of 30 mL. Larger blood samples may require longer spin durations.

Other blood centrifugation products that may be additionally or alternatively applied to a luminal surface according to the invention, such as PRP, may be recovered as one of the products other than PPP produced by the same technique described above. For example, PRP may be derived from the concentrated platelets described as being another product produced with PPP by the above process. Alternatively, different RPMs or centrifugation cycles may be used to produce other blood centrifugation products. Further, in some embodiments, the blood centrifugation products may be diluted with Plasma-Lyte®A, EBM-2, anticoagulants, or other fluids prior to application to a prosthesis.

Blood centrifugation products, such as PPP may be produced in a short time using devices such as the Magellan™ separator or a standard clinical centrifuge. Soaking a prosthesis with such blood centrifugation products may provide a more suitable surface for endothelial cell adherence than surfaces not prepared with blood centrifugation products, as supported by experimental data relating to use of PPP which will be discussed below. Blood centrifugation products may provide endogenous adhesion proteins and growth factors, which may initiate healing pathways, and increase the ability for seeded cells to adhere to the luminal surface of prosthesis 208 and multiply.

The Magellan™ separator is an example device for deriving blood centrifugation product from blood, and other devices capable of providing platelet-rich, platelet-poor, or other fractions or products may be used. Nonetheless, based on the experimental data discussed below, it is believed that the Magellan™ separator may provide blood centrifugation products, and particularly PPP that, when a prosthesis is soaked therein, provides a particularly suitable surface for endothelial cell adherence.

Figure 29:
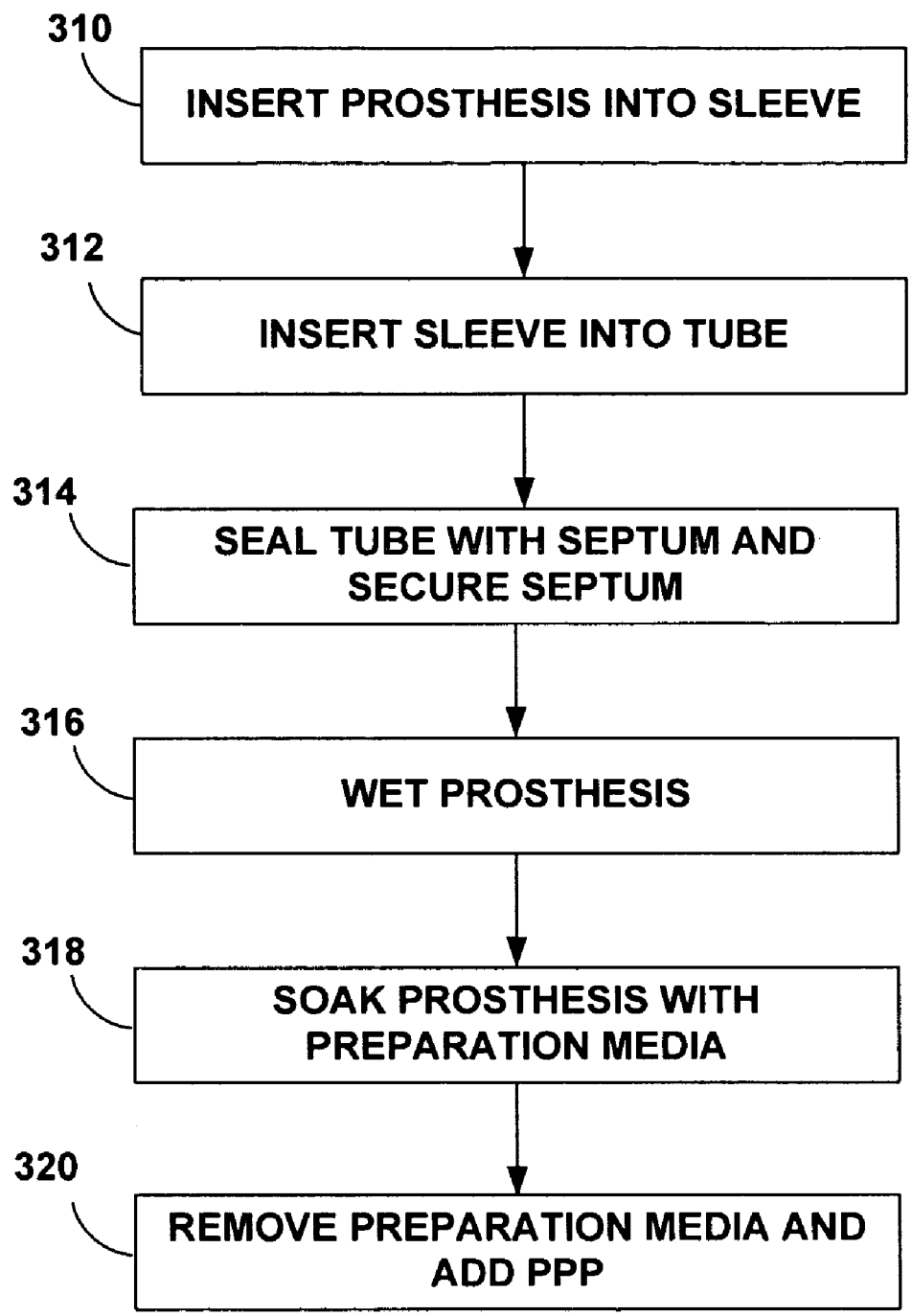
FIG. 29 is a flow diagram illustrating an example technique for preparing a vascular prosthesis to accept cells.

FIG. 29 is a flow diagram illustrating an example technique for preparing a vascular prosthesis to accept cells. The following example technique is discussed with reference to prosthesis handling system 200 of FIGS. 20-25. However, the technique may be used with other prostheses and systems, such as those described with reference to FIGS. 1-19.

According to the example technique, vascular prosthesis 208 is inserted into sleeve 206 (310). The sleeve and prosthesis may then be inserted into centrifuge tube 202 (312). The ends of tube 202 may be sealed with septa 210, which may be secured with tube caps 212 (314). As discussed above, the assembled centrifuge tube, i.e., prosthesis protection system 200, may be provided to an operating room as a sterile package.

Vascular prosthesis 208 may then be fully wetted with a wetting agent to displace any air (316). The wetting agent may be delivered through the septa using a syringe and needle. An appropriate wetting agent may be ethanol or another organic liquid. Other treatments that may make ePTFE more wettable include ionized gas plasma or sodium napthalate; however, some such treatments may degrade a polycarbonate centrifuge tube 202, and would need to be applied to the prosthesis prior to insertion therein.

However, the invention is not limited to embodiments in which wetting occurs as described above. For example, in some embodiments, wetting may occur entirely prior to the prosthesis being inserted into the sleeve, and the insertion of both into the tube. Further, in some embodiments, wetting may occur both prior to and during insertion of the prosthesis into the sleeve. Wetting prior to insertion of the prosthesis into the sleeve may allow a clinician to visually determine whether the prosthesis is completely wetted, while inserting the prosthesis into the sleeve while both are submerged in the wetting agent may reduce the likelihood of de-wetting during the insertion.

After wetting, the clinician soaks prosthesis 208 with a preparation media (318). The preparation media may also be delivered through one of the septa using a syringe and needle. The preparation media may include growth factors, calcium, and other elements necessary to prepare prosthesis 208 for cell adhesion. Calcium may help to promote formation a thin clot layer or fibrin mesh on the luminal surface of prosthesis 208 when exposed to PPP or other blood centrifugation products, as will be described below. Further, as discussed above, the PPP or other blood centrifugation product may be derived from blood that was prevented from clotting by addition of a non-calcium chelating anticoagulant, such as a sodium citrate solution. Use of blood centrifugation products derived from such blood may facilitate development of a thinner fibrin layer on the graft surface than blood centrifugation products derived from blood that was not mixed with such an anticoagulant.

The clinician next removes the preparation media and fills tube 202 with the blood centrifugation product, e.g., through one of the septa using respective syringes and needles (320). The blood centrifugation product may need to remain within tube 202 for a certain amount of time such that prosthesis is adequately prepared to accept cells. In some embodiments, tube 202 need not be sealed prior to introduction of one or both of the protective media and the blood centrifugation product. In such embodiments, these materials need not be injected into and removed from the prosthesis lumen via a delivery port 214 in the cap and the septum.

Figure 30:
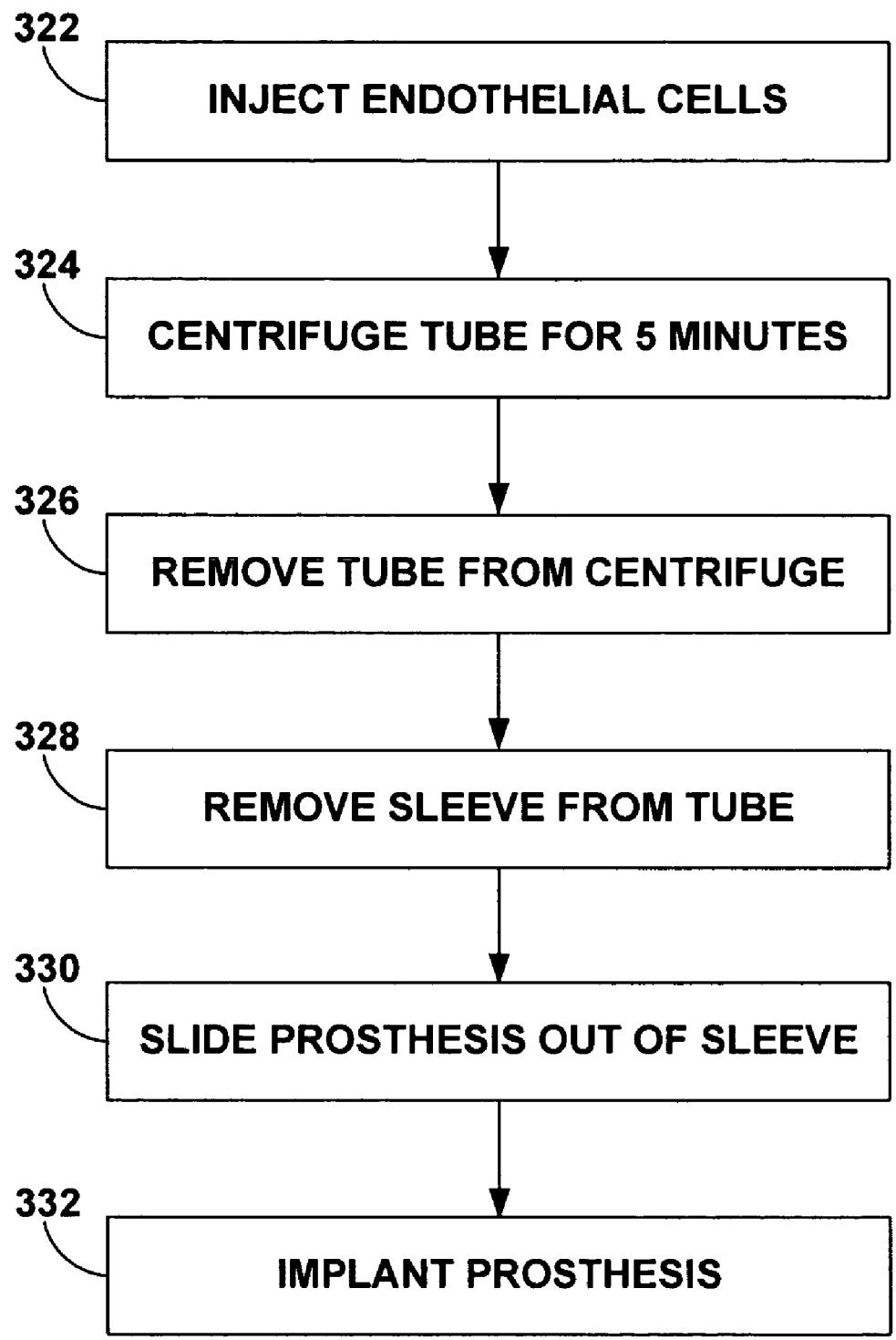
FIG. 30 is a flow diagram illustrating an example cell seeding and vascular prosthesis implantation technique.

FIG. 30 is a flow diagram illustrating example cell seeding and vascular prosthesis implantation techniques. Beginning with the blood centrifugation product filled prosthesis of FIG. 29, the clinician removes the blood centrifugation product, e.g., PPP, and injects the endothelial cells for seeding (322). While the blood centrifugation product may be removed and the cells may be injected though a needle piercing septum 210, some embodiments of seeding device 200 may require the clinician to remove tube cap 212 to remove the blood centrifugation product and inject the cells.

Once injected, seeding device 200 is placed within centrifuge 220 and spun, for example at 250 g for 5 minutes, to seed the cells within the lumen of prosthesis 208 (324). Next, the clinician removes seeding device 200 from centrifuge 220 (326) and removes prosthesis 208 while in protective sleeve 206 from centrifuge tube 202 (328). Before implantation, the clinician slides vascular prosthesis 208 out from protective sleeve 206 (330). The clinician then implants prosthesis 208 into the patient by advancing the prosthesis through a tunnel and suturing the ends of the prosthesis to adjoining vessel edges (332).

In other embodiments, as discussed above with reference to FIG. 20, the clinician may implant vascular prosthesis 208 before removing protective sleeve 206. Protective sleeve 206 prevents prosthesis 208 from incurring unwanted bends, kinks, lumen collapse, or other events detrimental to the newly seeded endothelial cells in the prosthesis. Once prosthesis 208 is implanted, the clinician may carefully remove the protective sleeve from the prosthesis before the surgical procedure is complete. Alternatively, protective sleeve 206 may be biodegradable, such that protective sleeve is broken down and absorbed by the patient over a certain period of time.

The techniques of FIGS. 27-30 may be incorporated into a "one-step" procedure, i.e., involving single surgical hospital visit, as discussed above with reference to FIG. 26. A one surgical visit procedure may reduce risk factors associated with surgery relative to other vascular prosthesis implantation techniques. In some embodiments, the techniques of FIGS. 27-30 may be applied to other implantable medical devices other than vascular prostheses.

Moreover, various embodiments of the invention take advantage of physical properties of ePTFE, a material that has a proven track record in implantable medical devices. This material is biocompatible, and handles and sutures well. The techniques described herein for forming recesses and seeding do not adversely affect the favorable features of ePTFE. At the same time, the techniques described herein for forming recesses and seeding offer protection for endothelial cells as well as surface area for endothelial cell outgrowth.

EXAMPLE 1

Figure 31:
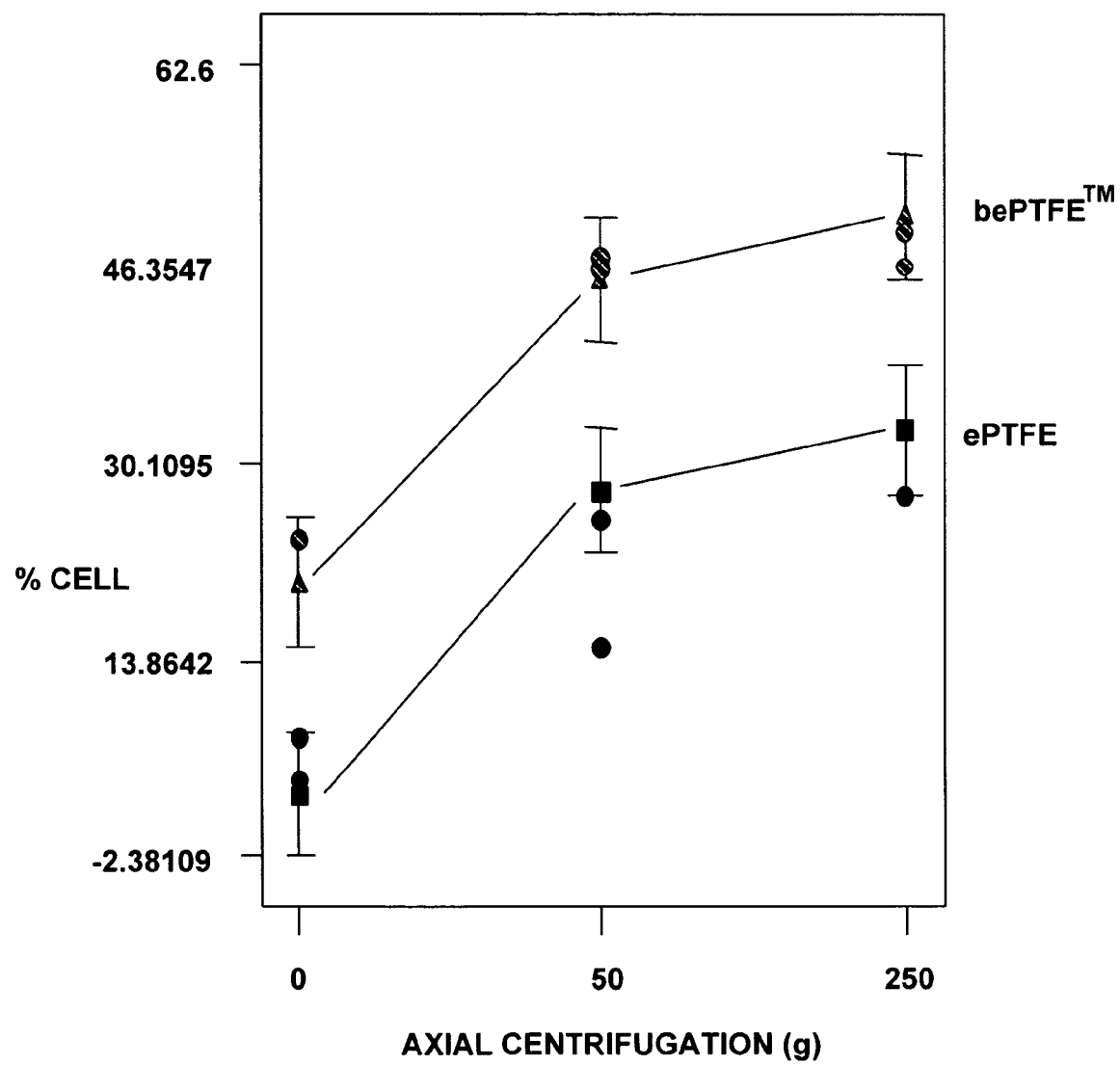
FIG. 31 is a graph of experimental data illustrating relationships among centrifugation, cell retention and device material.

Example 1 is discussed with reference FIGS. 31-37, and relates data from experiments generally performed according to the techniques discussed with reference to FIG. 26. FIG. 31 is a graph of experimental data, with error bars, illustrating cell retention (identified with "% cell," meaning specifically the percentage of cells attached to the graft based upon the number of cells applied in suspension to the graft at centrifugation) as a function of axial centrifugation upon test devices. The designation "ePTFE" refers to one or more test devices constructed from material that has not been processed by rubbing, as described above. The designation "bePTFE," which is a trademark of Medtronic, Inc., refers to one or more test devices constructed from material that has been processed as described above. In particular, bePTFE™ has been rubbed with a brush, and the acronym stands for "brushed ePTFE." Each test device was about four cm long and about four mm in diameter. Axial centrifugation, where applied, was applied for five minutes using an apparatus similar to that shown in FIGS. 16-19. Other data sets under different conditions have resulted in differing percentages of cell retention. Differences in conditions can include, for example, employment of wetting agents and growth medium. The data depicted in FIG. 31 are representative, however, of experimental results generally.

The left side data points of FIG. 31 represent cell retention without axial centrifugation, the center data points represent cell retention with axial centrifugation at 50 g, and the right data points represent cell retention with axial centrifugation at 250 g. As the data in FIG. 31 show, the bePTFE™ device demonstrated greater cell retention than the ePTFE device at all levels of centrifugation. The data in FIG. 31 also show, however, that axial centrifugation improves the cell retention on both the bePTFE device and the ePTFE device, and that higher g's results in higher cell retention.

The data in FIG. 31 further illustrate that, even though higher g's results in higher cell retention, there is a "leveling off," and that, above a level of g's, less marginal benefit is obtained by using higher g's. Further data, not shown in FIG. 31, confirm the leveling off. In other words, although axial centrifugation improves cell retention for both the bePTFE device and the ePTFE device, the benefit achieved by higher g's diminishes.

Figure 32:
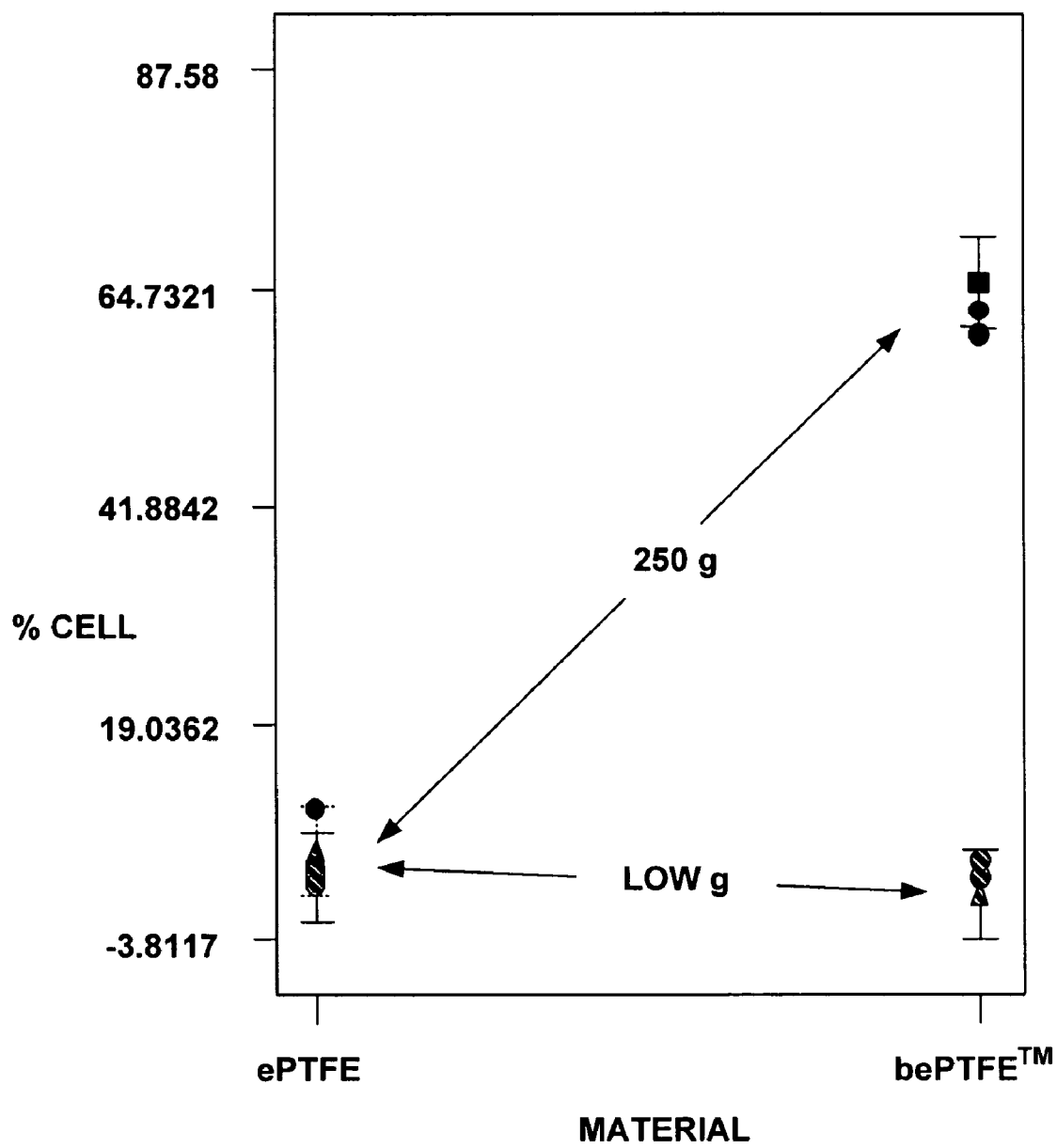
FIG. 32 is a graph of experimental data illustrating cell retention for device materials following lower g and higher g axial centrifugation.

FIG. 32 is a graph of experimental data further illustrating cell retention following lower g and higher g axial centrifugation. Data pertaining to the ePTFE device are on the left and data pertaining to the bePTFE™ device are on the right. Once again, other data sets under different conditions resulted in differing percentages of cell retention, but the data depicted in FIG. 32 are representative of experimental results generally.

The "low g" data points represent data collected as the test devices were rotated at one rpm, thereby imparting very little axial centrifugation effect. For both the bePTFE™ device and the ePTFE device, cell retention was modest to poor at low g. When 250 g were applied, however, both devices demonstrated improved cell retention. The improvement of cell retention in the bePTFE™ device was markedly superior to the improvement demonstrated by the ePTFE device.

Experiments with test devices that include patterns of recesses also support the data presented in FIG. 32. Cells may adhere to both ePTFE sites and bePTFE™ sites, but generally prefer the bePTFE™ sites. Also, brushing may produce lines or grooves of raised nodes. Following seeding with axial centrifugation, cells generally prefer to populate proximate to the grooves. Consequently, axial centrifugation can be used to support seeding of endothelial cells at specified sites on a device.

Figure 33:
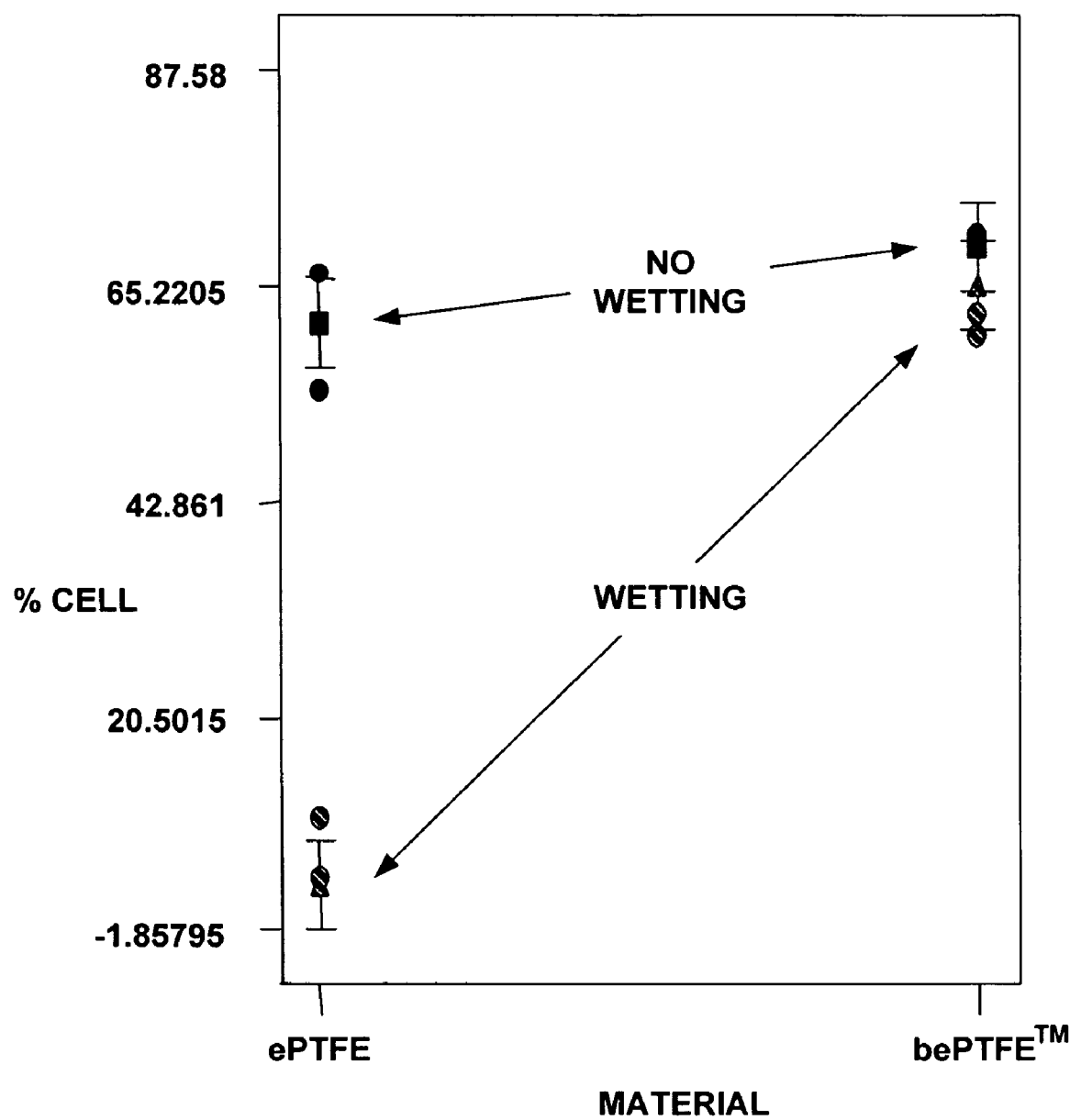
FIG. 33 is a graph of exemplary data illustrating cell retention for device materials as a function of wetting prior to axial centrifugation.

FIG. 33 is a graph of experimental data illustrating cell retention with and without wetting, followed by axial centrifugation at 250 g for five minutes. Once again, other data sets under different conditions resulted in differing percentages of cell retention, but the data depicted in FIG. 33 are representative of experimental results generally. In particular, similar results appear when different levels of axial centrifugation are applied, and when no axial centrifugation is applied.

The test devices were wetted as described above with a basal growth medium commercially available from Cambrex as product CC-3156, with SingleQuot® Supplements and Growth Factor, product CC-4143. Measurements of cell retention were taken promptly after centrifugation.

The data in FIG. 33 show that wetting depresses cell retention, but that the depression is significantly less with a bePTFE™ device than with an ePTFE device. It is believed that wetting can, in the short term, impair the ability of the cells to form focal adhesions to the device material.

The data in FIG. 33 do not compel the conclusion that wetting is undesirable, however. In spite of the depression of cell retention, wetting usually brings about many benefits, as described above, that outweigh the depression of cell retention. Generally speaking, wetting results in faster development of endothelial cells in the patient, and faster healing. In addition, activities following centrifugation, such as allowing incubation, can improve the ability of the cells to form focal adhesions to the device material when the device has been pre-wetted.

FIGS. 34 and 35 are tables showing data collected pertaining to devices seeded with axial centrifugation. The data were obtained by experimentation upon test devices that included ePTFE and bePTFE™. The reported percentages represent averages for two test devices for each material.

In FIG. 34, the test devices were about four cm long and about four mm in internal diameter. None of the test devices received a growth medium. Following introduction of cells into the respective lumens, all test devices were subjected to 250 g axial centrifugation for five minutes, using an apparatus similar to that shown in FIGS. 16-19.

The row denoted "A" in FIG. 34 shows the percentage of cells retained on the respective materials promptly after centrifugation. Rows "B" and "C" show the percentage of cells retained on the respective materials following one hour of incubation, in which the seeded device remained untouched in the centrifuge. Row "B" relates to incubation with no additional processing, and row "C" relates to incubation with axial centrifugation at a reduced rate, one g. Row "D" shows the percentage of cells retained on the respective materials following five hours of incubation, in which the seeded device remained untouched in the centrifuge.

As FIG. 34 shows, a bePTFE™ device had a higher percentage of cell retention than an unprocessed ePTFE device, for each of the post-centrifugation activities. An hour of incubation, with and without low-g centrifugation, substantially increased percentage of cell retention for the ePTFE device, but not for the bePTFE™ device. It is believed that incubation enables cells to form focal adhesions to the ePTFE device, resulting in fewer cell dislodgements during handling. A five-hour incubation period, however, results in a drop in cell retention for devices made of both materials. Perhaps due to the absence of platelet-poor plasma in the experiment, the cells expired in a matter of hours.

In FIG. 35, the test devices were about four cm long and about four mm in internal diameter. All test devices were subjected to 250 g axial centrifugation for five minutes, using an apparatus similar to that shown in FIGS. 16-19.

Once again, a bePTFE™ device had a higher percentage of cell retention than an unprocessed ePTFE device, for each of the post-centrifugation activities. Row "A" of FIG. 35 shows the percentage of cells retained on the respective materials promptly after centrifugation, and the results are comparable to those in row "A" of FIG. 34. Row "B" of FIG. 35 shows the percentage of cells retained on the respective materials after an hour of static incubation, and these results are comparable to those in row "B" of FIG. 24. The differences between the percentages in FIGS. 34 and 35 are within the range of error.

Row "C" shows the percentage of cells retained on the respective materials when the test devices were not allowed to stay in the centrifuge for an incubation period, but instead were subjected to a pulsatile fluid flow for one hour. Pulsatile flow mimics the flow of fluid in the patient's body through the pumping of a fluid such as Plasma-Lyte® or EBM-2™ with platelet-poor plasma intermittently through the device. Pulsatile flow was hypothesized to enhance the acclimatization of the cells to the device. The percentage of retained cells declined markedly, however, perhaps because the cells had not had time to form focal adhesions, and were dislodged by the fluid flow.

Row "D" shows the percentage of cells retained on the respective materials when the test devices were allowed to stay in the centrifuge for a one-hour incubation period, then were subjected to one hour of pulsatile fluid flow. This processing did not result in improvement for the ePTFE device, but resulted in marked improvement for the bePTFE™ device. These data suggest that, in some cases, it may be advantageous to let the cells incubate and acclimatize prior to implantation.

Figure 36:
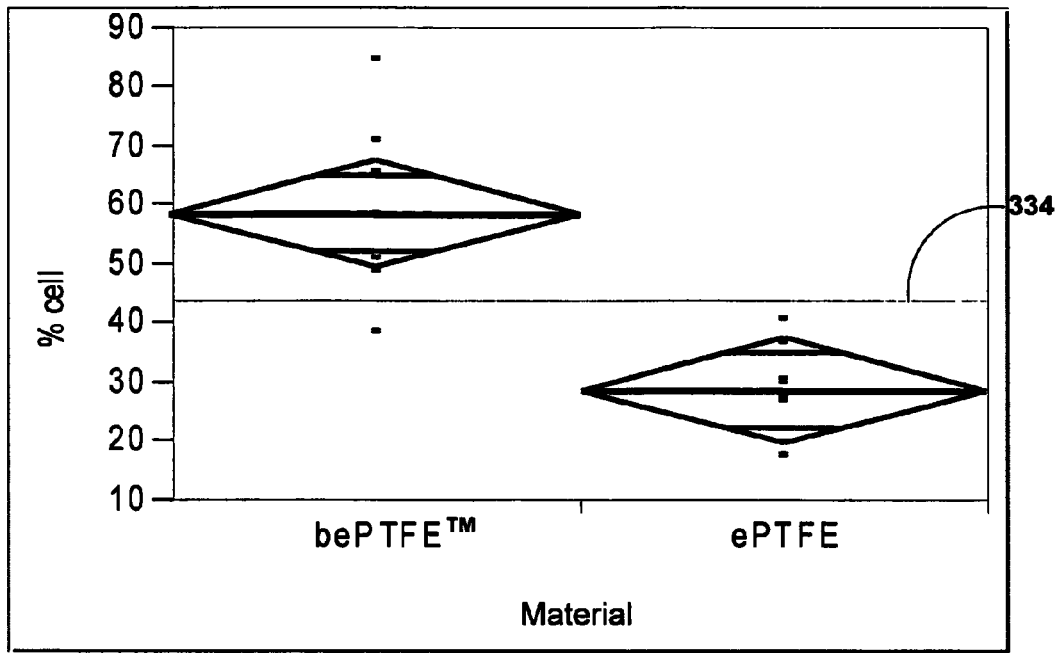
FIG. 36 is a graph illustrating experimental cell retention data, the data divided into two groups based on device material.
Figure 37:
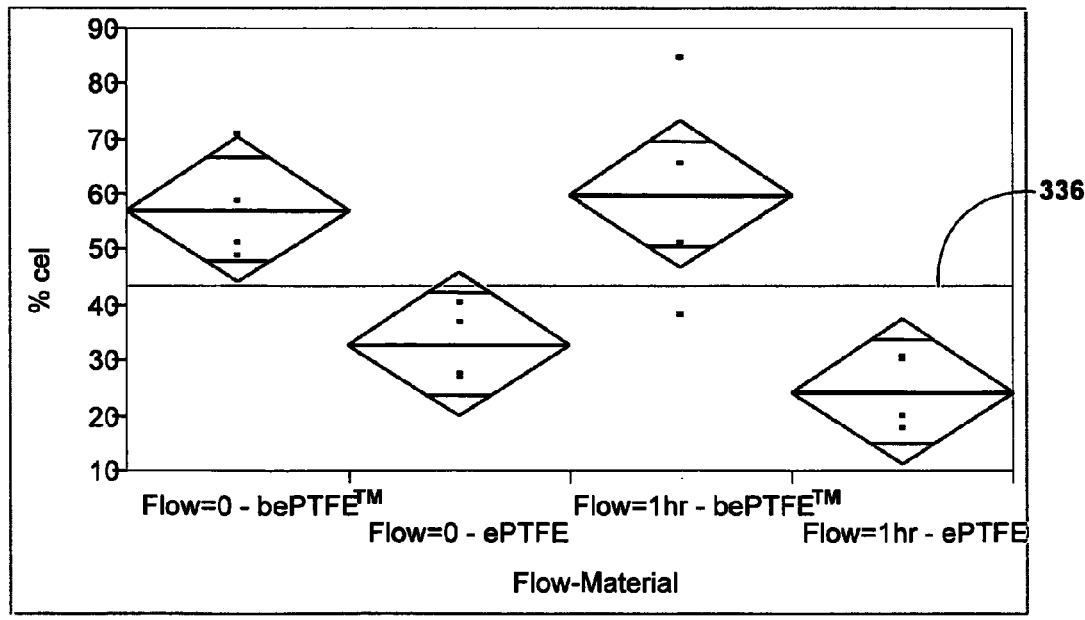
FIG. 37 is a graph illustrating experimental cell retention data, the data divided into four groups based on device material and the presence or absence of flow acclimatization.

FIGS. 36 and 37 are graphs illustrating the experimental cell retention data discussed above with reference to FIGS. 34 and 35. As discussed above with reference to FIGS. 34 and 35, the data were obtained by in vitro experimentation upon sixteen test devices that included ePTFE and bePTFE™. Some devices of each material were subjected to one hour of pulsatile fluid flow, while others of each material were not.

In FIG. 36, the data is divided into two groups based on device material, while in FIG. 37 the data is divided four groups based on device material and the presence or absence of flow acclimatization. FIGS. 36 and 37 illustrate the average cell retention across all devices at lines 334 and 336, respectively. Further, FIGS. 36 and 37 illustrate the statistical distribution for each group by way of the respective diamond-shaped representations, referred to as means diamonds, for each group.

In means diamonds, the horizontal line in the middle of the diamond is the mean of the group, and its width is proportional to the sample number. The top and bottom points of a mean diamond show the upper and lower 95% confident points for the group. The horizontal lines above and below each mean line are called "overlap marks" (OM). These drawn at (SQRT(2))/2* CI, where CI is the confidence interval. For groups of equal size, overlapping OMs mean that the groups are not significantly different at the 95% confidence interval. Thus, in general, if the points of the means diamonds do not overlap, the groups are significantly different (but the reverse is not necessarily true).

As illustrated in FIGS. 36 and 37, the bePTFE™ materials retained a significantly higher percentage of cells than the ePTFE materials. A General Factorial ANOVA statistical analysis showed this difference to be statistically significant ($P<0.05$). Further, as illustrated in FIG. 37, the difference in cell retention percentage between bePTFE™ and ePTFE devices was greater for those devices subjected to one hour of pulsatile fluid flow, primarily due to reduced cell retention for ePTFE devices exposed to fluid flow relative to those not exposed to fluid flow. This difference may be due cells "washing away" from ePTFE surfaces, which lack the recesses provided by bePTFE™ surfaces, when those surfaces are exposed to pulsitile fluid flow that mimics blood flow through an implanted vascular graft.

EXAMPLE 2

Figure 38:
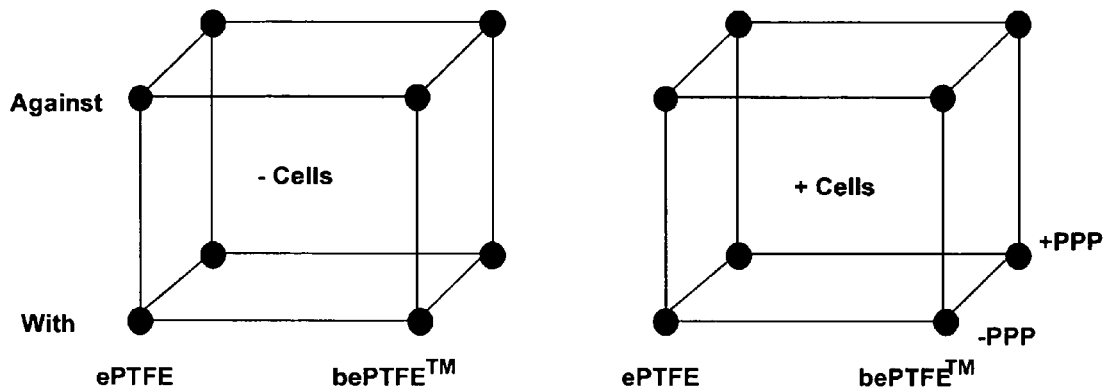
FIG. 38 is a diagram illustrating a cube-plot representation of a $2^4$ full factorial animal study involving implantation of vascular grafts within canine animals.

Example 2 includes test samples from an in vivo study utilizing ePTFE and bePTFE™ vascular prostheses, i.e., vascular grafts, implanted in canine animals. Vascular grafts of each material were prepared and implanted in different ways to test a variety of potentially influential variables. This study utilized a full $2^4$ factorial design on the following four variables: material (ePTFE vs. bePTFE™), alignment of the graft (with blood flow with vs. against the raised nodes, which was believed to be only relevant in bePTFE™ samples where the formed recesses are directional), PPP (none vs. with PPP), and endothelial cell seeding (no vs. yes). A cube plot representation of the $2^4$ full factorial study design is shown in FIG. 38. In this representation every condition tested is shown as a corner of each cube, with the cell seeding condition represented by the two different cubes. Each condition was tested in duplicate, for a total of thirty-two vascular graft implants.

In the study, sixteen canines were used. Each animal weighed between 25 and 30 kilograms, and all were adult females. Impra™ ePTFE Vascular Grafts (available from C. R. Bard, Inc., Murray Hill, N.J.), each with an inner diameter of 4 mm, were modified to yield the test grafts according to the variables of the study. The test grafts were surgically implanted into the left and right femoral arteries of each of the sixteen canines studied.

All conditions were done in duplicate, with restricted randomization such that only female canines were used (for surgical purposes), each animal received an ePTFE and a bePTFE™ graft with type of material alternating between right and left implant positions in replicate animals, and the first eight implant animals received grafts without cell seeding (the second eight animals received the cell seeded grafts).

In addition, control animals did not receive endothelial cell seeded grafts, but received the same surgery necessary to retrieve autologous endothelial cells (bilateral external saphenous vein harvesting). After six weeks, the grafts implanted in each animal were removed to examine the success of the graft.

For completeness and for establishing baseline data, the sham-harvested vessels, i.e., from the eight implant animals that did not receive cell-seeded grafts, were processed the same as those from the eight animals that did receive grafts seeded with their harvested cells. This processing included harvesting endothelial cells and counting the number of cells harvested using a hemacytometer. The harvested cells were seeded onto thirty-two grafts, sixteen of which were implanted into the eight animals designated to receive cell-seeded grafts, and the other sixteen of which were used for bench top analysis. 16 additional, non cell-seeded grafts were implanted into the eight animals designated to receive grafts that had not been seeded with cells.

Cell TiterGlo (CTG) assays were performed on each of the sixteen grafts used for bench top analysis. The CTG assay is a method of determining the number of cells for a given area, and extrapolating that result for the entire vessel. The CTG assay data, in combination with the hemacytometer data, was used to determine the percentage of cells remaining on the graft surface relative to the initial number of cells exposed to the surface during the axial centrifugation cell seeding. As the actual implant procedure done in the second eight animals did not offer any excess (not to be implanted) graft material for bench top analyses, such as CellTiter-Glo assays, data from the sham grafts seeded with the cells from the animals who received non-seeded grafts offers an estimation of the cell-seeded grafts that were actually implanted in study animals.

Figure 39:
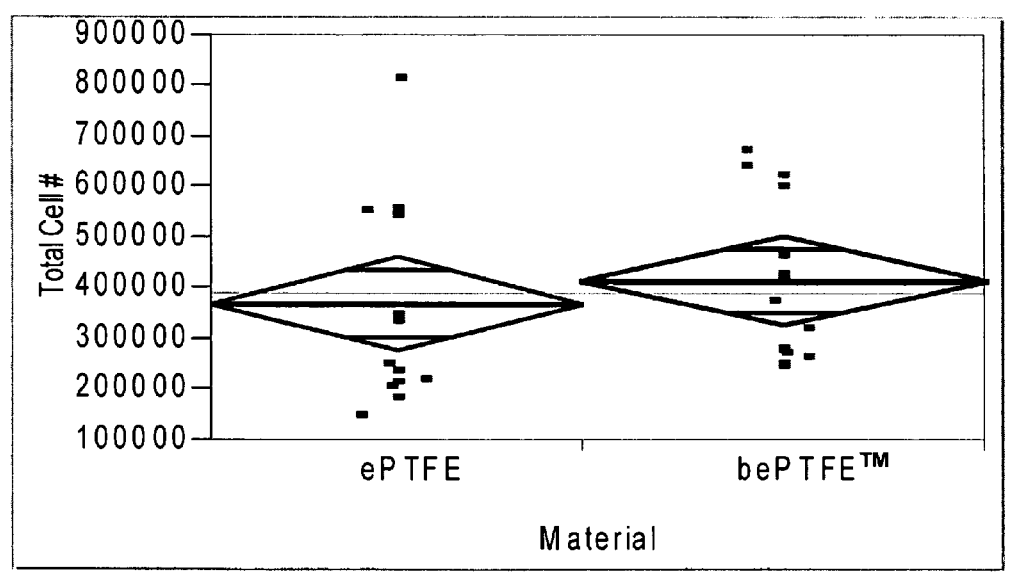
FIG. 39 is a graph illustrating level of cell exposure data for the grafts, the data divided into two groups based on graft material.

FIG. 39 is a graph illustrating cell exposure (hemacytometer) data for the non-implanted, sham grafts, with the data divided into two groups based on graft material. This data provides an estimation of the cell exposure of the grafts actually implanted. FIG. 39 illustrates that the bePTFE™ grafts were on average exposed to higher number of endothelial cells relative to the ePTFE grafts. However, due to the substantial overlap of the statistical distribution of the data for the two materials as shown by the respective diamond-shaped representations, FIG. 39 illustrates that this difference is not statistically significant. In other words, there was not a statistically significant difference is the overall cell exposure between the two groups. FIG. 39 suggests that, although the grafts in this experiment were exposed to a variable number of cells, this variation was distributed across the experimental variables such that its effect on any one of the variables was not statistically significant.

As discussed above, cell uptake (CTG assay) data was also collected for the for non-implanted, sham vascular grafts to provide an estimate of the cell uptake of the grafts acutally implanted. The "% CTG" in the following figures and discussion represents the percentage of endothelial cells measured on the graft surface following axial centrifugation, as measured by CTG assay, relative to the starting number of venous endothelial cells applied to the graft, as measured by the hemacytometer. % CTG is essentially the same as the % cell and cell retention data discussed above with reference to Example 1, in the sense that both data represent the percentage of cells retained after cell-seeding and axial centrifugation.

Figure 40:
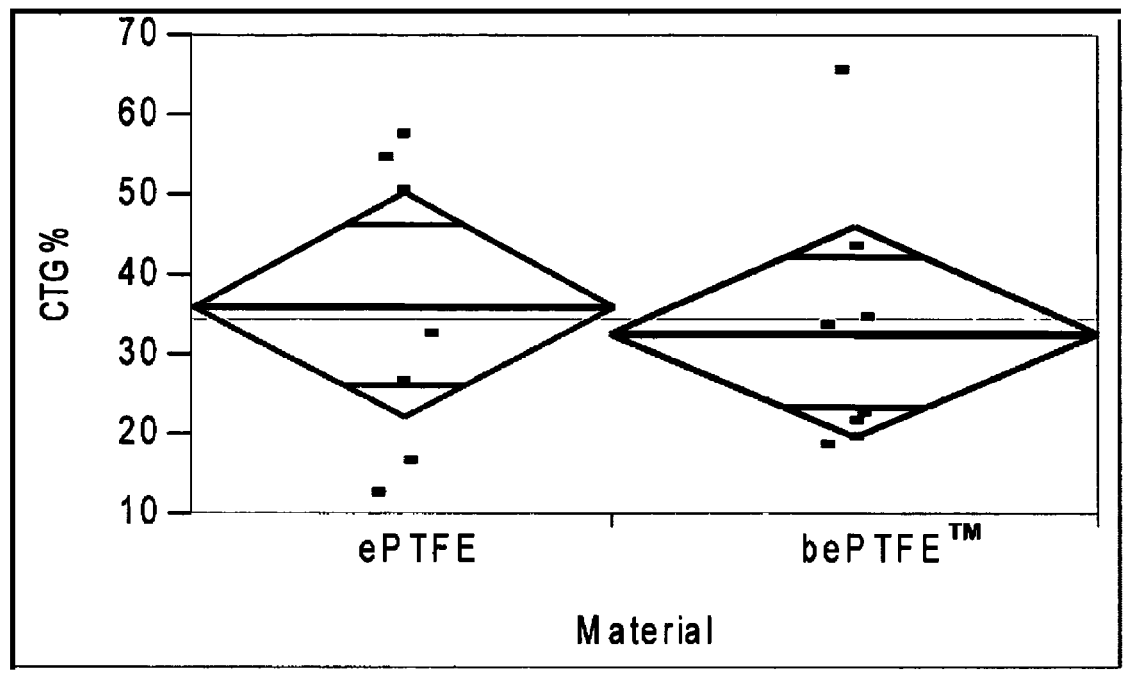
FIG. 40 is a graph illustrating the cell uptake data for the non-implanted, control vascular vascular grafts divided into two groups based on graft material.

FIG. 40 is a graph illustrating the cell uptake data for the non-implanted, control vascular vascular prostheses divided into two groups based on prosthesis material. As shown in FIG. 40, in this experiment, the ePTFE grafts on average retained a slightly higher percentage of cells after centrifugation than the bePTFE™ grafts. However, as also illustrated in FIG. 40, this difference is not statistically significant, as shown by the substantial overlap of the means diamonds. The difference between the % CTG data by material from this experiment illustrated in FIG. 40, and the % cell data for another experiment illustrated in FIG. 36, is due to the following: the data in FIG. 40 represents single samples exposed to unique cell populations and variable cell concentrations, whereas the data in FIG. 36 represents samples exposed to a single source and uniform concentration of endothelial cells.

Figure 41:
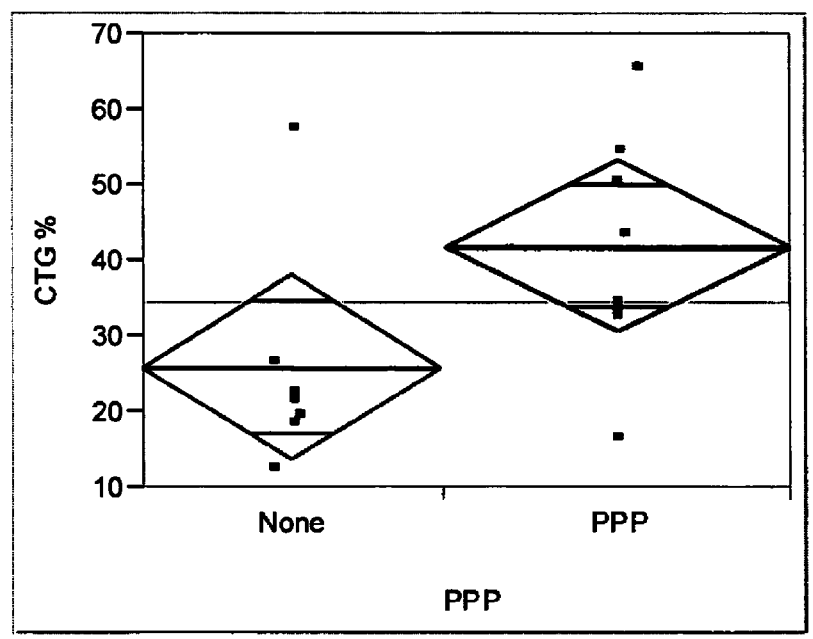
FIG. 41 is a graph illustrating the cell uptake data for the non-implanted, sham grafts divided into two groups based on whether or not the grafts were treated with platelet-poor plasma.

FIG. 41 is a graph illustrating the cell uptake data for the non-implanted, control vascular vascular prostheses divided into two groups based on whether or not the prostheses were treated with PPP. As shown in FIG. 41, PPP-treated grafts tend to show a higher % CTG, i.e., better retain endothelial cells. A General Factorial ANOVA statistical analysis showed this trend to have slight statistical significance (P<0.07). This trend became statistically significant if the highest % CTG for each material was omitted from the analysis.

After a six week implant duration, the thirty-two test grafts were explanted and analyzed. Gross photographs were taken of all explants, and the images were used to assess the apparent graft patency (occluded vs. non occluded grafts) and extent of luminal thrombus. Patency indicates how open, or not occluded, the graft is. Patency was visually and subjectively determined, and a score of 0 was given for a graft that was completely occluded, while a score of 1 was given for a graft that was not completely occluded.

Degree of thrombosis was subjectively identified based upon visual inspection of gross explant images by three scientists in a blind fashion. Scores of 0-4 were given to each graft using the following scale: 0=occluded, 1=>75% covered in pink/red thrombus, 2=up to 50% covered in pink/red thrombus, 3=up to 25% covered in pink/red thrombus, 4=white with no apparent thrombus.

Figure 42:
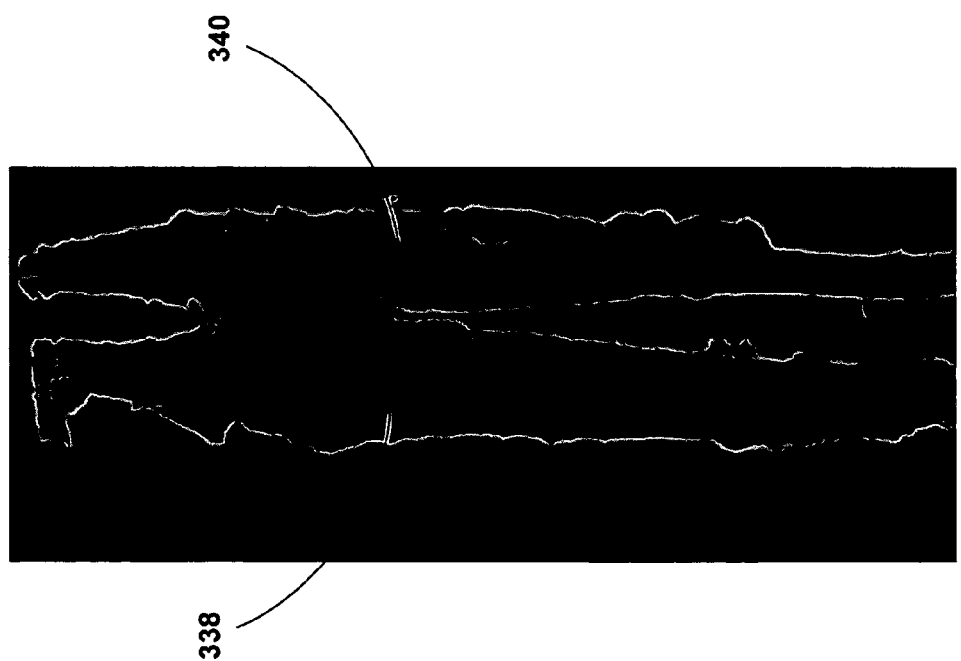
FIG. 42 illustrates explanted ePTFE vascular grafts which were not seeded with cells or treated with platelet-poor plasma prior to implantation.

FIG. 42 illustrates a gross photograph of explanted ePTFE vascular grafts which were not seeded with cells or treated with platelet-poor plasma prior to implantation. As illustrated by the shaded areas 338 and 340 on the lumens of the grafts of FIG. 42, explanted ePTFE grafts that were not treated with PPP or seeded with cells had significant and easily identifiable thrombosis formation.

Figure 43:
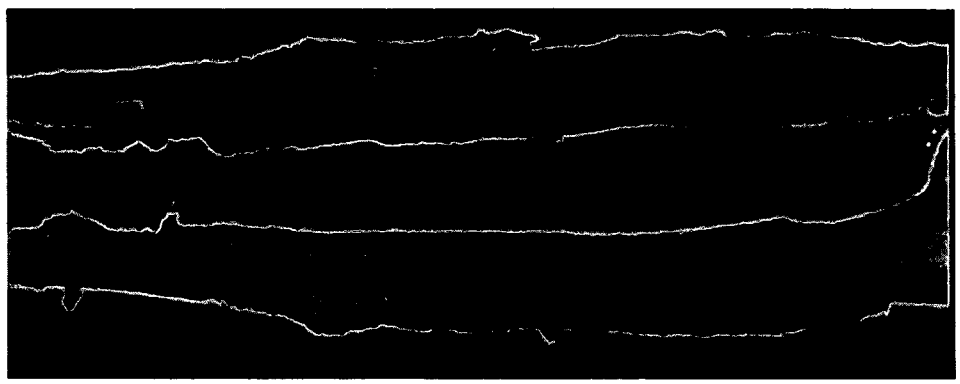
FIG. 43 illustrates explanted brushed ePTFE vascular grafts which were seeded with cells and treated with platelet-poor plasma prior to implantation.

FIG. 43 illustrates a gross photograph of explanted brushed ePTFE vascular grafts which were seeded with cells and treated with platelet-poor plasma prior to implantation. As shown in FIG. 43, such bePTFE™ grafts treated in this manner show less signficant thrombosis formation.

One randomly selected entire hemisection also underwent scanning electron microscopy (SEM) to determine the extent of apparent luminal endothelial cells, e.g. to determine the extent to which the graft lumen endothelialtized or developed an intima during the implantation period. To avoid confounding endothelialization from cell seeding with endothelial outgrowth from anastomoses, a well-known phenomena in which endothelial cell outgrowth from native tissue occurs at the graft connection points, a six week implant duration was chosen. During this period it was believed that graft endothelialization from anastomotic regions towards the midgraft region would be limited to approximately one centimeter, and that the central regions of each graft would best demonstrate the effects of the experimental variables on endothelialization, i.e., neointimal formation.

Figure 44:
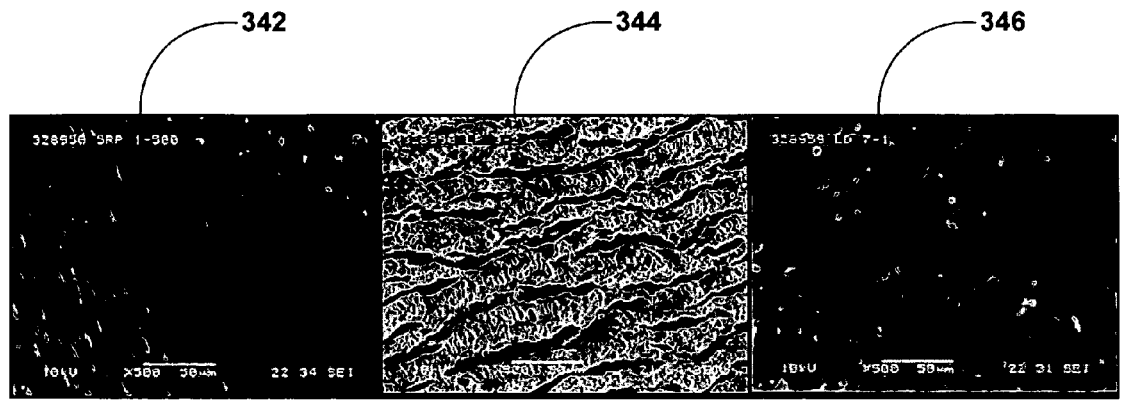
FIG. 44 illustrates SEM images of the luminal surfaces of: a native artery; an ePTFE vascular graft after six weeks implantation; and a brushed ePTFE vascular graft after six weeks implantation.

A montage of SEM micrographs was used to build a high magnification image of each hemisection. This montage was divided into ten equal size regions (nominal 4 mm length) from proximal to distal anastomosis, and three representative high magnification micrographs were then taken in each region. Segmenting the graft into ten regions and analyzing each for extent of endothelialization was then intended to capture the extent of anastomotic outgrowth while showing midgraft impact/growth of seeded endothelial cells. To avoid a potential overestimation of graft endothelialization by endothelial outgrowth from anastomoses, the analysis of the graft explant data focused on scores over the central four regions of each graft i.e., regions 4,5,6 and 7. Four scorers then scored each region blindly for extent of apparent endothelial cell coverage using the following scale: 0=no cells, 1=0-25% coverage, 2=25-50% coverage, 3=50-75% coverage, 4=75-100% coverage, 5=100% coverage, FIG. 44 illustrates a SEM image 342 of the luminal surface of a native artery, a SEM image 344 of the luminal surface of an ePTFE vascular graft after seeks weeks implantation, and a SEM image 346 of the luminal surface of a brushed ePTFE vascular grafts after six weeks implantation. SEM image 342 illustrates the natural endothelial cell lining of the native artery. SEM image 344 illustrates, after six weeks implantation, the bare node-and-fibril structures of an untreated ePTFE graft. SEM image 346 shows the confluent endothelial lining formed on a bePTFE™ graft that received endothelial cell seeding.

As illustrated by FIG. 44, the substantially complete neointimal formation or endothelialization of the bePTFE™ graft as illustrated by image 346 approximates the natural endothelial cell lining of the native artery in image 332, while the bare node-and-fibril structures of an untreated ePTFE graft (even after six weeks implantation) does not. The image of the bePTFE™ graft would likely have been scored as a "5" in the SEM micrograph endothelialization evaluation portion of the experiment.

Figure 45:
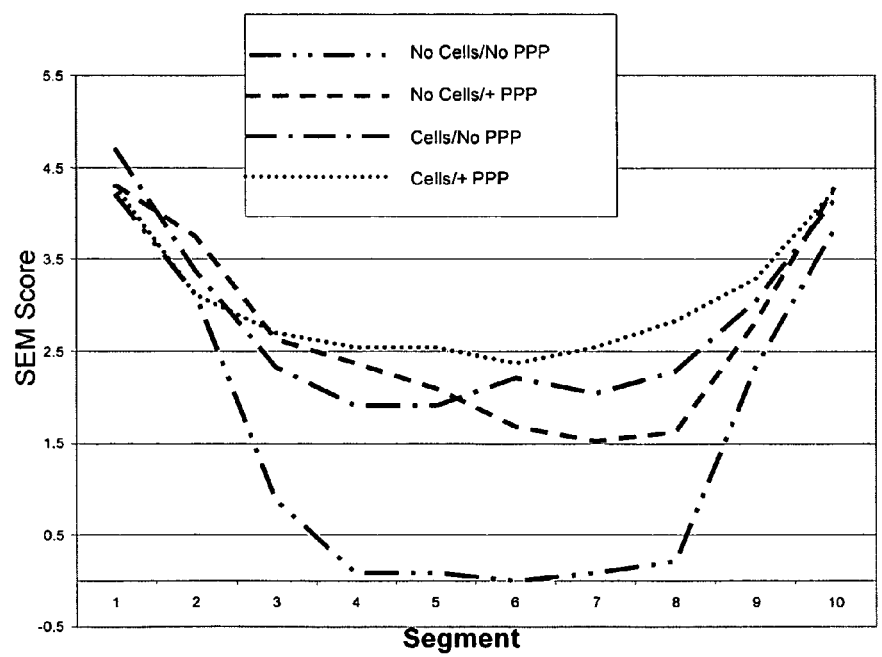
FIG. 45 is a graph illustrating average endothelialization scores at various longitudinal locations of explanted vascular grafts for four groups of the grafts, the grafts grouped according to whether they were seeded with cells and treated with platelet-poor plasma prior to implantation.

FIG. 45 is a graph illustrating average endothelialization scores for various segments of the explanted vascular grafts for four groups of the grafts, the grafts grouped according to whether they were seeded with cells and treated with platelet-poor plasma prior to implantation. The data in FIG. 46 also shows the soundness of the choice of focusing on regions 4, 5, 6 and 7 to show the impact of cell seeding without influence from anastomotic outgrowth. The control group involving no PPP treatment and no cell seeding showed essentially no evidence of neointima formation in the midgraft region at six weeks The combination of endothelial cells with PPP pre-treatment resulted in the highest levels of neointima development, with the PPP alone and cell seeding alone treatments falling just underneath the performance of the combined treatment. The latter three curves were not statistically different from each other, but all were statistically higher than the control group involving no PPP treatment and no cell seeding. Accordingly, FIG. 46 suggests that PPP treatment, cell seeding prior to implantation, and particularly the combination thereof, provide significant benefits with respect to midgraft endothelialization of implanted vascular grafts.

Figure 46:
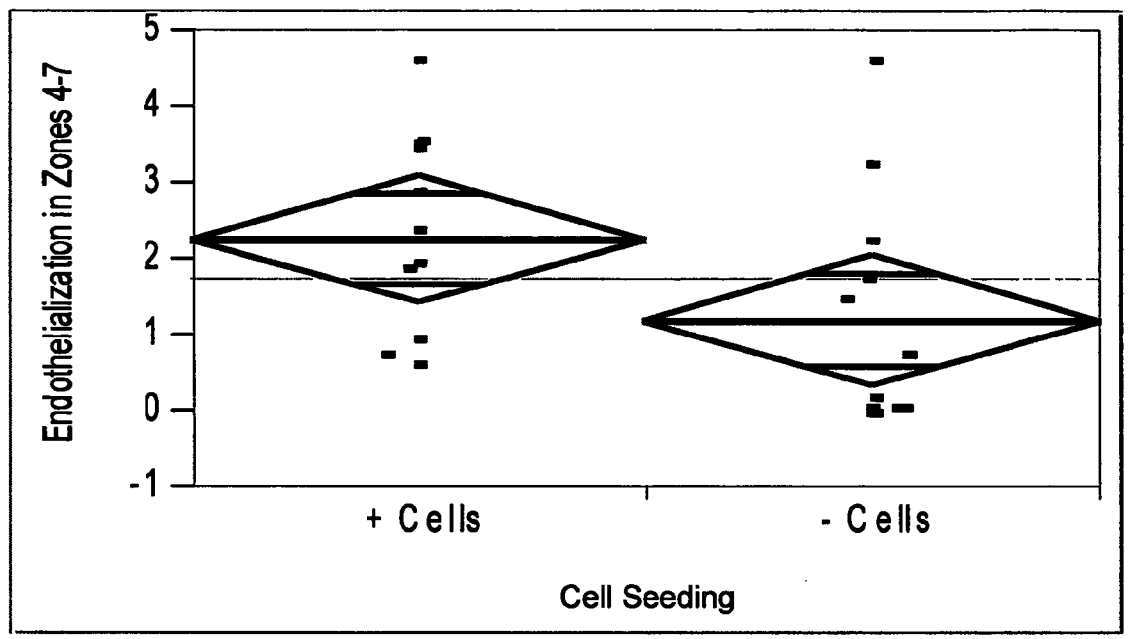
FIG. 46 is a graph illustrating midgraft endothelization scores for the explanted vascular grafts divided into two groups based on whether or not the grafts were seeded with cells prior to implantation.

FIG. 46 is a graph illustrating midgraft endothelization scores for the explanted vascular grafts divided into two groups based on whether or not the grafts were seeded with cells prior to implantation. As illustrated by the means diamonds for each group, the grafts seeded with cells prior to implantation had significantly higher endothelialization scores than those not seeded with cells (P<0.04).

Figure 47:
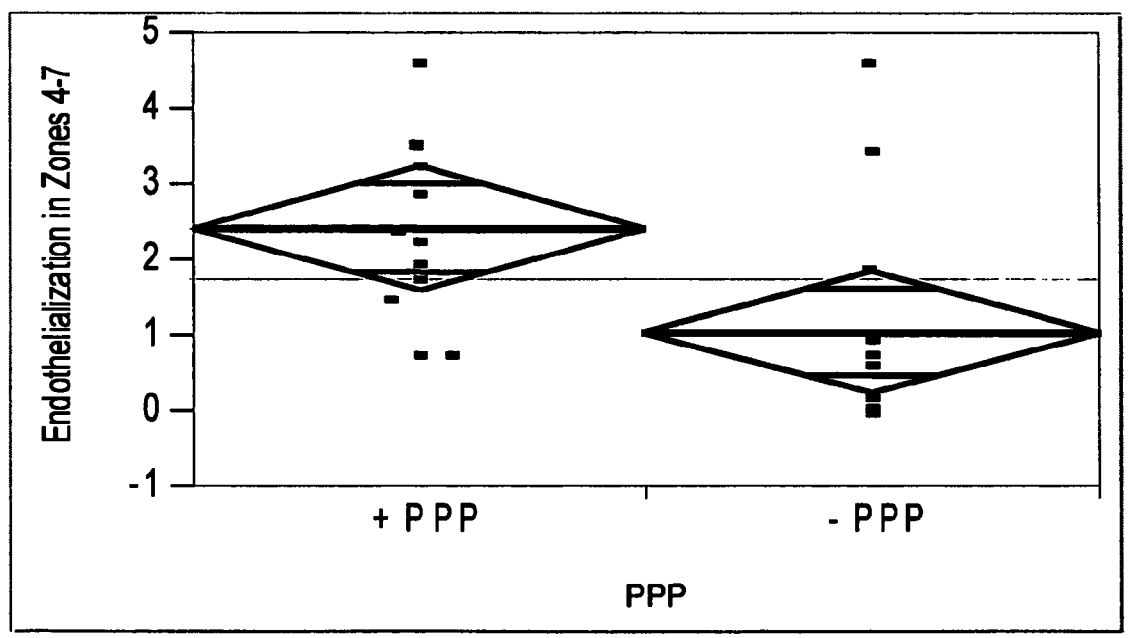
FIG. 47 is a graph illustrating the midgraft endothelization scores for the explanted vascular grafts divided into two groups based on whether or not the grafts were treated with platelet-poor plasma prior to implantation.

FIG. 47 is a graph illustrating the midgraft endothelization scores for the explanted vascular grafts divided into two groups based on whether or not the grafts were treated with platelet-poor plasma prior to implantation. As illustrated by means diamonds for each group, the grafts treated with PPP prior to implantation had significantly higher endothelialization scores than those not treated with PPP (P<0.01).

FIG. 48 is a table showing patency data from excised vascular prostheses removed from the dogs in the animal study. Of the sixteen ePTFE grafts implanted, 6 grafts (37%) were occluded such that blood would be substantially unable to pass through the graft. Of the 6 occluded grafts, 2 grafts were infected. Of the 16 bePTFE™ grafts implanted in the dogs, only 2 grafts (12%) were occluded. Both occluded grafts were infected. Therefore, all noninfected bePTFE™ grafts showed no occlusions. In addition, as it can be seen that bePTFE™ grafts generally produced less occlusions in the study animals (P<0.07), this data suggests that overall the bePTFE™ grafts may show similar favorable performance in humans.

FIG. 49 is an ANOVA table showing statistical data (P values) from analyses of the excised vascular grafts. Examining the test variable depicted in FIG. 49, the cell-seeding variable (cell seeding vs. no cell seeding) was highly significant in terms of the measurements of thrombosis (P<0.004) and neointimal formation (P<0.04), with near significance with respect to patency (P<0.08). With respect to material (ePTFE vs. bePTFE™) the bePTFE™ was significantly less thrombogenic compared to ePTFE (P<0.0001), with patency analysis showing close to a statistically significant difference (P<0.07). The effect of the directionality of the bePTFE™ (forward vs. reverse) did not have any influence on patency, thrombosis, or neointimal formation. The effect of platelet poor plasma treatment (PPP vs. no PPP) appeared highly significant in terms of PPP treatment being associated with lower thrombosis (P<0.009) and more significant neointimal formation (P<0.01).

In this manner, the study of grafts implanted in dogs identified that cell seeding, bePTFE™, and PPP treatment may reduce thrombosis formation, increase patency, and increase neointimal formation in implanted grafts. Accordingly, a seeded bePTFE™ graft that was pre-treated with PPP may be less likely to be rejected, and may therefore last longer in a patient than other grafts that are not bePTFE™, not seeded, and/or not treated with PPP.

As described above, one randomly selected hemisection of each graft was used for SEM analyis. The other hemisection of each graft was sectioned for histological examination. More particularly, a midgraft section was created for radial sectioning and the resultant proximal and distal segments of graft-underwent longitudinal sectioning. Various sections were stained with Haematoxylin and Eosin for cellurality, Masson's Trichrome for collagen/fibrous capsule, phosphotungstic acid (PTAH) for fibrin/acute thrombosis, or elasting stain for elastin. The grafts were then reviewed for neointimal formation, cellularity, macrophage infiltration, and thrombosis. The scoring system applied by the histopathologist for each category was: 0=minimal to none, 1=low, 2=intermediate, and 3=significant.

Neointima formation refers to the endothelialization of the surface with virtually no underlying cellular or tissue component. Neointima with endothelialization was identified by the presence of cellular nuclei on the surface of the vascular graft. Strictly speaking, it was the endothelialization that was measured in this category, not necessarily the neointima with its endothelium and underlying smooth muscle cells and fibroblasts.

Cellularity refers to the cellular component within the interstices of the porous luminal graft surface. Cellularity at the anastomosis was not included in the histological scoring for cellularity.

Macrophage infiltration is commonly seen from the peri-adventitial tissue (outer surface) with monocyte and macrophage infiltration into the porosity of the vascular graft. Macrophage infiltration on the outer portion of the vascular graft is contiguous with the foreign body reaction at the adventitial surface, which is composed of macrophages and foreign body giant cells.

FIG. 51 is an ANOVA table showing statistical data (P values) derived from the histological evaluation of the vascular grafts removed from the canines in the animal study. As illustrated in FIG. 51, the statistical analysis indicated that the surface of the bePTFE™ produces less thrombosis when compared to ePTFE (P<0.08), confirming the results from the gross observation and scoring discussed with respect to FIG. 50. In addition, although not strictly significantly different, the graft cellularity was greater for bePTFE™ when compared to ePTFE (P<0.09).

Confirming the SEM results, the histological analysis indicated that neointima formation was statistically significantly enhanced by cell seeding (P<0.008). Graft cellularity was also statistically significantly enhanced by cell seeding (P<0.001). Macrophage infiltration was statistically significantly increased when the grafts were seeded with cells compared to no cell seeding (P<0.007).

In this manner, the histological study of the grafts implanted in dogs identified that cell seeding, bePTFE™, and PPP treatment may reduce thrombosis formation, increase patency, and increase neointimal formation in implanted grafts. Accordingly, a seeded bePTFE™ graft that was pre-treated with PPP may be less likely to be rejected, and may therefore last longer in a patient than other grafts that are not bePTFE™, not seeded, and/or not treated with PPP.

Figure 51A:
FIGS. 51A-51C are histological slides of explanted grafts illustrating neointimal formation.
Figure 51B:
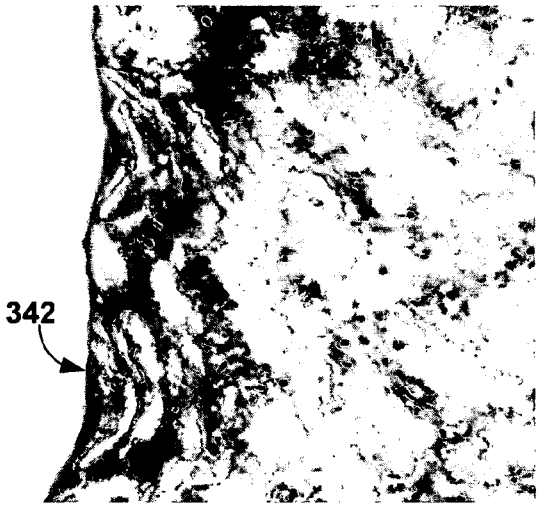
Figure 51C:
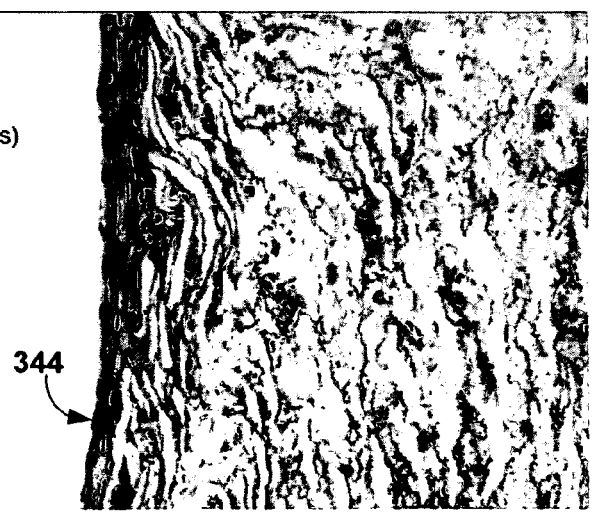
Figure 53:
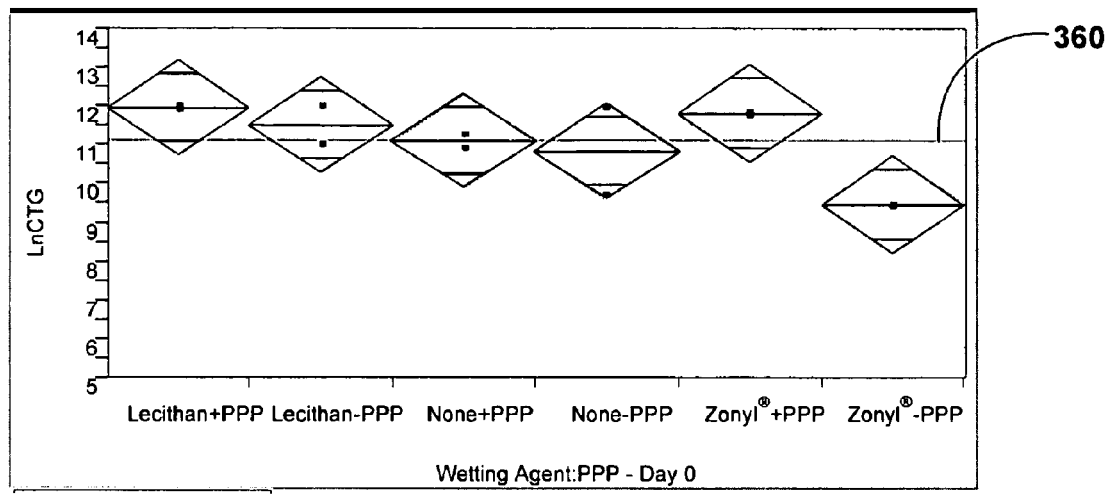
FIGS. 53 and 54 are graphs illustrating experimental cell retention and growth data derived from grafts treated with one of two wetting agents, or no wetting agent, before cell seeding in another in vitro experiment.
Figure 54:
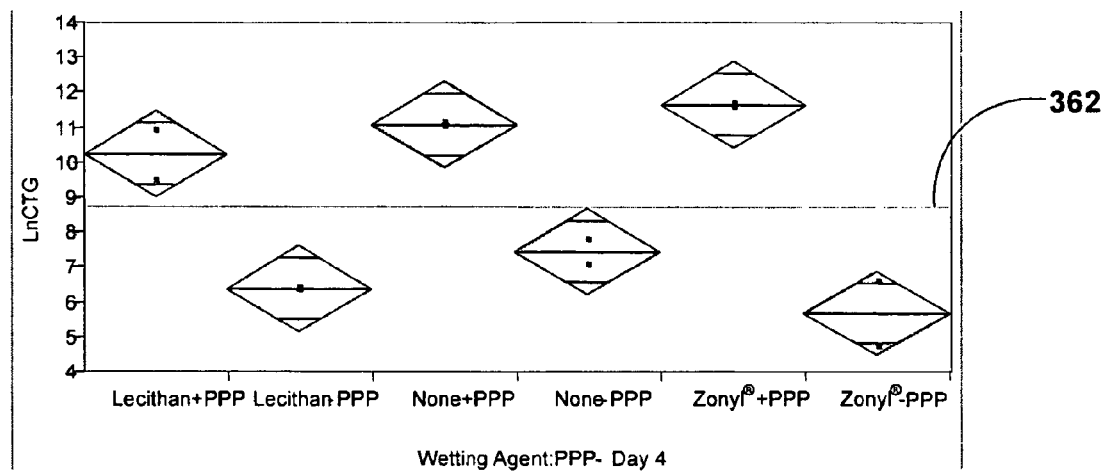
Figure 55:
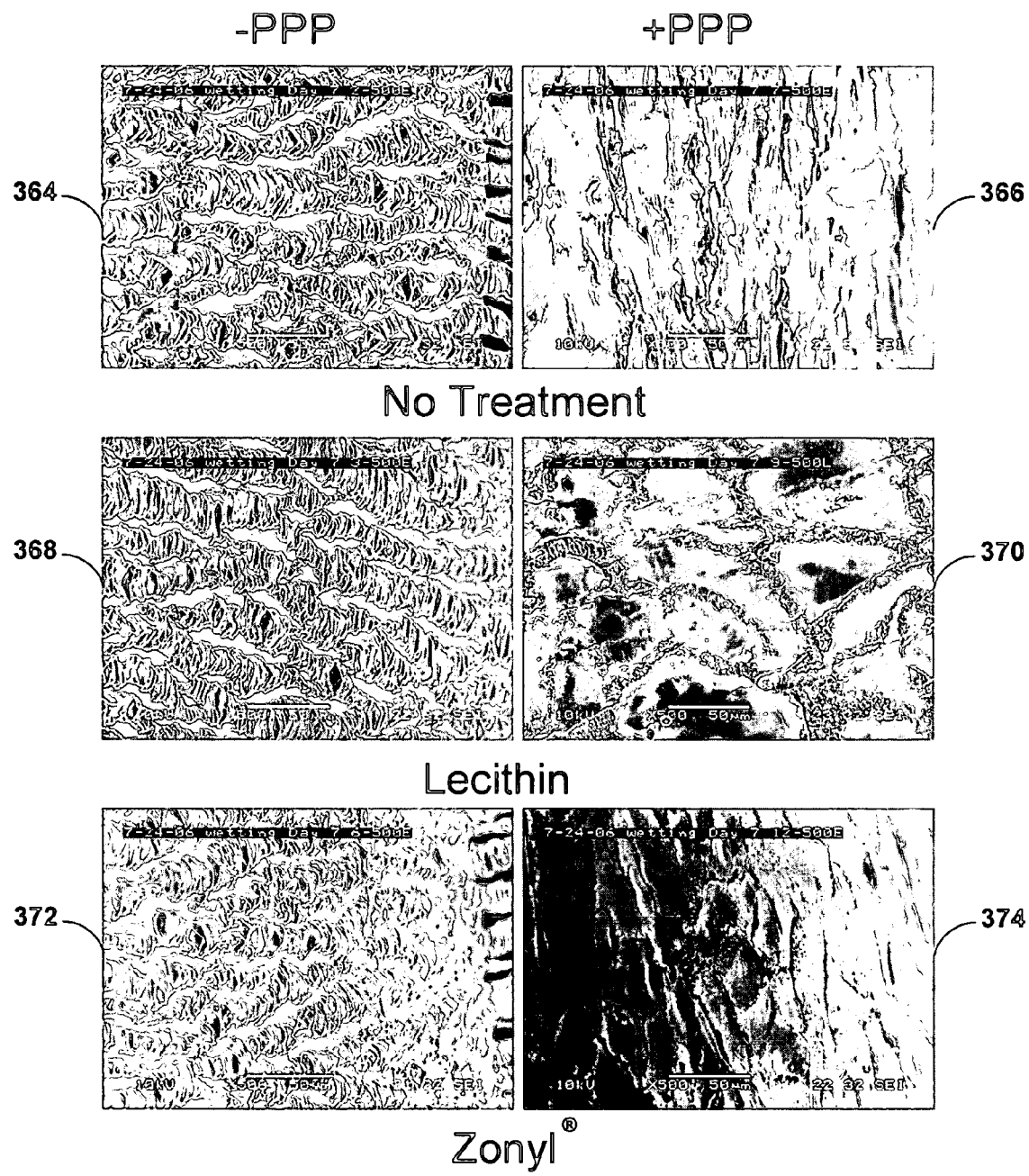
FIG. 55 illustrates SEM images of the luminal surfaces of example grafts from the wetting agent experiment.

FIGS. 51A-51C are histological slides of explanted grafts illustrating neointimal formation. The darkened areas 342 and 344 near the luminal surfaces of the bePTFE™ grafts are neointimal nuclei, which are present in the bePTFE™ grafts and not the ePTFE

EXAMPLE 3

FIG. 52 is a table showing ranges of cell growth measured on prostheses treated with different mediums before cell seeding. The in vitro experiment of Example 3 was performed to identify potential pre-treatments of prostheses, or grafts, that would encourage endothelial cell growth over a greater surface area of the graft. Both ePTFE and bePTFE™ grafts were treated with one of fetal bovine serum, human fibronectin, PPP from the Magellan™ separator, or Matrigel™. Fibronectin is an extracellular adhesion molecule, and Matrigel™ is a basement membrane matrix product of BD Biosciences of Franklin Lakes, N.J.

After treatment, each graft was seeded with endothelial cells and centrifuged for 5 minutes to adhere the cells to the lumen of the graft. The numbers of initial cells were counted and the graft was incubated at 37 degrees Celsius for 5 days in-vitro. After 5 days, each graft was removed, and the amount of cells was determined. The table of FIG. 38 shows the number of cells on the grafts for each pre-treatment, when compared to the initial count of cells, expressed as ranges of percentages of the initial count. A percentage below 100% indicates that cells were lost during the 5 day incubation period and a percentage above 100% indicates an increase in the amount of cells on the graft.

As shown by FIG. 52, all grafts pre-treated with PPP displayed an increase of the number of endothelial cells on the graft, while the Matrigel treated grafts show a varying range of success. Grafts pre-treated with serum or fibronectin lost a substantial amount of cells from the incubated cells. The results of Example 3 indicate that PPP from the Magellan separator may encourage endothelial cell growth on the graft.

EXAMPLE 4

Example 4 illustrates the impact that wetting agents had on cell-seeded test grafts that had and had not been treated with PPP. In this in vitro experiment, two wetting agents, lecithin and Zonyl® FSO were each used to wet grafts according to the procedures illustrated in FIGS. 26 and 29. Additionally, grafts without a wetting agent were used as an experimental control. Endothelial cell seeding was applied to grafts that varied both in wetting agent application (none vs. lecithin vs. Zonylϕ FSO) and PPP application (none vs. with PPP). A CTG assay was performed after cell seeding (at day 0) to indicate the number of cells that adhered to each graft. The grafts were incubated for 4 days, and an additional CTG assay was performed.

FIG. 49 shows the results of the CTG assays performed at day 0. At day 0, all samples received and retained approximately the same number of endothelial cells. FIG. 50 shows the results of the CTG assays performed at day 4. All graft samples that did not receive PPP treatment showed a distinct loss of cells. All graft samples that received PPP treatment, both with and without treatment by one of the two wetting agents, showed approximately the same number of cells as adhered to the graft at day 0. These results show how PPP improves cell adhesion during an incubation period. Additionally, these results suggest that neither lecithin nor Zonyl® FSO caused cell death.

Various embodiments of the invention have been described. The invention is not limited to the particular embodiments described above. In particular, the invention is not limited to vascular prostheses that include ePTFE. Although many implantable devices use ePTFE, other biocompatible materials, such as woven or veloured Dacron, also may used to form vascular prostheses or other implantable medical devices. Some materials may be processed as described above to create recesses sized to receive endothelial cells and may be seeded with axial centrifugation. In addition, the materials may be subjected to pre-implantation processing in addition to that described herein. For example, to improve wettability, a device may be subjected to one or more gases—such as air, oxygen, argon, or water vapor—under gas-plasma discharge conditions, or treated with chemicals such as a sodium naphthalene complex.

Moreover, the invention is not limited to use of any particular apparatus. There are many different kinds of apparatus that can be used to seed vascular prostheses or other implantable medical devices with centrifugation, and the invention is not limited to the particular illustrative apparatus described herein. Furthermore, the invention is not limited to the exemplary centrifugation times or speeds mentioned herein. These and other embodiments are within the scope of the following claims.

The invention claimed is:

1. A method comprising:
    inserting an implantable medical device having a lumen into a protective sleeve;
    inserting the protective sleeve into a tube through an open end of the tube, wherein the tube defines a longitudinal axis;
    sealing the open end of the tube with a self-sealable membrane fabricated from a self-sealable material, wherein the self-sealable membrane provides a selective liquid barrier at the open end of the tube;
    delivering a preparation media comprising calcium to said lumen of the implantable medical device by penetrating said self-sealable membrane with a delivery device;
    after a first application period, removing any residue preparation media from said lumen through said self-sealable membrane with a removal device;
    subsequent to removing any residue preparation media, delivering a blood centrifugation product comprising blood plasma to said lumen of the implantable medical device by penetrating said self-sealable membrane with the delivery device;
    after a second application period, removing any residue of the blood centrifugation product from said lumen through said self-sealable membrane with the removal device;
    subsequent to removing any residue centrifugation product, delivering cells to said lumen of the implantable medical device by penetrating said self-sealable membrane with the delivery device;
    withdrawing the delivery device to re-establish the liquid barrier at said self-sealable membrane; and
    centrifuging the implantable medical device with the cells in the lumen by rotating the tube substantially around the longitudinal axis.

2. The method of claim 1, further comprising securing the self-sealable membrane over the open end with a tube cap.

3. The method of claim 1, further comprising:
    removing the implantable medical device from the protective sleeve; and
    implanting the implantable medical device after removing the implantable medical device from the protective sleeve.

4. The method of claim 1, further comprising:
    removing the protective sleeve from the tube;
    implanting the implantable medical device; and
    removing the implantable medical device from the protective sleeve after implanting the implantable medical device.

5. The method of claim 4, further comprising attaching the protective sleeve to a tunneling device, wherein implanting the implantable medical device comprises drawing the protective sleeve and the implantable medical device through a tunnel formed through patient tissue by the tunneling device with the sleeve attached to the tunneling device.

6. The method of claim 1, wherein inserting the implantable medical device comprises inserting a vascular prosthesis.

7. The method of claim 1, further comprising centrifuging the implantable medical device with the cells in the lumen by rotating the tube substantially around the longitudinal axis at a rate sufficient to develop between 250-500 g for 1-10 minutes.

8. The method of claim 1, wherein the protective sleeve has an inner diameter that is sized to substantially conform to an outer diameter of the implantable medical device.

* * * * *